United States Patent
Marasco et al.

(10) Patent No.: US 12,258,378 B2
(45) Date of Patent: Mar. 25, 2025

(54) ENGINEERED CELLS, T CELL IMMUNE MODULATING ANTIBODIES AND METHODS FOR USING THE SAME

(71) Applicant: Dana-Farber Cancer Institute, Inc., Boston, MA (US)

(72) Inventors: Wayne A. Marasco, Wellsley, MA (US); Quan Karen Zhu, Southborough, MA (US); Emily Kuiper, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1137 days.

(21) Appl. No.: 16/980,742

(22) PCT Filed: Mar. 14, 2019

(86) PCT No.: PCT/US2019/022272
§ 371 (c)(1),
(2) Date: Sep. 14, 2020

(87) PCT Pub. No.: WO2019/178356
PCT Pub. Date: Sep. 19, 2019

(65) Prior Publication Data
US 2021/0163570 A1  Jun. 3, 2021

Related U.S. Application Data

(60) Provisional application No. 62/657,151, filed on Apr. 13, 2018, provisional application No. 62/643,040, filed on Mar. 14, 2018.

(51) Int. Cl.
*C07K 14/705* (2006.01)
*A61K 39/00* (2006.01)
*C07K 16/28* (2006.01)
*C12N 5/0783* (2010.01)

(52) U.S. Cl.
CPC ........ *C07K 14/705* (2013.01); *A61K 39/4611* (2023.05); *A61K 39/4631* (2023.05); *A61K 39/464421* (2023.05); *C07K 16/2818* (2013.01); *C07K 16/2827* (2013.01); *C07K 16/2866* (2013.01); *C12N 5/0636* (2013.01); *A61K 2239/23* (2023.05); *A61K 2239/29* (2023.05); *A61K 2239/49* (2023.05); *C07K 2317/565* (2013.01); *C12N 2510/00* (2013.01)

(58) Field of Classification Search
CPC .............. C07K 14/705; C07K 16/2818; C07K 16/2827; C07K 16/2866; C07K 2317/565; C12N 5/0636; C12N 2510/00
See application file for complete search history.

(56) References Cited

U.S. PATENT DOCUMENTS

| | | |
|---|---|---|
| 4,683,202 A | 7/1987 | Mullis |
| 4,797,368 A | 1/1989 | Carter et al. |
| 4,946,778 A | 8/1990 | Ladner et al. |
| 5,091,513 A | 2/1992 | Huston et al. |
| 5,132,405 A | 7/1992 | Huston et al. |
| 5,139,941 A | 8/1992 | Muzyczka et al. |
| 5,928,906 A | 7/1999 | Koester et al. |
| 5,994,136 A | 11/1999 | Naldini et al. |
| 6,013,516 A | 1/2000 | Verma et al. |
| 8,329,178 B2 | 12/2012 | Marasco et al. |
| 2011/0104263 A1 | 5/2011 | Lo et al. |
| 2011/0250165 A1 | 10/2011 | Marasco et al. |
| 2014/0114054 A1 | 4/2014 | Kurosawa et al. |
| 2016/0060326 A1* | 3/2016 | Zhou ........................ A61P 31/04 424/170.1 |
| 2017/0362297 A1* | 12/2017 | Marasco .......... C07K 14/70521 |
| 2017/0362325 A1 | 12/2017 | Jung et al. |
| 2017/0369594 A1 | 12/2017 | Neijssen et al. |

FOREIGN PATENT DOCUMENTS

| | | | |
|---|---|---|---|
| EP | 3090759 | 11/2016 | |
| WO | 2005/060520 | 7/2005 | |
| WO | 2006/089141 | 8/2006 | |
| WO | WO-2006089141 A2 * | 8/2006 | .............. A61P 31/18 |
| WO | 2007/065027 | 6/2007 | |
| WO | 2009/086514 | 7/2009 | |
| WO | 2009/079259 | 10/2009 | |
| WO | 2011/153380 | 12/2011 | |
| WO | 2013/166500 | 11/2013 | |
| WO | 2014/055897 | 4/2014 | |
| WO | 2014/144061 | 12/2014 | |
| WO | 2015/143194 | 9/2015 | |

(Continued)

OTHER PUBLICATIONS

England et al., Molecular Imaging of Pancreatic Cancer with Antibodies, 2015, Molecular Pharmaceuticals, vol. 13, pp. 8-24 (Year: 2015).*

(Continued)

*Primary Examiner* — Jeffrey Stucker
*Assistant Examiner* — Brittney E Donoghue
(74) *Attorney, Agent, or Firm* — Baker Donelson

(57) ABSTRACT

This invention is directed to engineered cells and methods for using the same. In embodiments, the engineered cell comprises a nucleic acid encoding a chimeric antigen receptor and a polypeptide, wherein the chimeric antigen receptor is specific for two or more antigens on the surface of a cancer cell, and wherein the polypeptide comprises an antibody or fragment thereof that can be secreted from the engineered cell.

19 Claims, 32 Drawing Sheets

Specification includes a Sequence Listing.

(56) References Cited

FOREIGN PATENT DOCUMENTS

| WO | 2015/164865 | 10/2015 | |
|---|---|---|---|
| WO | WO-2016033570 A1 * | 3/2016 | ............ A61K 35/17 |
| WO | 2016/054638 | 4/2016 | |
| WO | 2016/057488 | 4/2016 | |
| WO | 2016/100985 | 6/2016 | |
| WO | 2016/164835 | 10/2016 | |
| WO | 2017/048824 | 3/2017 | |

OTHER PUBLICATIONS

Abd-Elazeem, Mona A., and Marwa A. Abd-Elazeem. "Claudin 4 expression in triple-negative breast cancer: correlation with androgen receptors and Ki-67 expression." Annals of diagnostic pathology 19.1 (2015): 37-42.

Yu, Shaonan, et al. "High level of CXCR4 in triple-negative breast cancer specimens associated with a poor clinical outcome." Acta Medica Okayama 67.6 (2013): 369-375.

Ausubel, F.M., Brent, R., Kingston, R.E., Moore, D.D., Seidman, J.G., Smith, J.A. and Struhl, K. (1994) Current Protocols in Molecular Biology. Wiley, New York. *We submitted the 2003 version of this reference*.

Baichwal, Vijay R., and Bill Sugden. "Vectors for gene transfer derived from animal DNA viruses: transient and stable expression of transferred genes." Gene Transfer. Springer, Boston, MA, 1986. 117-148.

Benovic, Jeffrey L., and Adriano Marchese. "A new key in breast cancer metastasis." Cancer cell 6.5 (2004): 429-430.

Blömer, Ulrike, et al. "Highly efficient and sustained gene transfer in adult neurons with a lentivirus vector." Journal of virology 71.9, (1997).

Connor, Ruth I., et al. "Change in coreceptor use correlates with disease progression in HIV-1-infected individuals." The Journal of experimental medicine 185.4 (1997): 621-628.

Cotten, Matt, et al. "High-efficiency receptor-mediated delivery of small and large (48 kilobase gene constructs using the endosome-disruption activity of defective or chemically inactivated adenovirus particles." Proceedings of the National Academy of Sciences 89.13 (1992): 6094-6098.

Coupar, Barbara EH, Marion E. Andrew, and David B. Boyle. "A general method for the construction of recombinant vaccinia viruses expressing multiple foreign genes." Gene 68.1 (1988): 1-10.

Curiel, David T. "High-efficiency gene transfer employing adenovirus-polylysine-DNA complexes." Natural immunity 13.2-3 (1994): 141-164.

Foulkes WD, et al (2010) Triple-negative breast cancer. The New England journal of medicine. 2010; 363(20): 1938-48.

Friedmann, Theodore. "Progress toward human gene therapy." Science 244.4910 (1989): 1275-1281.

Grunhaus and Horwitz, 1992. Adenoviruses as cloning vectors. Rice C (ed) Seminars in virology, vol. 3:237-252.

Hernandez, Paolo A., et al. "Mutations in the chemokine receptor gene CXCR4 are associated with WHIM syndrome, a combined immunodeficiency disease." Nature genetics 34.1 (2003): 70-74.

Horwich, A. L., et al. "Synthesis of hepadnavirus particles that contain replication-defective duck hepatitis B virus genomes in cultured HuH7 cells." Journal of virology 64.2 (1990): 642-650.

Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.

Imitola, Jaime, et al. "Directed migration of neural stem cells to sites of CNS injury by the stromal cell-derived factor 1a/CXC chemokine receptor 4 pathway." Proceedings of the National Academy of Sciences 101.52 (2004): 18117-18122.

Inouye, Sumiko, and Masayori Inouye. "Up-promoter mutations in the lpp gene of *Escherichia coli*." Nucleic acids research 13.9 (1985): 3101-3110.

International Preliminary Report on Patentability for PCT/US2019/022272 dated Sep. 15, 2020.

International Search Report for PCT/US2019/022272 dated Aug. 12, 2019.

Joyner, Alexandra L., William C. Skarnes, and Janet Rossant. "Production of a mutation in mouse En-2 gene by homologous recombination in embryonic stem cells." Nature 338.6211 (1989): 153-156.

Kelleher, Z. T., and J. M. Vos. "Long-term episomal gene delivery in human lymphoid cells using human and avian adenoviral-assisted transfection." Biotechniques 17.6 (1994): 1110-1117.

Knaut, Holger, et al. "A zebrafish homologue of the chemokine receptor Cxcr4 is a germ-cell guidance receptor." Nature 421.6920 (2003): 279-282.

Kunert, Andre, and Reno Debets. "Engineering T cells for adoptive therapy: outsmarting the tumor." Current opinion in immunology 51 (2018): 133-139.

Kunwar, Prabhat S., and Ruth Lehmann. "Germ-cell attraction." Nature 421.6920 (2003): 226-227.

Laughlin, C. A., C. B. Cardellichio, and H. C. Coon. "Latent infection of KB cells with adeno-associated virus type 2." Journal of virology 60.2 (1986): 515-524.

Lebkowski, Jane S., et al. "Adeno-associated virus: a vector system for efficient introduction and integration of DNA into a variety of mammalian cell types." Molecular and cellular biology 8.10 (1988): 3988-3996.

Li, Yan M., et al. "Upregulation of CXCR4 is essential for HER2-mediated tumor metastasis." Cancer cell 6.5 (2004): 459-469.

Lu, Meiling, Elizabeth A. Grove, and Richard J. Miller. "Abnormal development of the hippocampal dentate gyrus in mice lacking the CXCR4 chemokine receptor." Proceedings of the National Academy of Sciences 99.10 (2002): 7090-7095.

Mann, Richard, Richard C. Mulligan, and David Baltimore. "Construction of a retrovirus packaging mutant and its use to produce helper-free defective retrovirus." Cell 33.1 (1983): 153-159.

Mansour, Suzanne L., Kirk R. Thomas, and Mario R. Capecchi. "Disruption of the proto-oncogene int-2 in mouse embryo-derived stem cells: a general strategy for targeting mutations to non-selectable genes." Nature 336.6197 (1988): 348-352.

McLaughlin, Susan K., et al. "Adeno-associated virus general transduction vectors: analysis of proviral structures." Journal of virology 62.6 (1988): 1963-1973.

MICAD Research Team. "[125I] Anti-claudin 4 monoclonal antibody." Molecular Imaging and Contrast Agent Database (MICAD)[Internet] (2007).

Miller, A. D. "Retroviral vectors." Curr Top Microbiol Immunol. 1992;158:1-24. doi: 10.1007/978-3-642-75608-5_1.

Muzyczka, N. "Use of adeno-associated virus as a general transduction vector for mammalian cells." Viral expression vectors (1992): 97-129 . . . Curr Top Microbiol Immunol. 1992;158:97-129. doi: 10.1007/978-3-642-75608-5_5.

Nagasawa, Takashi, et al. "Defects of B-cell lymphopoiesis and bone-marrow myelopoiesis in mice lacking the CXC chemokine PBSF/SDF-1." Nature 382.6592 (1996): 635-638.

Naldini, Luigi, et al. "In vivo gene delivery and stable transduction of nondividing cells by a lentiviral vector." Science 272.5259 (1996): 263-267.

Nicolas, Jean-François, and John LR Rubenstein. "Retroviral vectors." Vectors (1988): 493-513.

Paskind et al., 1975 "Dependence of Moloney murine leukemia virus production on cell growth," Virology. Sep. 1975;67(1):242-8. doi: 10.1016/0042-6822(75)90421-3.

Ridgeway, 1988 "Opposite effects of 1,25(OH)2D3 on synthesis and release of PTH compared with secretory protein I", Am J Physiol. Mar. 1988,254(3 Pt 1):E279-86. doi: 10.1152/ajpendo.1988.254.3.E279.

Roux et al., 1989, "Molecular basis of Sp alpha I/65 hereditary elliptocytosis in North Africa: insertion of a TTG triplet between codons 147 and 149 in the alpha-spectrin gene from five unrelated families," Blood. Jun. 1989;73(8):2196-201.

(56) References Cited

OTHER PUBLICATIONS

Sambrook, J. and Russell D. (2001). "Molecular cloning: A Laboratory Manual," Cold Spring Harbor Laboratory, Cold Spring Harbor, NY. *We have submitted the 2001 collection of manuals.*.

Scarlatti, Gabriella, et al. "In vivo evolution of HIV-1 co-receptor usage and sensitivity to chemokine-mediated suppression." Nature medicine 3.11 (1997): 1259-1265.

Suarez ER, et al (2016) Chimeric antigen receptor T cells secreting anti-PD-L1 antibodies more effectively regress renal cell carcinoma in a humanized mouse model. Oncotarget 7(23):34341-34355.

Temin, "Retroviruses and evolution", Cell Biophys. Dec. 1986;9(1-2):9-16. doi: 10.1007/BF02797372.

Thomas, Kirk R., and Mario R. Capecchi. "Site-directed mutagenesis by gene targeting in mouse embryo-derived stem cells." Cell 51.3 (1987): 503-512.

Tratschin, J. D., Irving L. Miller, and Barrie J. Carter. "Genetic analysis of adeno-associated virus: properties of deletion mutants constructed in vitro and evidence for an adeno-associated virus replication function." Journal of Virology 51.3 (1984): 611-619.

Tratschin, Jon-Duri, et al. "A human parvovirus, adeno-associated virus, as a eucaryotic vector: transient expression and encapsidation of the procaryotic gene for chloramphenicol acetyltransferase." Molecular and cellular biology 4.10 (1984): 2072-2081.

Written Opinion of the ISR for PCT/US2019/022272 mailed Aug. 12, 2019.

Zhou et al., 9th Conference on Retroviruses and Opportunistic Infections, Session 39 Poster Session, Abstract 189-M (2002).

Zufferey, Romain, et al. "Multiply attenuated lentiviral vector achieves efficient gene delivery in vivo." Nature biotechnology 15.9 (1997): 871-875.

\* cited by examiner

A

B

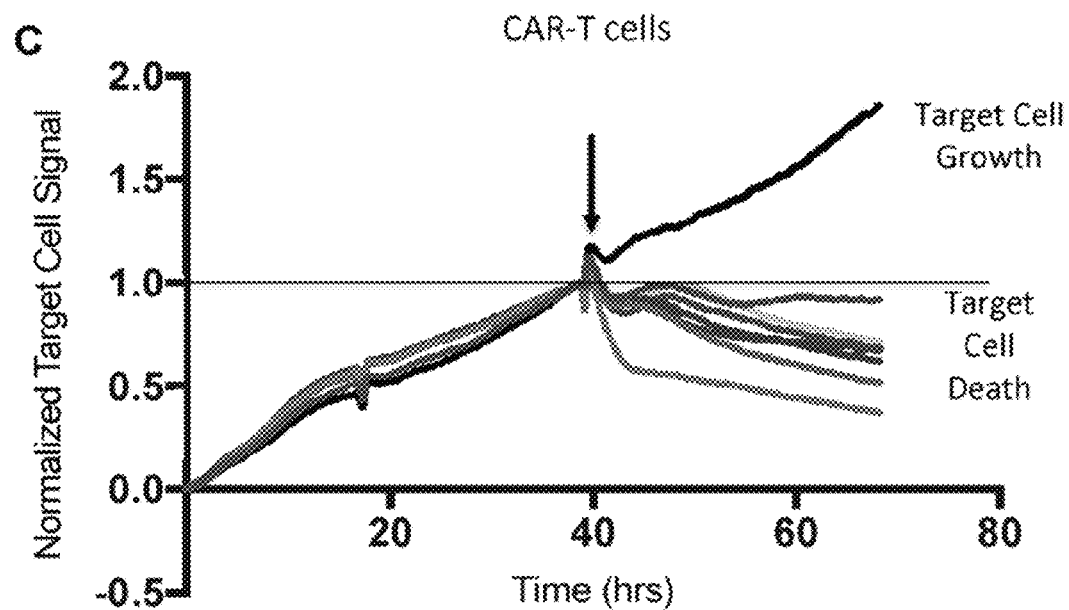
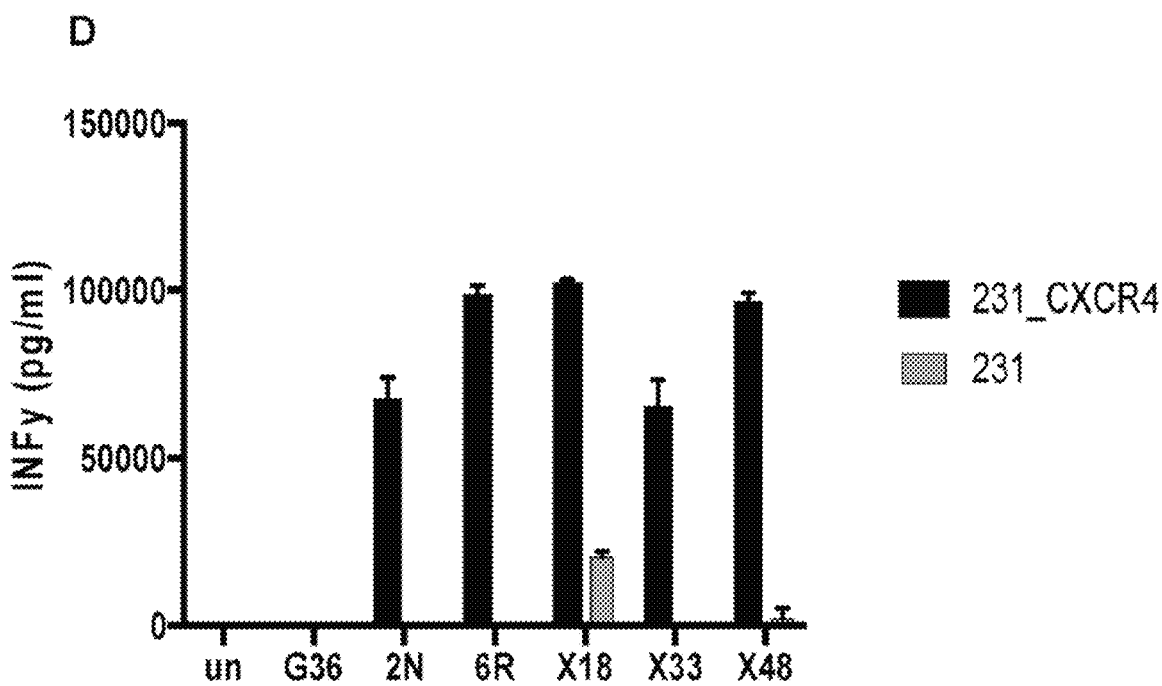
FIG. 2 CON'T

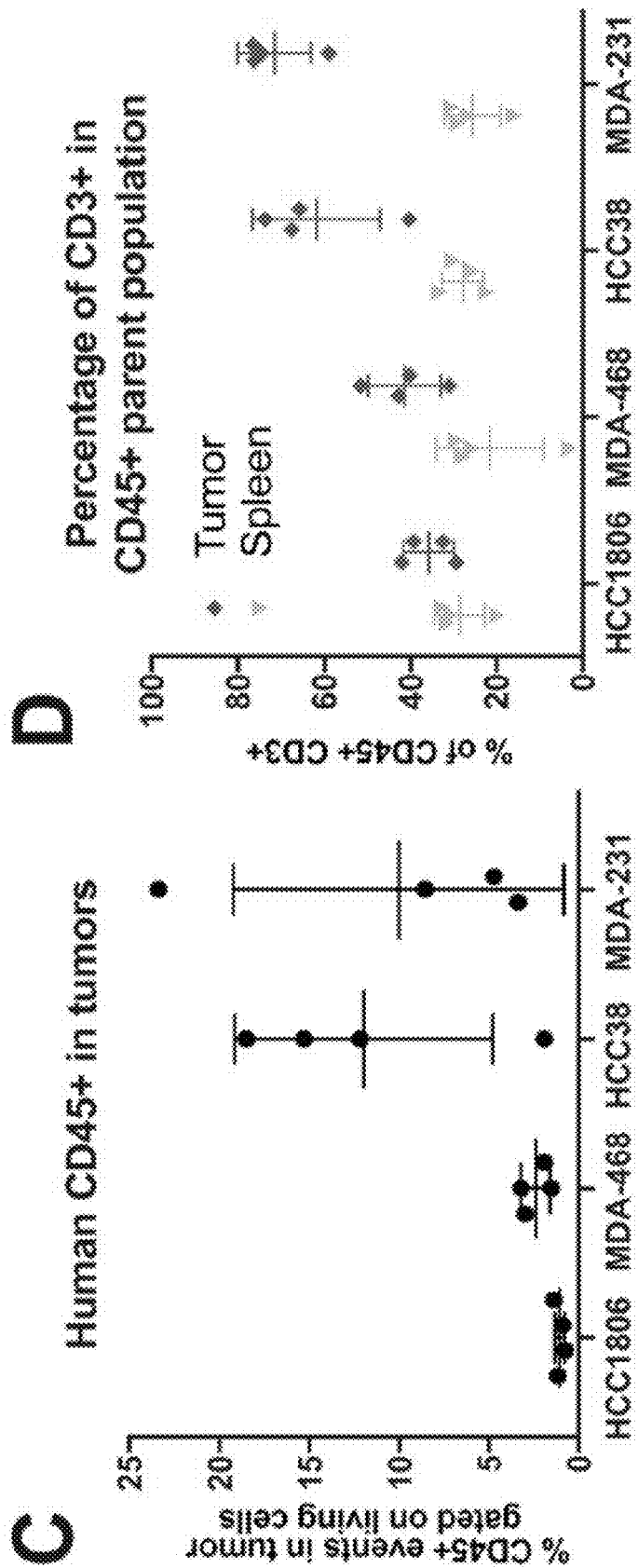
FIG. 11 - CONT.

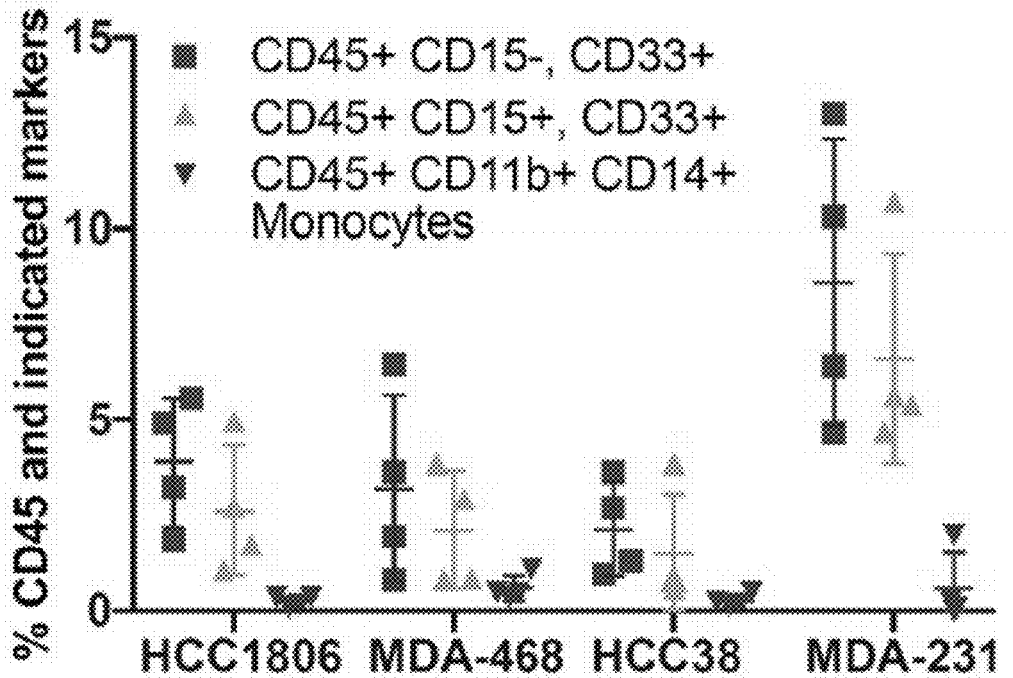
FIG. 11 - CONT.

Table 1: Tumor Weight (mg)

| | (mg) |
|---|---|
| HCC1806 | 402.5 |
| MDA-468 | 40 |
| HCC38 | 97.5 |
| MDA-231 | 67.5 |

| Sequence number | Sequence ID | V-GENE and allele | J-GENE and allele | D-GENE and allele | FR1-IMGT | CDR1-IMGT | FR2-IMGT |
|---|---|---|---|---|---|---|---|
| 1 | EK01_heavy | IGHV3-53*01 F | IGHJ3*02 F | IGHD4-23*01 ORF | EVQLVESGGGLVQPGGSLRLSCAAS | GFTV...SSNY | MSWVRQAPGKGLEWVSV |
| 2 | EK01_light | IGKV1-5*03 F | IGKJ4*01 F | | DIVMTQTPSTLSASVGDRVTITCRAS | QSI......NSW | LAWYQQKSGKAPKLLIY |

| Sequence ID | V-GENE and allele | J-GENE and allele | D-GENE and allele | FR1-IMGT | CDR1-IMGT | FR2-IMGT |
|---|---|---|---|---|---|---|
| hTIGITHis-E1-C3 (TIG1) | HV1-18*01 F | HJ4*02 F | HD3-10*01 F | QVQLVQSGAEVKKPGASVKVSCKAS | GYTF...TSYG | ISWVRQAPGQGLEWMGW |
| hTIGITHis-E2-E7 (TIG6) | HV3-74*02 F | HJ3*02 F | HD3-9*01 F | EVQLVQSGGGLVKPGGSLRLSCEAS | GFTF...SDYS | MSWVRQAPGKGLEWVSR |
| P5-E10 | HV6-5*01 F | HJ6*02 F | | EVQLVQSGAEVKKPGESLKISCKGS | GYSF...TNYW | IGWVRQMPGKGLEWMGI |
| P6-H12 | HV1-18*01 F | HJ5*02 F | HD6-13*01 F | EVQLVQSGAEVKKPGASVKVSCKAS | GYTF...TNYG | ISWVRQAPGQGLEWMGW |
| P6-G7 | HV1-69*01 F | HJ6*02 F | HD6-12*01 F | QVQLVQSGAEVKKPGSSVKVSCKAS | GGTF...SSYA | ISWVRQAPGQGLEWMGG |

| Sequence ID | V-GENE and allele | J-GENE and allele | D-GENE and allele | FR1-IMGT | CDR1-IMGT | FR2-IMGT |
|---|---|---|---|---|---|---|
| hTIGITHis-E1-C3 (TIG1) | LV1-44*01 F | LJ3*02 F | | SYELTQPPSASGTPGQRVTISCSGS | SSNI...GSNT | VSWYQQLPGTAPKLLIY |
| hTIGITHis-E2-E7 (TIG6) | LV1-44*01 F | LJ2*01 F | | SYELTQPPSASGTPGQRVTISCSGS | RSNI...GRNS | VNWYQQLPGTAPKLLIY |
| P5-E10 | LV1-44*01 F | LJ3*02 F | | LPVLTQPPSASGTPGQRVTISCSGS | SSNI...GSNT | VNWYQQLPGTAPKLLIY |
| P6-H12 | LV2-14*01 F | LJ2*01 F | | QSALTQPASVSGSPGQSITISCTGT | SSDVG...GYNY | VSWYQQHPGKAPKLMIY |
| P6-G7 | LV10-54*01 F | LJ3*02 F | | SYELTQPPSVSKGLRQTATLTCTGN | SNNV...GNQG | AAWLQQHQGHPPKLLSY |

FIG. 17
CONTINUED

| CDR2-IMGT | FR3-IMGT | CDR3-IMGT | FR4-IMGT |
|---|---|---|---|
| ISA.NGNT | NYAQKLQ.GRVTMTDTSTSTAYMELRSLRSDDTAVYYC | ARDPGLWFGLTHDYYFDY | WGQGTLVTVSS |
| NSD.GSRT | NYADSVK.GRFTISRDNAKNTLYLQMNSLRAEDTAMYYC | ARGPGFFGFDI | WGQGTLVTVSS |
| INPV.NSRT | NYSPSFQ.GQVTISVDKSVTAVLQWSSLKASDTAMYYC | ARYYYAMEV | WGRGTLVTVSS |
| VDNN.NGNI | NYAQKFQ.GRVTMTDTSTSTAYMELRSLRSDDTAVYYC | ARGLFSSRWYLWFDP | WGQGTLVTVSS |
| LPN.FGST | NYAQKFQ.GRLTLADESTRTYLELNSLTSEDTAVYYC | ARGRDVAPSNSGFDV | WGQGTTVTVSS |

| CDR2-IMGT | FR3-IMGT | CDR3-IMGT | FR4-IMGT |
|---|---|---|---|
| RN...N | QRPSGVP.DRFSGSK.SGTASLAINGLQSEDEADYYC | AAWDDSRSGPV | FGGGTKLTVL |
| SN...N | QRPSGVP.QRFSGSR.SGTASLAISGLQSEDETDYYC | AAWDARLTGPL | FGGGTKLSL |
| RN...N | QRPSGVP.DRFSGST.SGTASLAISGLQSEDEADYYC | EAWDDSLNGPV | FGGGTKLTVL |
| EV...T | ERPSGVS.NRFSGSK.SGNTASLTISGLQAEDEGDYYC | SSYTRSSTSYVV | FGGGTKVTVL |
| RN...D | NRPSGIS.ERFSASR.SGNTASLTISGLQPEDEADYYC | SAYDRSLNAWV | FGGGTKLTVL |

FIG. 17
CONTINUED

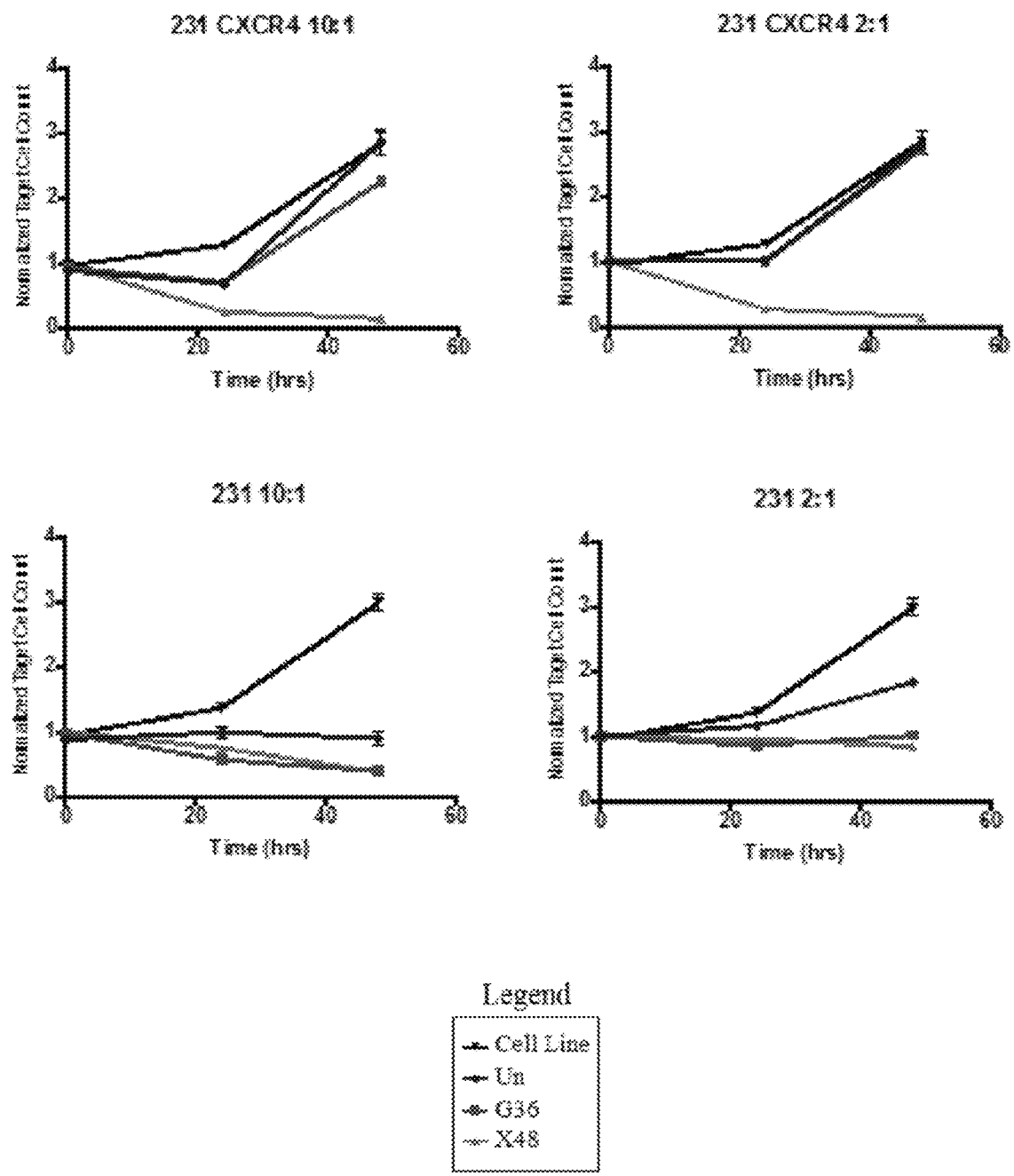
FIG. 20 CON'T

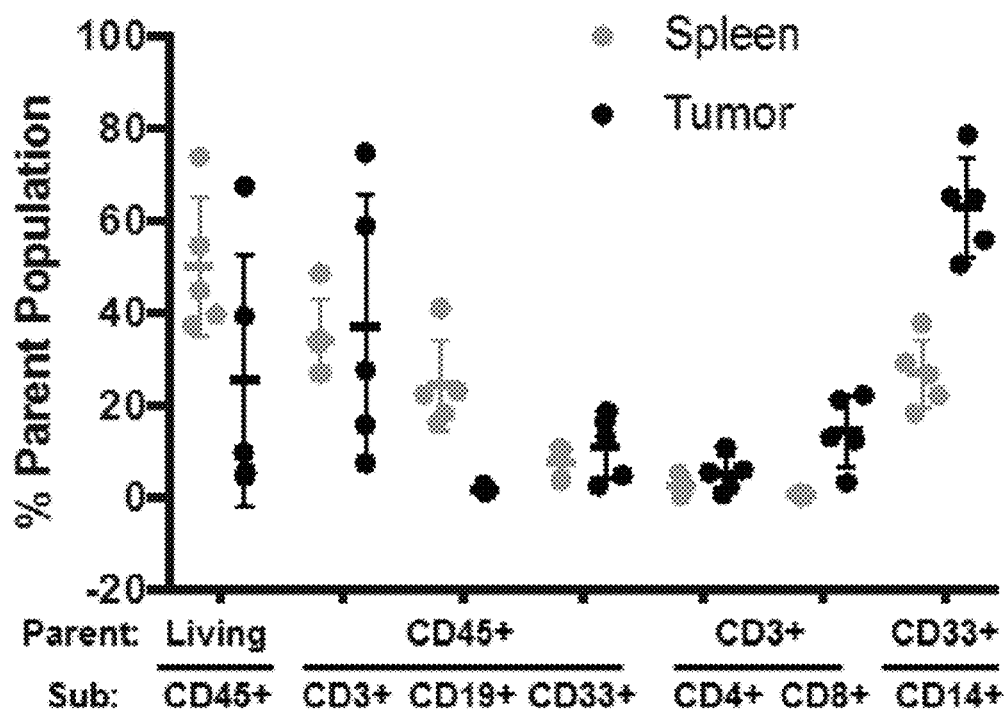
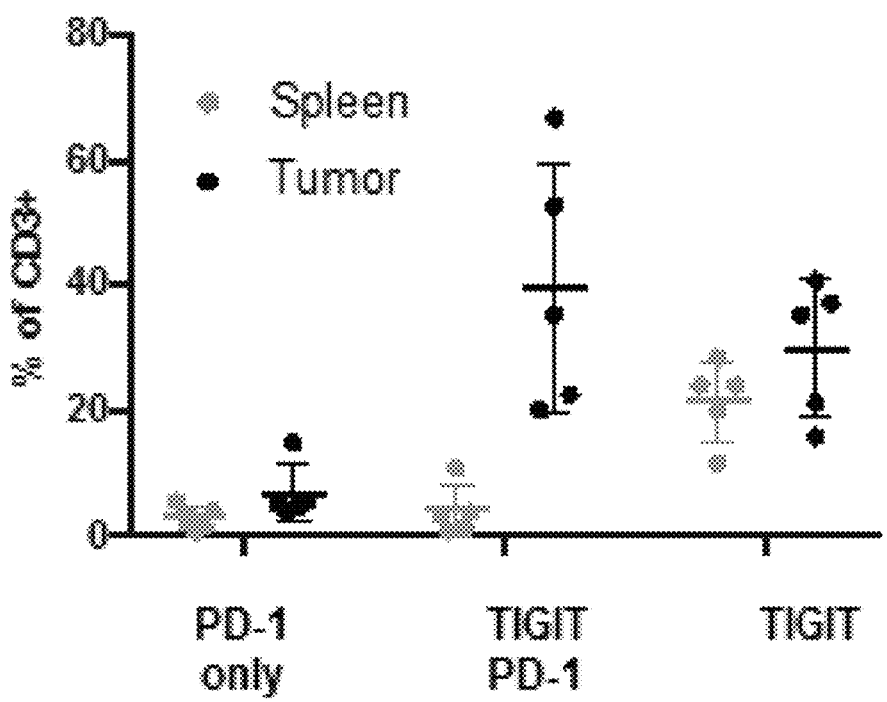
FIG. 22 CON'T

ENGINEERED CELLS, T CELL IMMUNE MODULATING ANTIBODIES AND METHODS FOR USING THE SAME

This application is a National Stage Entry of PCT/US2019/022272, filed on Mar. 14, 2019 which claims priority from U.S. Provisional Patent Application No. 62/643,040, filed on Mar. 14, 2018, and U.S. Provisional Patent Application No. 62/657,151, filed on Apr. 13, 2018, the contents of each of which are incorporated herein by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT INTERESTS

This invention was made with government support under Grant No. T32-CA207021 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 24, 2019, is named 5031461-043-WO1_SL.txt and is 79,055 bytes in size.

FIELD OF THE INVENTION

This invention is directed to engineered cells and methods for using the same. In embodiments, the engineered cell comprises a nucleic acid encoding a chimeric antigen receptor and a polypeptide, wherein the chimeric antigen receptor is specific for two or more antigens on the surface of a cancer cell, and wherein the polypeptide comprises an antibody or fragment thereof that can be secreted from the engineered cell.

BACKGROUND OF THE INVENTION

No targeted treatments exist for triple-negative breast cancer (TNBC), therefore chemotherapy remains the only treatment for patients. Immunotherapies like anti-PD-L1 had limited success (18% response rate) for TNBC, indicating that existing therapies are not an effective treatment.

SUMMARY OF THE INVENTION

Aspects of the invention are directed towards an engineered cell comprising a nucleic acid encoding a chimeric antigen receptor and a polypeptide.

In embodiments, the engineered cell is an engineered T cell. Non-limiting examples comprise a cytotoxic T cell (also known as TC, Cytotoxic T Lymphocyte, CTL, T-Killer cell, cytolytic T cell, CD8+ T-cells or killer T cell); CD4+ T cells; NK cells; and NKT cells In embodiments, the chimeric antigen receptor comprise an antigen-recognition domain and a signaling and/or stimulatory domain.

In embodiments, the antigen-recognition domain is specific for two or more antigens on the surface of a cell. For example, the cell is a cancer cell. For example, the antigens comprise C-X-C chemokine receptor type 4 and claudin-4. In embodiments, the chimeric antigen receptor (and/or antigen-recognition domain) comprises one or more antibody fragments. In embodiments, the chimeric antigen receptor comprises scFV. In embodiments, the chimerica antigen receptor comprises scFv directed to (targeted to) C-X-C chemokine receptor type 4 and claudin-4.

In embodiments, the signaling and/or stimulatory domain comprises CD28, 41BB, CD3-zeta intracellular signaling domains, or fragments thereof.

In embodiments, the polypeptide comprises an antibody or fragment thereof that can be secreted from the engineered cell. In embodiments, the secreted polypeptide modulates the immune system of a subject.

In embodiments, the polypeptide comprises an antibody or fragment thereof, such as a mini-body. Non-limiting examples of antibodies comprise monoclonal antibodies, polyclonal antibodies, multispecific antibodies (e.g., bispecific antibodies), humanized antibodies, fully human antibodies. In embodiments, the polypeptide comprises a monospecific antibody, a bispecific antibody, a trispecific antibody, or a multi-specific antibody. Non-limiting examples of antibody fragments comprise Fv, Fab, Fab', Fab'-SH, F(ab')2; diabodies; linear antibodies; single-chain antibody molecules (e.g. scFv); and multispecific antibodies formed from antibody fragments. In one embodiment, the invention comprise scFVs directed towards (and specific for) a target antigen.

In embodiments, the polypeptide is expressed from an expression construct separate than that which expresses the CAR, but which is a component of the same DNA vector as the CAR. In embodiments, the polypeptide is expressed from an expression construct separate than that which expresses the CAR, and which is a component of a different DNA vector as the CAR.

In embodiments, the constructs are cloned into one or more viral vectors. A non-limiting example comprises a lentiviral vector.

Aspects of the invention are further directed towards a method for treating a subject afflicted with cancer.

Aspects of the invention are still further directed towards a method of reducing progression or promoting regression of a cancer in a subject Still further, aspects of the invention are directed towards a method of reducing cellular proliferation of a cancer cell in a subject.

Further, aspects of the invention are directed towards a method of inducing cytotoxicity of a cell, preferably a cancer cell.

In embodiments, the method comprises administering to the subject a therapeutically effective amount of the engineered cell as described herein, such as an engineered T cell.

In other embodiments, the method comprises administering to the subject a therapeutically effective amount of a secreted polypeptide as described herein.

Non-limiting examples of cancer comprise carcinoma, lymphoma, blastoma, sarcoma, and leukemia. More particular examples of such cancers include squamous cell cancer, small cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

In embodiments, cancer comprises triple-negative breast cancer (TNBC).

Aspects of the invention are yet further directed towards a method for assessing the killing capability of engineered CAR T cells.

In embodiments, the method comprises obtaining cells from one or more types of cancer; admixing the cells with a dye, so as to stain the cells; seeding the cells in a multi-well plate; incubating the admixture for a period of time; adding different T cell types to the admixture to create a second admixture; co-culturing the second admixture for a period of time; and assessing the killing capability of the engineered CAR T cells. In embodiments, assessing comprises scanning and analyzing the plate. In embodiments, the plates can be analyzed using the bright field and blue fluorescent channels.

In embodiments, the cells comprise one or more types of cancer cells. In embodiments, the cells comprise one or more of cells isolated from the kidney (e.g., HEK293T cells), breast cancer cells (e.g., MDA-MB-231 cells, MDA-MB-468 cells, HCC38 cells), and kidney cancer cells (sk-rc-59 cells).

In embodiments the dy comprises ViaStain™ Tracer Blue dye.

In embodiments, the plate comprises a multi-well plate with 4-, 6-, 8-, 12-, 24-, 48- 96- or greater than 96 wells.

In embodiments, period of time refers to about 2 hours, 4 hours 6 hours, 8 hours, 12 hours, 16 hours, 24 hours, 36 hours, 48 hours, or longer than 48 hours.

Other objects and advantages of this invention will become readily apparent from the ensuing description.

BRIEF DESCRIPTION OF THE FIGURES

FIG. 12 is a table showing the tumor weight.

FIG. 13 shows the amino acid sequences of the following clones: 2N, 6R, X18, X19, X20, X33, and X48. The residues shown in bold represent the consensus amino acid sequence. In the consensus sequence, four or more clones having the same amino acid at a given position are designated as that amino acid. Framework Regions 1-4 (FW1-4), and Complementarity Determining Regions 1-3 (CDR1-3) for both the variable region of heavy chain ("VH") and the variable region of light chain ("VL") are shown for each clone. The VH and VL family designations are also provided.

FIG. 17 shows the amino acid sequences and germline alignment of anti-TIGIT antibodies (sol protein & PMPL) (SEQ ID NOS 102-131, respectively, in order of appearance).

DETAILED DESCRIPTION OF THE INVENTION

Figure 1:
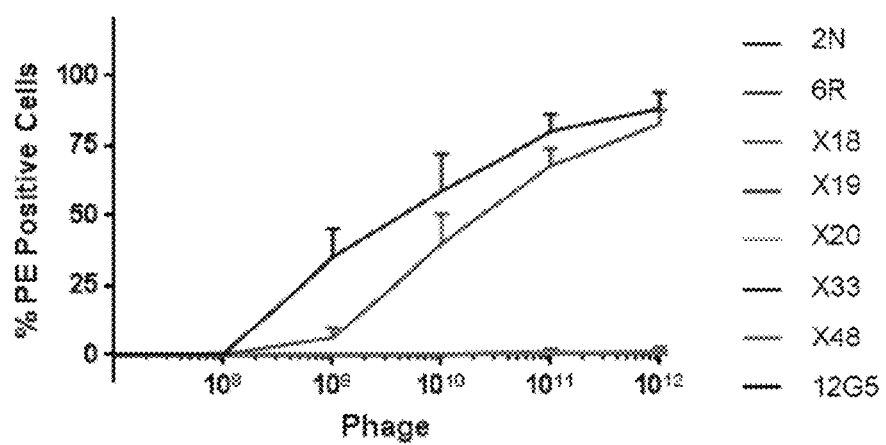
FIG. 1 shows anti-CXCR4 single-chain variable fragment expressing bacteriophage, 2N and 6R bind CXCR4 positive cells. Dilution series of CXCR-4-recognizing single-chain variable fragments (scFv), expressed as bacteriophage, binding to CXCR4-expressing stable HEK 293T cells. Binding was analyzed using flow cytometry analysis with a PE-anti-M13 bacteriophage secondary antibody. All scFvs, except 12G5, were discovered in the Marasco laboratory. 12G5 is a commercially available CXCR-4 recognizing antibody from a mouse hybridoma.

Triple-negative breast cancer (TNBC) is a highly aggressive subtype of breast cancer with poor clinical prognosis. While treated with chemotherapies, the high incidence of relapse signifies the need for novel, targeted therapies.

Chimeric-antigen receptor (CAR) T-cell therapies redirect a patient's T-cells to kill tumor cells by the exogenous expression of a CAR. A CAR can be a membrane spanning fusion protein that links the antigen recognition domain of an antibody to the intracellular signaling domains of the T-cell receptor and co-receptor. Solid tumors offer unique challenges for CAR-T therapies. Unlike blood cancers, tumor-associated target proteins are overexpressed between the tumor and healthy tissue resulting in on-target/off-tumor T-cell killing of healthy tissues. Furthermore, immune repression in the tumor microenvironment (TME) limits the activation of CAR-T cells towards killing the tumor.

The present invention relates to engineered chimeric antigen receptor (CAR) T-cell factories that secretes antibodies for TNBC. Without wishing to be bound by theory, a bispecific CAR targeting two antigens on the solid tumor, such as TNBC, will mitigate on-target/off-tumor T-cell killing, and that the secretion of a checkpoint blockade antibody will remove repression in the tumor microenvironment. Following local immune restoration, the CAR-T cells and other cells in the TME will work synergistically to shrink and clear tumors.

Abbreviations and Definitions

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Engineered CAR T Cells

Chimeric-antigen receptor (CAR) T-cell therapies redirect a patient's T-cells to kill tumor cells by the exogenous expression of a CAR. A CAR is a membrane spanning fusion protein that links the antigen recognition domain of an antibody or fragment to the intracellular signaling domains of the T-cell receptor and co-receptor. For example, chimeric antigen receptors fuse antigen-specific antibody fragments to T-cell co-stimulatory domains and the CD3 zeta intracellular signaling domain, allowing for the re-direction of T-cells towards an antigen presented on a cell of interest, for example, onto tumor cells.

The term "antibody" herein is used in the broadest sense and refers to immunoglobulin molecules and immunologically active portions of immunoglobulin (Ig) molecules, i.e., molecules that contain an antigen binding site that specifically binds (immunoreacts with) an antigen. "specifically binds" or "immunoreacts with" can refer to the antibody reacting with one or more antigenic determinants of the desired antigen and does not react with other polypeptides. Antibodies of the invention include, but are not limited to, polyclonal, monoclonal, humanized, fully human, bispecific, multispecific, chimeric, dAb (domain antibody), single chain antibodies, Fab, Fab' and F(ab')2 fragments, scFvs, diabodies, minibodies, scFv-Fc fusions, and Fab expression libraries. Unless specified to the contrary, any reference to "antibody" or "antibodies" made herein encompasses, for example, any (or all) of these molecules so long as they exhibit the desired antigen-binding activity.

A single chain Fv ("scFv") polypeptide molecule is a covalently linked VH:VL heterodimer, which can be expressed from a gene fusion including VH- and VL-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Bispecific antibodies refer to antibodies that have binding specificities for at least two different antigens. For example, bispecific antibodies can be monoclonal antibodies, such as human or humanized antibodies. In the present case, one of the binding specificities is CXCR4 and/or Claudin-4. The second binding target is any other antigen, and advantageously is a cell-surfaceprotein or receptor or receptor subunit. For example, one of the binding specificities is for CXCR4 and the second binding specificity is for claudin-4.

Bispecific antibodies can be prepared as full length antibodies or antibody fragments (e.g. F(ab')$_2$ bispecific antibodies). Methods for making bispecific antibodies are known in the art. See for example U.S. Pat. No. 8,329,178, which is incorporated herein by reference in its entirety.

In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Solid tumors offer unique challenges for CAR-T therapies. Unlike blood cancers, tumor-associated target proteins are overexpressed between the tumor and healthy tissue resulting in on-target/off-tumor T-cell killing of healthy tissues. Furthermore, immune repression in the tumor microenvironment (TME) limits the activation of CAR-T cells towards killing the tumor. Aspects of the invention address these problems. For example, embodiments comprise T cells comprising a bispecific CAR that (a) targets two antigens on a cancer cell to mitigate on-target/off-tumor T-cell killing, and (b) secretes a checkpoint blockade antibody that removes repression in the tumor microenvironment.

An emerging mechanism associated with the progression of tumors is the immune checkpoint pathway, which include cellular interactions that prevent excessive activation of T cells under normal conditions, allowing T cell function in a self-limited manner. As an evasion mechanism, many tumors are able to stimulate the expression of immune checkpoint molecules, resulting in an anergic phenotype of T cells that cannot restrain tumor progression. For example, emerging clinical data highlight the importance of one inhibitory ligand and receptor pair as an immune checkpoint: the programmed death-ligand 1 (PD-L1; B7-H1 and CD274) and programmed death receptor-1 (PD-1; CD279), in preventing killing of cancer cells by cytotoxic T-lymphocytes. PD1 receptor is expressed by many cell types like T cells, B cells, Natural Killer cells (NK) and host tissues. Tumors and Antigen-presenting cells (APC) expressing PD-L1 can block T cell receptor (TCR) signaling of cytotoxic T-lymphocytes through binding to receptor PD-1, decreasing the production of cytokines and T cell proliferation. PD-L1 overexpression can be found in many tumor types and may also mediate an immunosuppressive function through its interaction with other proteins, including CD80 (B7.1), blocking its ability to activate T cells through binding to CD28.

Genetic engineering of human lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the invention, there are lymphocytes (CARTS) that are modified to comprise at least a CAR, and in particular embodiments of the invention, a single CAR targets two or more antigens. In some embodiments, the CARTS are further modified to express and secrete one or more polypeptides, such as for example an antibody or a cytokine. Such CARTS are referred to herein as armed CARTS or CAR factories. Armed CARTS allow for simultaneous secretion of the polypeptide locally at the targeted site (i.e., tumor site).

A modified TCR called chimeric antigen receptor (CAR) containing single chain variable antibody fragment (scFv) previously selected by high affinity against a specific tumor associated antigen is a powerful new approach against cancer. The scFv presented in the CAR is linked to an intracellular signaling block that includes CD3ζ to induce T cell activation followed by antigen binding. This structure is characteristic for first-generation CARs, which were improved to second- and generation CARs that link the signaling co-stimulatory endodomains of CD28, 4-1BB, or OX40 to CD3 or $3^{rd}$-generation CARs that links two elements to CD3ζ in tandem. These endodomains are required for complete T cell activation during TCR recognition by antigen-presenting cells (APCs), improving cytokine production and proliferation of CAR-T cells. The effect of CART cells has heretofore been modest for the treatment of solid tumors, due to difficulty in finding unique tumor associated antigens, inefficient homing of T cells to tumor locations, low persistence of T cells in the body and the immunosuppressive microenvironment of solid tumors.

In particular cases, the lymphocytes can include a receptor that is chimeric, non-natural and engineered at least in part by the hand of man. In particular cases, the engineered chimeric antigen receptor (CAR) has one, two, three, four, or more components, and in some embodiments the one or more components facilitate targeting or binding of the lymphocyte to one or more tumor antigen-comprising cancer cells.

The CAR according to the invention generally comprises at least one transmembrane polypeptide comprising at least one extracellular ligand-biding domain and; one transmembrane polypeptide comprising at least one intracellular signaling domain; such that the polypeptides assemble together to form a Chimeric Antigen Receptor. Exemplary CARS useful in aspects of the invention include those disclosed in for example PCT/US2015/067225.

The term "extracellular ligand-binding domain" as used herein can refer to an oligo- or polypeptide that is capable of binding a ligand. The domain can be capable of interacting with a cell surface molecule. For example, the extracellular ligand-binding domain may be chosen to recognize a ligand that acts as a cell surface marker on target cells associated with a particular disease state.

Figure 2:
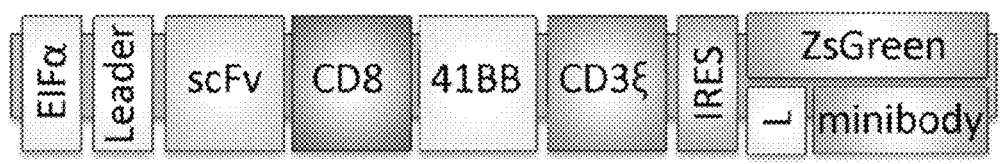
FIG. 2 shows specific cytotoxicity of CXCR-4 expressing cells by CXCR4-targeting chimeric antigen receptor T cells by measurement of target-cell adherence after CAR T-cell addition at 40 hours. A, Schematic diagram of CAR gene. A leader sequence targets the CAR through cell endoplasmic reticulum for membrane expression. Here, a monospecific scfv is fused to CD8 hinge, 41BB transmembrane and intracellular signaling domain and CD3 zeta signaling domain. In the second expression cassette either fluorescent molecule or immune-modulating minibody or antibody can be expressed. B,C Loss of target cell adherence due to CAR-T cell killing of MDA-MB-231 CXCR4 target cell line or MDA-MB-231 (no CXCR4), respectively. Controls include untransduced T-cells (un) and irrelevant CAR (G36) and target cells without T cells (black line) C, IFN-γ enzyme-linked immunosorbant assay (ELISA) measuring CAR-T cell activation in the presence of MDA-MB-231 (grey) and MDA-MB-231-CXCR4 expressing target cells (black) demonstrating specific activation of CAR-T cells only in presence of CXCR4 expressing target cells. Target cell/CAR description as above.
Figure 2:
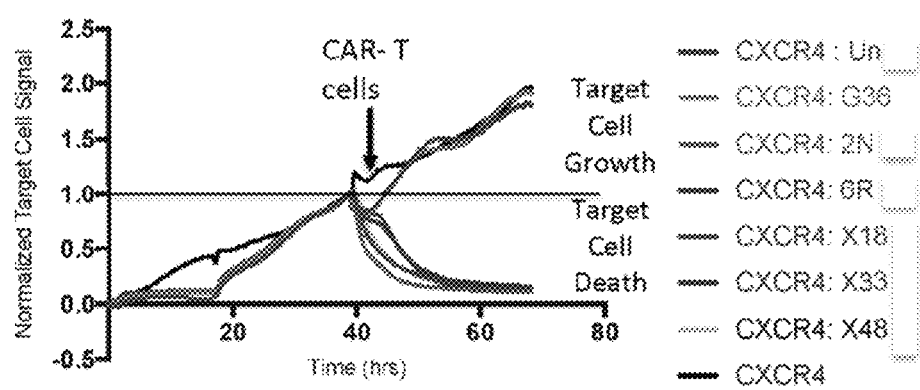

In particular, the extracellular ligand-binding domain can comprise an antigen binding domain or antigen recognition domain derived from an antibody against an antigen of the target. The antigen binding domain or antigen recognition domain can be an antibody fragment. An "antibody fragment" can be a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Referring to FIG. 2, for example, one embodiments comprises a CAR with an scFv as the antigen recognition domain.

The antigen recognition domain can be directed towards any antigen target of interest. In embodiments, the antigen target of interest is on the surface of a cell, such as the surface of a cancer cell. Non-limiting examples of antigen targets comprise C-X-C chemokine receptor type 4 (CXCR-4) and/or claudin-4.

As non limiting examples, the antigen of the target can be a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelia, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers.

In some embodiments, the CAR is specific for CXCR4 and/or claudin-4.

In embodiments, said extracellular ligand-binding domain is a single chain antibody fragment (scFv) comprising the light ($V_L$) and the heavy ($V_H$) variable fragment of a target antigen specific monoclonal antibody joined by a flexible linker. For example, the scFv antibody is specific for CXCR4 and/or claudin-4.

Non-limiting examples of antibodies useful in constructing the CAR according to the invention includes antibodies disclosed in for example: WO/2005/060520, WO/2006/089141, WO/2007/065027, WO/2009/086514, WO/2009/079259, WO/2011/153380, WO/2014/055897, WO 2015/143194, WO 2015/164865, WO 2013/166500, and WO 2014/144061; PCT/US2015/054202, PCT/US2015/054010, PCT/US2015/067225, and PCT/US2016/026800, the contents of which are hereby incorporated by reference in their entireties.

The antigen recognition domain useful in constructing the CAR-Ts, for example scFVs directed toward C-X-C chemokine receptor type 4 (CXCR-4) and/or claudin-4, can be synthesized, engineered, and/or produced using nucleic acids (e.g., DNA). The DNA encoding the antigen recognition domain can be cloned in frame to DNA encoding necessary CAR-T elements such as, but not limited to, CD8 hinge regions, transmembrane domains, co-stimulatory domains of molecules of immunological interest such as, but not limited to, CD28 and 41BB and CD3-zeta intracellular signaling domains. See FIG. 2, for example.

CXCR4

Figure 14:
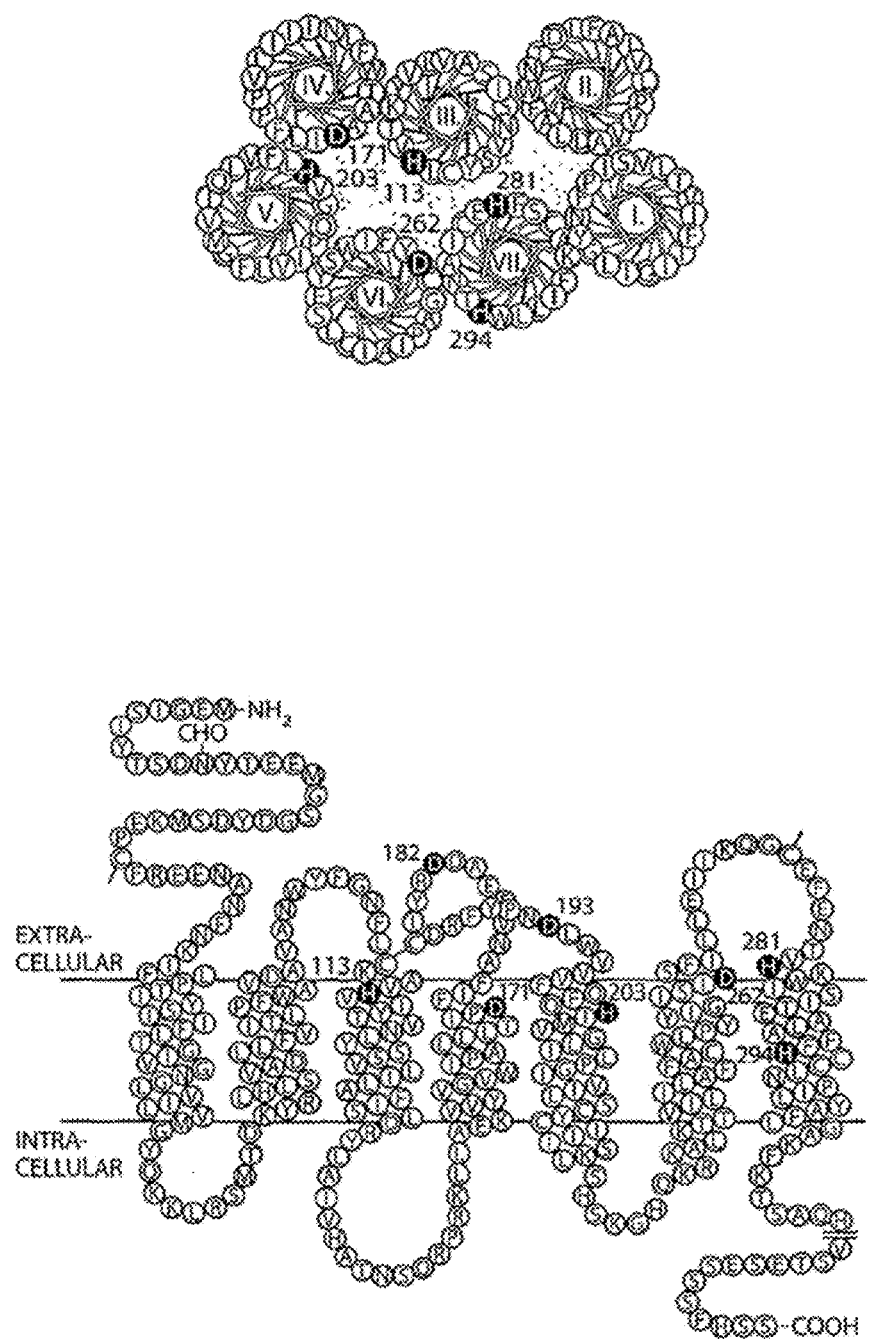
FIG. 14 is a schematic showing the amino acid sequence of the human CXCR4 receptor (SEQ ID NO: 95). Also provided are helical wheel (TOP) and serpentine diagrams (BOTTOM) of the human CXCR4 receptor.

Chemokine (C-X-C motif) receptor 4 ("CXCR4") (also known as fusin, LESTR, or HUMSTR) is a G protein-coupled, 7-transmembrane domain chemokine receptor that is normally embedded within the membrane of a cell. CXCR4 is one of the best-characterized chemokine receptors. The 352 amino acid sequence (along with helical wheel and serpentine diagrams) of the human CXCR4 receptor is shown in FIG. 14 (Top and Bottom panels). As shown in FIG. 14, bottom panel, CXCR4 is characterized by four different extracellular regions: the N terminal domain, ECL1, ECL2, and ECL3.

CXCR4 is expressed at least in dendritic cells; naïve, non-memory T-cells; regulatory T cells; neurons and microglia; fresh primary monocytes; endothelial cells; neutrophils and B-cells; tumor cells, including but not limited to breast cancer cells, renal cell carcinoma cells, non-small cell lung cancer cells, prostate cancer cells, and glioblastoma cells; and CD34+ hematopoietic stem cells. CXCR4 is essential for leukocyte trafficking; chemotaxis; B cell lymphopoiesis and myelopoiesis; stem cell migration; tumor or cancer cell metastasis; tumor cell angiogenesis; gastrointestinal tract vascularization; neuronal and germ cell migration; and X4-tropic HIV invasion of host cells. (See Li et al., Cancer Cell 6:459-69 (2004); Hernandez et al., Nat. Genet. 34:70-74 (2003); Nagasawa et al., Nature 382:635-38 (1996); Knaut et al., Nature 421:279-82 (2003); Kunwar et al., Nature 421:226-27 (2003); Connor et al., J. Exp. Med. 185:621-28 (1997); and Scarlatti et al., Nat. Med. 3:1259-65 (1997)).

The alpha-chemokine stromal cell-derived factor (SDF-1) (also known as CXCL12) is the natural ligand for CXCR4. SDF-1α is the only chemokine that has just one chemokine receptor. (See Imitola et al., Proc. Natl. Acad. Sci. USA 101(52):18117-22 (2004); Lu et al., Proc. Natl. Acad. Sci. USA 99:2090-95 (2002). SDF-1 binding to CXCR4 activates multiple pathways that function to regulate cell invasion and migration. (See Benovic et al., Cancer Cell 6:429-30 (2004)). For example, in response to binding its ligand, CXCR4 triggers the migration and recruitment of immune cells. Additionally, this ligand-receptor pair may also play a role in the development of the nervous system. SDF-1 binding to CXCR4 also plays an important role in hematopoiesis and organogenesis. (See Nagasawi et al., Nature 382:635 (1996)). CXCR4 is also recognized by an antagonistic chemokine, the viral macrophage inflammatory protein II (vMIP-II) encoded by human herpesvirus type III. (See, Zhou et al., 9th Conference on Retroviruses and Opportunistic Infections, Session 39 Poster Session, Abstract 189-M (2002)).

Embodiments of the present invention can comprise anti-CXCR4 antibodies. Exemplary anti-CXCR4 antibodies include those described in U.S. Pat. No. 8,329,178, which is incorporated herein by reference in its entirety.

Figure 13:
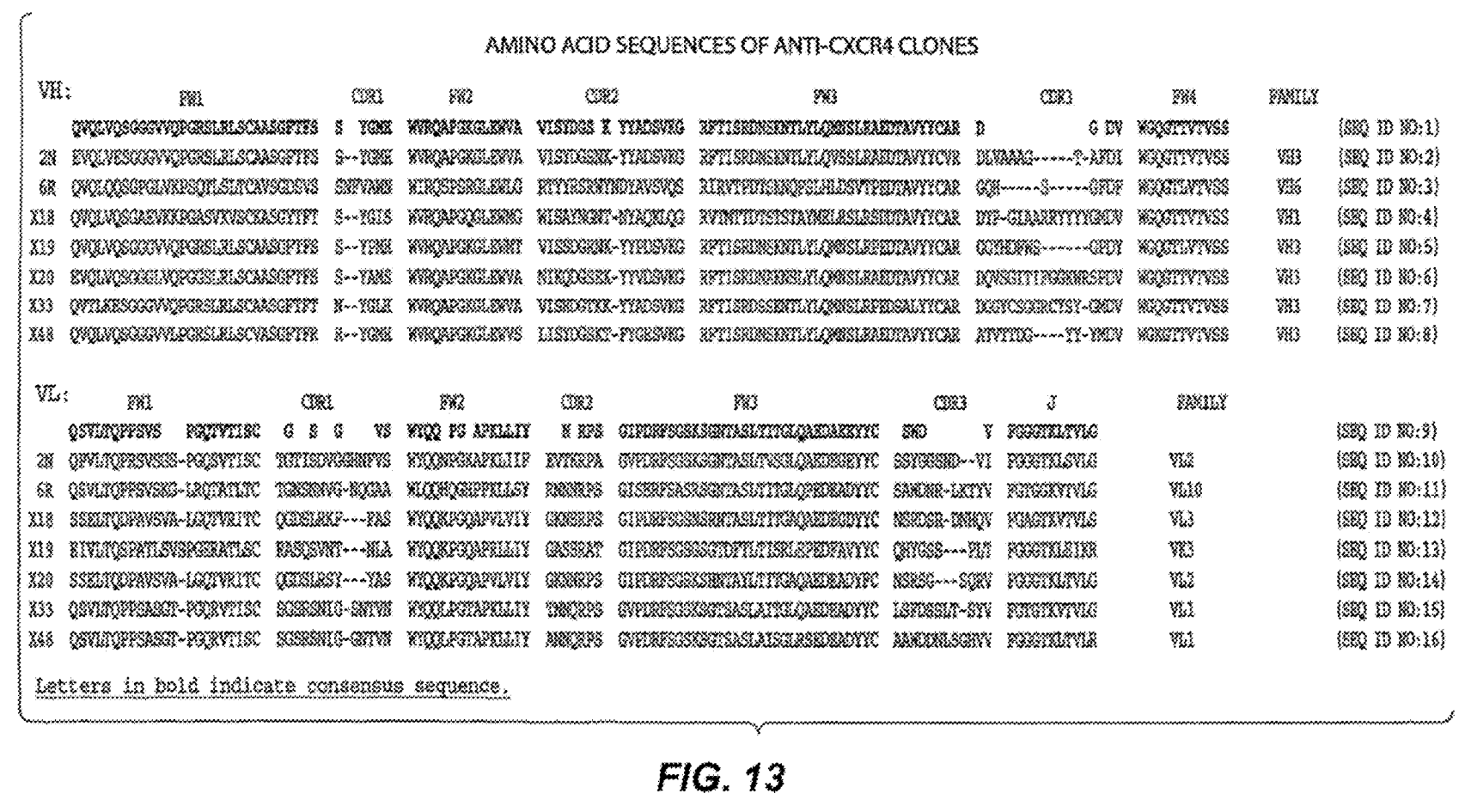

For example, anti-CXCR4 antibodies can comprise mAb18, mAb 19, mAb 20, mAB 33, mAB 48, mAb2N, or mAb 6R. The amino acid sequences of the VH and VL regions of mAb 18, mAb 19, mAb 20, mAb 33, mAb 48, mAb 2N, and mAb 6R are provided in FIG. 13. FIG. 13 also provides a consensus sequence (e.g., bolded letters; see also U.S. Pat. No. 8,329,178, which is incorporated herein by reference in its entirety). In this consensus, when four or more clones have the same amino acid at a given position, that position in the consensus is designated by that amino acid. The anti-CXCR4 antibody can also comprise 12G5. 12G5 is a commercially available CXCR-4 recognizing antibody from a mouse hybridoma.

As shown in FIG. 13, CDR1 of the VH region of the mAb 2N heavy chain has the sequence: SYGMH (SEQ ID NO:17); CDR2 of the VH region of the mAb 2N heavy chain has the sequence: VISYDGSNKYYADSVKG (SEQ ID NO:18); CDR3 of the VH region of the mAb 2N heavy chain has the sequence: DLVAAAGTAFDI (SEQ ID NO:19); CDR1 of the VL region of the mAb 2N light chain has the sequence TGTISDVGGHNFVS (SEQ ID NO:20); CDR2 of the VL region of the mAb 2N light chain has the sequence: EVTKRPA (SEQ ID NO:21); and CDR3 of the VL region of the mAb 2N light chain has the sequence: SSYGGSNDVI (SEQ ID NO:22).

Moreover, as shown in FIG. 13, CDR1 of the VH region of the mAb 6R heavy chain has the sequence: SNFVAWN (SEQ ID NO:23); CDR2 of the VH region of the mAb 6R heavy chain has the sequence: RTYYRSRWYN-DYAVSVQS (SEQ ID NO:24); CDR3 of the VH region of the mAb 6R heavy chain has the sequence: GQHSGFDF (SEQ ID NO:25); CDR1 of the VL region of the mAb 6R light chain has the sequence TGNSNNVGNQGAA (SEQ ID NO:26); CDR2 of the VL region of the mAb 6R light chain has the sequence: RNNNRPS (SEQ ID NO:27); and CDR3 of the VL region of the mAb 6R light chain has the sequence: SAWDNRLKTYV (SEQ ID NO:28).

As also shown in FIG. 13, CDR1 of the VH region of the mAb 18 heavy chain has the sequence: SYGIS (SEQ ID NO:29); CDR2 of the VH region of the mAb 18 heavy chain has the sequence: WISAYNGNTNYAQKLQG (SEQ ID NO:30); CDR3 of the VH region of the mAb 18 heavy chain has the sequence: DTPGIAARRYYYYGMDV (SEQ ID NO:31); CDR1 of the VL region of the mAb 18 light chain has the sequence QGDSLRKFFAS (SEQ ID NO:32); CDR2 of the VL region of the mAb 18 light chain has the sequence:

GKNSRPS (SEQ ID NO:33); and CDR3 of the VL region of the mAb 18 light chain has the sequence: NSRDSRDNHQV (SEQ ID NO:34).

Similarly, as shown in FIG. 13, CDR1 of the VH region of the mAb 19 heavy chain has the sequence: SYPMH (SEQ ID NO:35); CDR2 of the VH region of the mAb 19 heavy chain has the sequence: VISSDGRNKYYPDSVKG (SEQ ID NO:36); CDR3 of the VH region of the mAb 19 heavy chain has the sequence: GGYHDFWSGPDY (SEQ ID NO:37); CDR1 of the VL region of the mAb 19 light chain has the sequence RASQSVNTNLA (SEQ ID NO:38); CDR2 of the VL region of the mAb 19 light chain has the sequence: GASSRAT (SEQ ID NO:39); and CDR3 of the VL region of the mAb 19 light chain has the sequence: QHYGSSPLT (SEQ ID NO:40).

As shown in FIG. 13, CDR1 of the VH region of the mAb 20 heavy chain has the sequence: SYAMS (SEQ ID NO:41); CDR2 of the VH region of the mAb 20 heavy chain has the sequence: NIKQDGSEKYYVDSVKG (SEQ ID NO:42); CDR3 of the VH region of the mAb 20 heavy chain has the sequence: DQVSGITIFGGKWRSPDV (SEQ ID NO:43); CDR1 of the VL region of the mAb 20 light chain has the sequence QGDSLRSYYAS (SEQ ID NO:44); CDR2 of the VL region of the mAb 20 light chain has the sequence: GKNNRPS (SEQ ID NO:45); and CDR3 of the VL region of the mAb 20 light chain has the sequence: NSRSGSQRV (SEQ ID NO:46).

Moreover, CDR1 of the VH region of the mAb 33 heavy chain has the sequence: NYGLH (SEQ ID NO:47); CDR2 of the VH region of the mAb 33 heavy chain has the sequence: VISHDGTKKYYADSVKG (SEQ ID NO:48); CDR3 of the VH region of the mAb 33 heavy chain has the sequence: DGGYCSGGRCYSYGMDV (SEQ ID NO:49); CDR1 of the VL region of the mAb 33 light chain has the sequence SGSRSNIGSNTVN (SEQ ID NO:50); CDR2 of the VL region of the mAb 33 light chain has the sequence: TNNQRPS (SEQ ID NO:51); and CDR3 of the VL region of the mAb 33 light chain has the sequence: LSFDSSLTSYV (SEQ ID NO:52).

Likewise, as also shown in FIG. 13, CDR1 of the VH region of the mAb 48 heavy chain has the sequence: RYGMH (SEQ ID NO:53); CDR2 of the VH region of the mAb 48 heavy chain has the sequence: LISYDGSKTFYGESVKG (SEQ ID NO: 54); CDR3 of the VH region of the mAb 48 heavy chain has the sequence: ATVTTDGYYYMDV (SEQ ID NO: 55); CDR1 of the VL region of the mAb 48 light chain has the sequence SGSRSNIGGNTVN (SEQ ID NO:56); CDR2 of the VL region of the mAb 48 light chain has the sequence: ANNQRPS (SEQ ID NO: 57); and CDR3 of the VL region of the mAb 48 light chain has the sequence: AAWDDNLSGHVV (SEQ ID NO: 58).

In embodiments, the anti-CXCR4 antibody can comprise a heavy chain with a VH comprising a CDR1 of SEQ ID NO: 17, 23, 29, 35, 41, 47, or 53; a CDR2 of SEQ ID NO: 18, 24, 30, 36, 42, 48, or 54; and a CDR3 of SEQ ID NO: 19, 25, 31, 37, 43, 49, or 55; or any combination thereof.

In embodiments, the anti-CXCR4 antibody can comprise a light chain with a VL comprising a CDR1 of SEQ ID NO: 20, 26, 32, 38, 44, 50, or 56; a CDR2 of SEQ ID NO: 21, 27, 33, 39, 45, 51, or 57; and a CDR3 of SEQ ID NO: 22, 28, 34, 40, 46, 52, or 58; or any combination thereof.

The invention also encompasses single chain antibodies. For example, the invention encompasses scFvs 18, 19, 20, 33, 48, 2N, and 6R as well as any other scFvs identified according to the methods disclosed herein.

Claudin-4

Claudins are transmembrane proteins that belong to the multigene adhesion molecule family and are found in cellular tight junctions. These proteins are considered to be responsible for the establishment of a paracellular barrier that controls the flow of molecules across the intracellular spaces of the epithelium. Claudins are believed to regulate cell proliferation and differentiation because they also bind cell-signaling ligands. There are ~24 known claudins that have a tissue-specific expression pattern and any change in their pattern or distribution has been suggested to have a role in the pathology of various disorders, including cancer. Gene expression profiling showed that claudin 4 was overexpressed in pancreatic duct adenocarcinoma, and it is also expressed in normal tissues of the breast, ovaries, prostate, bladder, and gastrointestinal mucosa. However, because the level of expression of this protein is significantly higher in primary and metastatic pancreatic cancers, the possible use of claudin 4 as an early marker or therapeutic target for imaging of this cancer was suggested. See [$^{125}$I]Anti-claudin 4 monoclonal antibody from The MICAD Research Team; Jun. 28, 2007.

Figure 15:
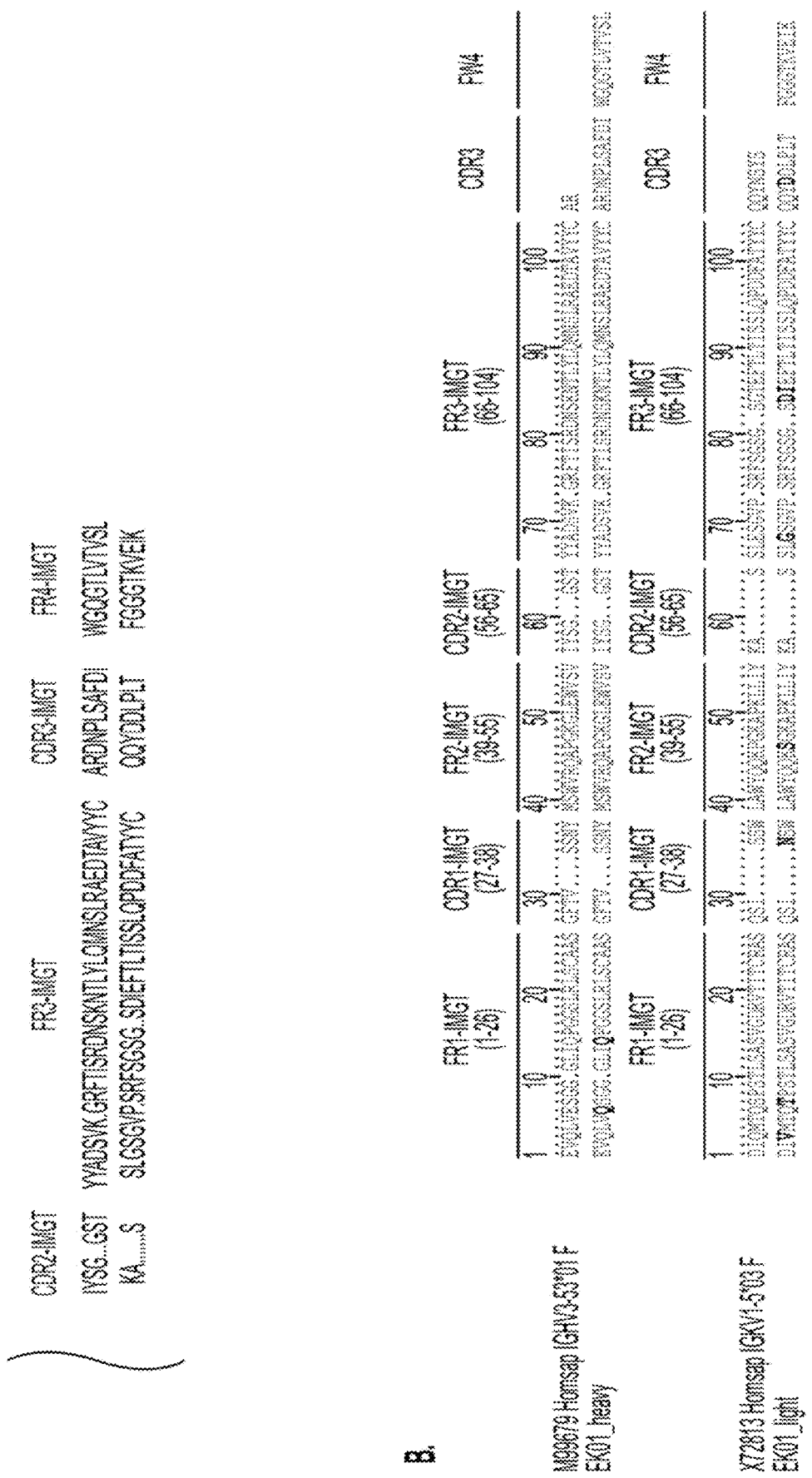
FIG. 15 shows the amino acid sequences of the anti-CLDN4 clone EK01. Panel A shows the amino acid sequence of the anti-CLDN4 clone EK01 (SEQ ID NOS 96 and 97, respectively, in order of appearance). Panel B shows the amino acid sequence of anti-CLDN4 clone EK01 with germline comparison (SEQ ID NOS 98-101, respectively, in order of appearance).

As shown in FIG. 15, CDR1 of the VH region of the EK01 heavy chain has the sequence GFTV . . . SSNY (SEQ ID NO: 59); CDR2 of the VH region has the sequence IYSG . . . GST (SEQ ID NO: 60); and CDR3 of the VH region has the sequence ARDNPLSAFDI (SEQ ID NO: 61); CDR1 of the VL region of the EK01 light chain has the sequence QSI . . . NSW (SEQ ID NO: 62); CDR2 of the VL region has the sequence KA . . . S (SEQ ID NO: 63); and CDR3 of the VL region has the sequence QQYDDLPLT (SEQ ID NO: 64).

Other binding domain than scFv can also be used for predefined targeting of lymphocytes, such as camelid single-domain antibody fragments or receptor ligands, antibody binding domains, antibody hypervariable loops or CDRs as non limiting examples.

In a preferred embodiment said transmembrane domain further comprises a stalk region between said extracellular ligand-binding domain and said transmembrane domain. The term "stalk region" used herein can mean any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In an embodiment said stalk region is a part of human CD8 alpha chain The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" can refer to the portion of a protein which transduces the effector signal function signal and directs the cell to perform a specialized function.

Signal transduction domain can comprise two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCR zeta, FcR gamma, FcR beta, FcR epsilon, CD3 gamma, CD3 delta, CD3 epsilon, CD5, CD22, CD79a, CD79b and CD66d. In a preferred embodiment, the signaling transducing domain of the CAR can comprise the CD3 zeta signaling domain, or the intracytoplasmic domain of the Fc epsilon RI beta or gamma chains. In another preferred embodiment, the signaling is provided by CD3 zeta together with co-stimulation provided by CD28 and a tumor necrosis factor receptor (TNFr), such as 4-1BB or OX40), for example.

In an embodiment the intracellular signaling domain of the CAR of the present invention comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

"Co-stimulatory ligand" can refer to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" can refer to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

Chimeric antigen receptors fuse antigen-recognition domains to signaling domains (also referred to as stimulatory domains) that modulate (i.e., stimulate) cell signaling. Non-limiting examples of such stimulatory domains comprise those of CD28, 41BB, and/or CD3-zeta intracellular signaling domains. See FIG. 2, for example.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein can refer to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon .gamma., GM-CSF, IL-3, IL-4 production thus effected.

Cells

Embodiments of the invention include cells that express a CAR (i.e, CARTS). The cell may be of any kind, including an immune cell capable of expressing the CAR for cancer therapy or a cell, such as a bacterial cell, that harbors an expression vector that encodes the CAR. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T-cells or killer T cell); NK cells and NKT cells are also encompassed in the invention.

Some vectors can employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

Armed CARTS

The invention further includes CARTs that are modified to secrete one or more polypeptides. Such CARTs can be refered to as CART factories or armed CARTs. The polypeptide can be, for example, an antibody or fragment thereof as described herein. For example, the polypeptide can be an antibody or cytokine. In embodiments, the antibody is specific for TIGIT, CAIX, GITR, PD-L1, PD-L2. PD-1, or CCR4.

For example, a second expression construct, which can be in the same DNA vector as that which encodes the CAR (e.g. the antigen-recognition domain) or in a second separate vector, can be used to encode a mini body (scFv-Fc) or antibody, or a fragment thereof, that is directed against a single or multiple antigens of interest, and can be cloned after an internal ribosomal entry site (IRES). Refering to FIG. 2, the second expression cassette comprises either a fluorescent molecule or an immune-modulating minibody.

Figure 6:
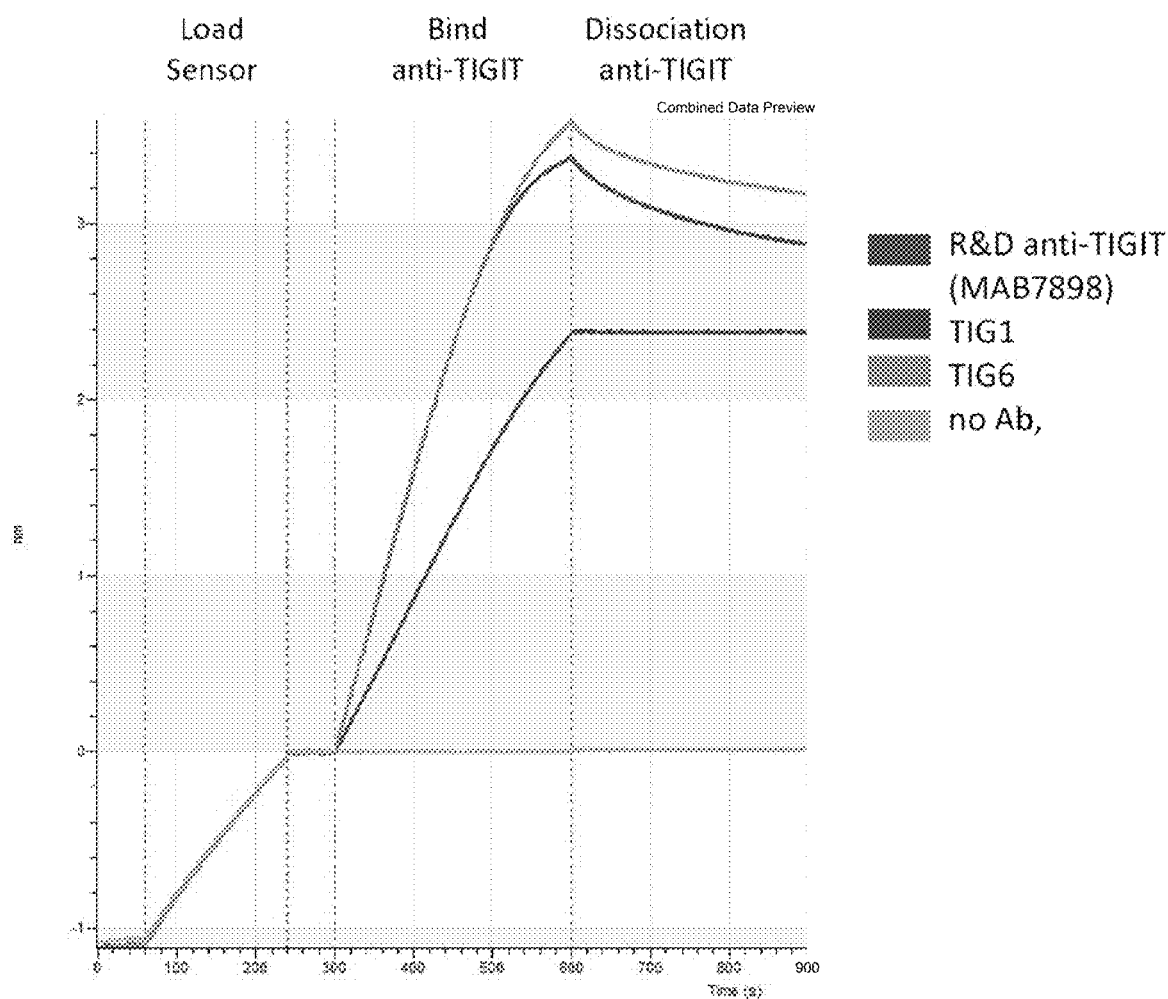
Figure 7:
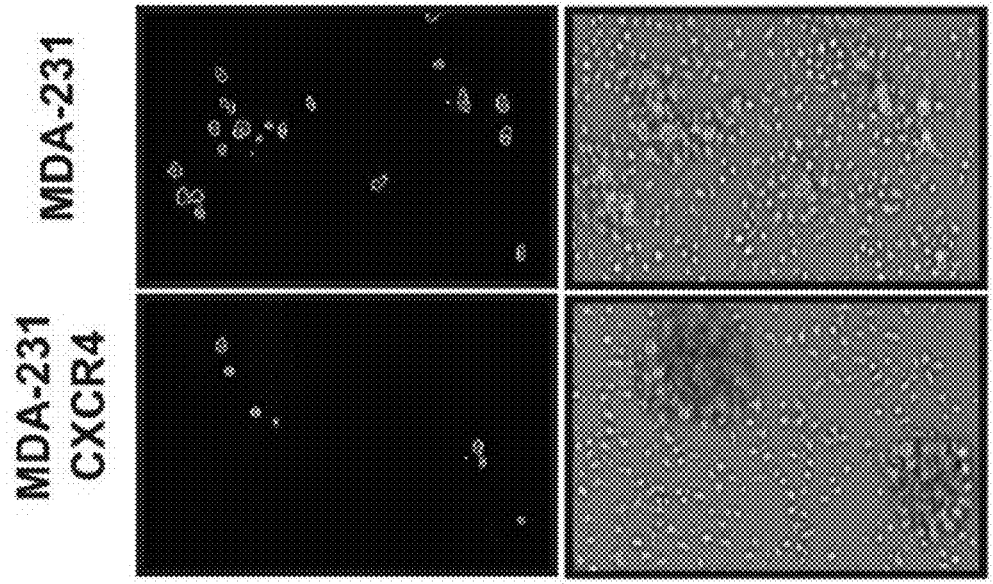
Figure 8:
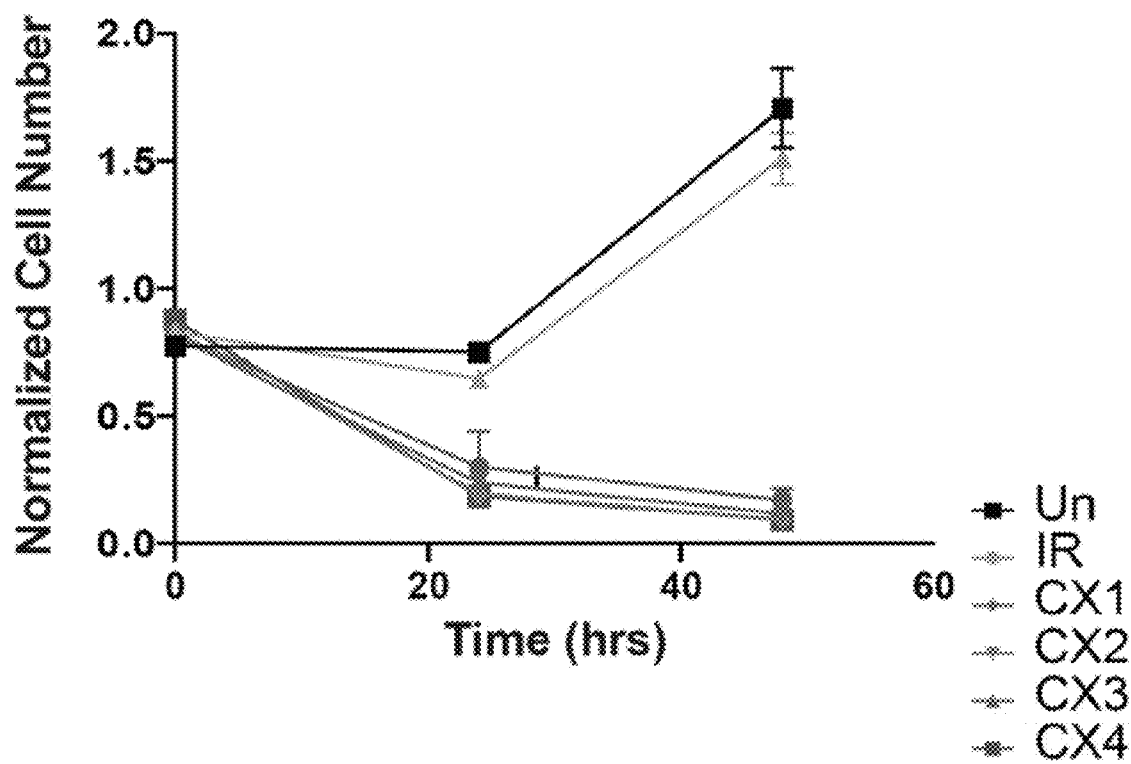
Figure 8:
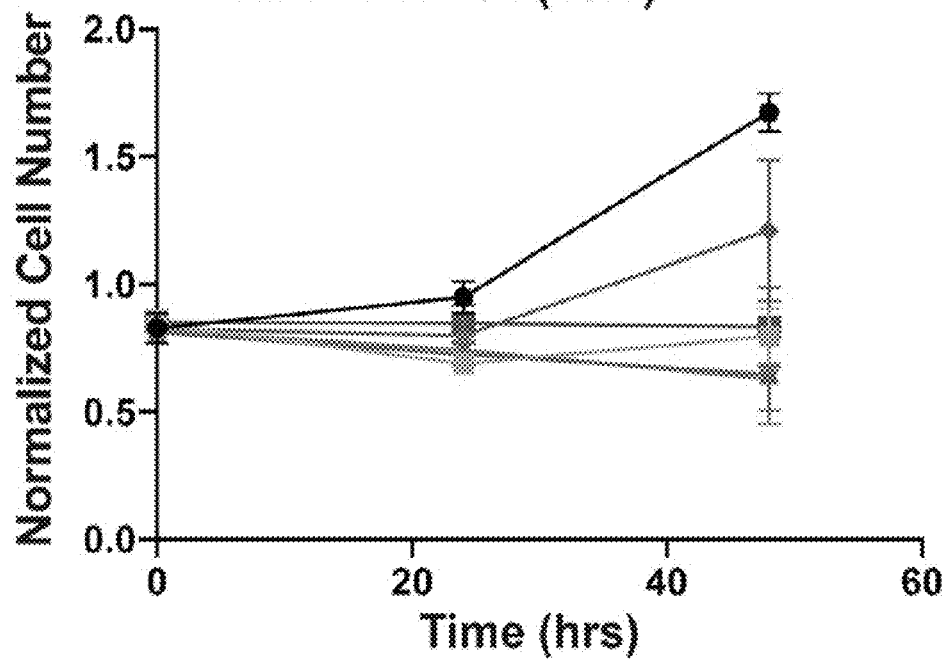
Figure 9:
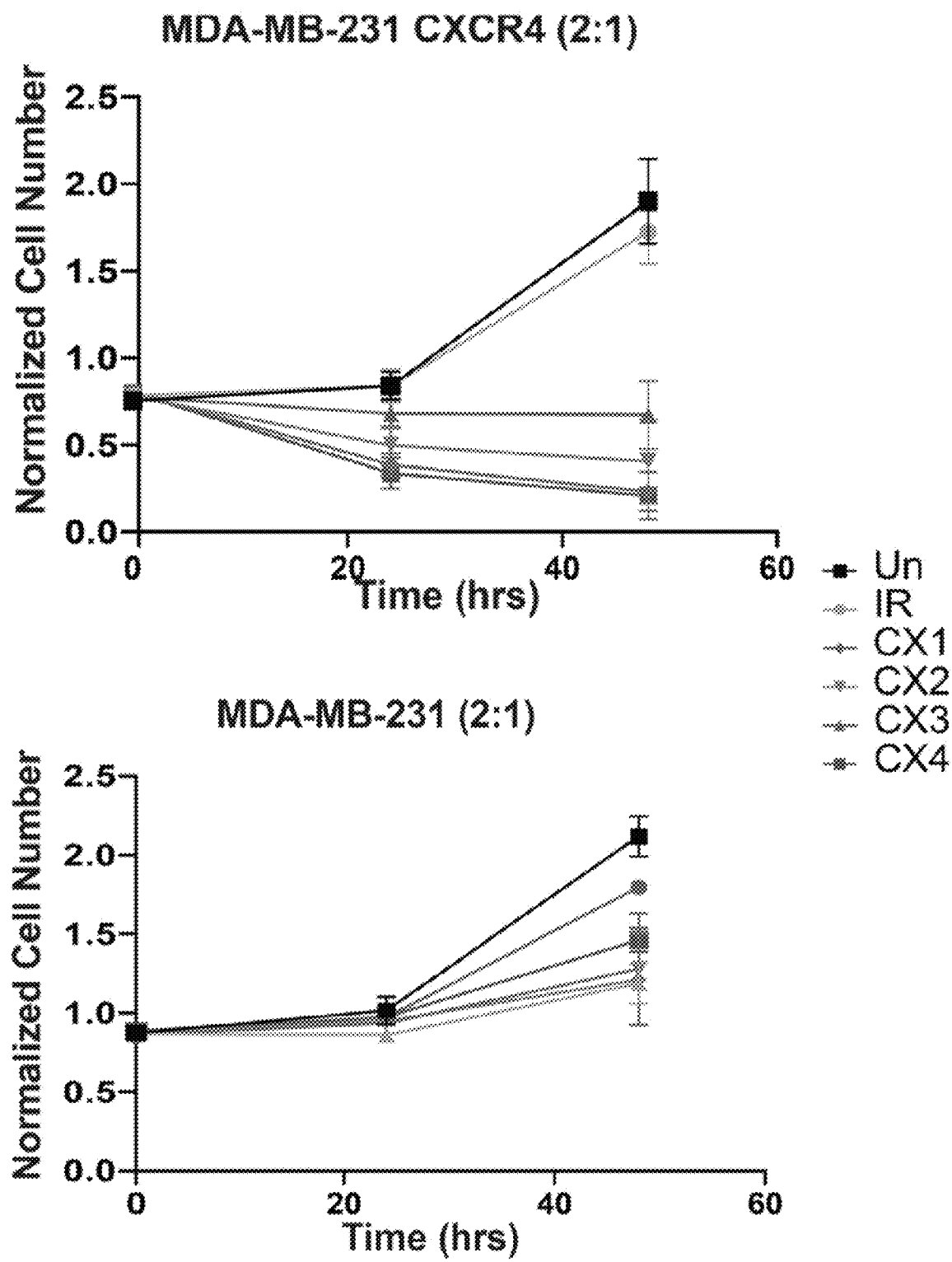
Figure 10:
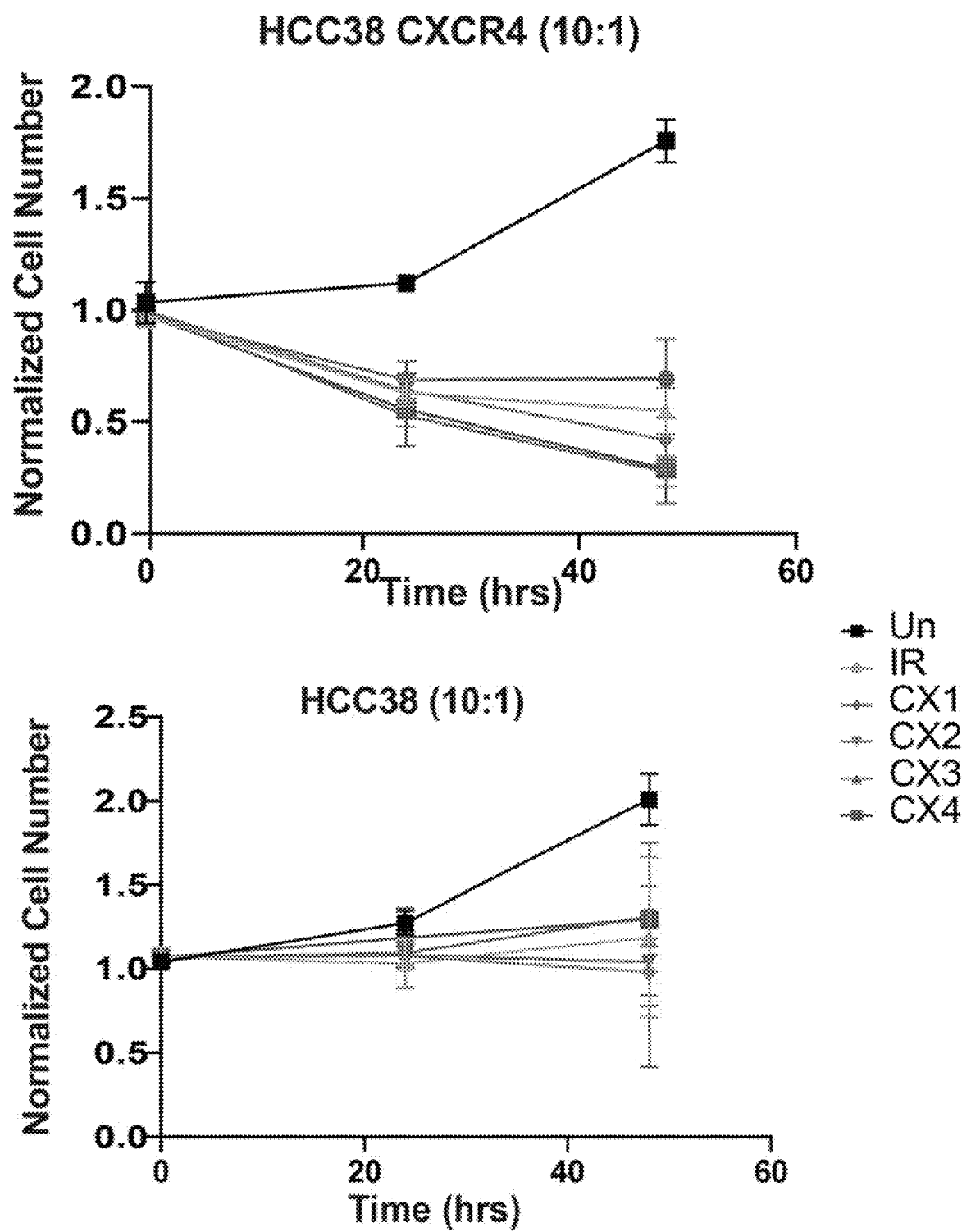
Figure 11:
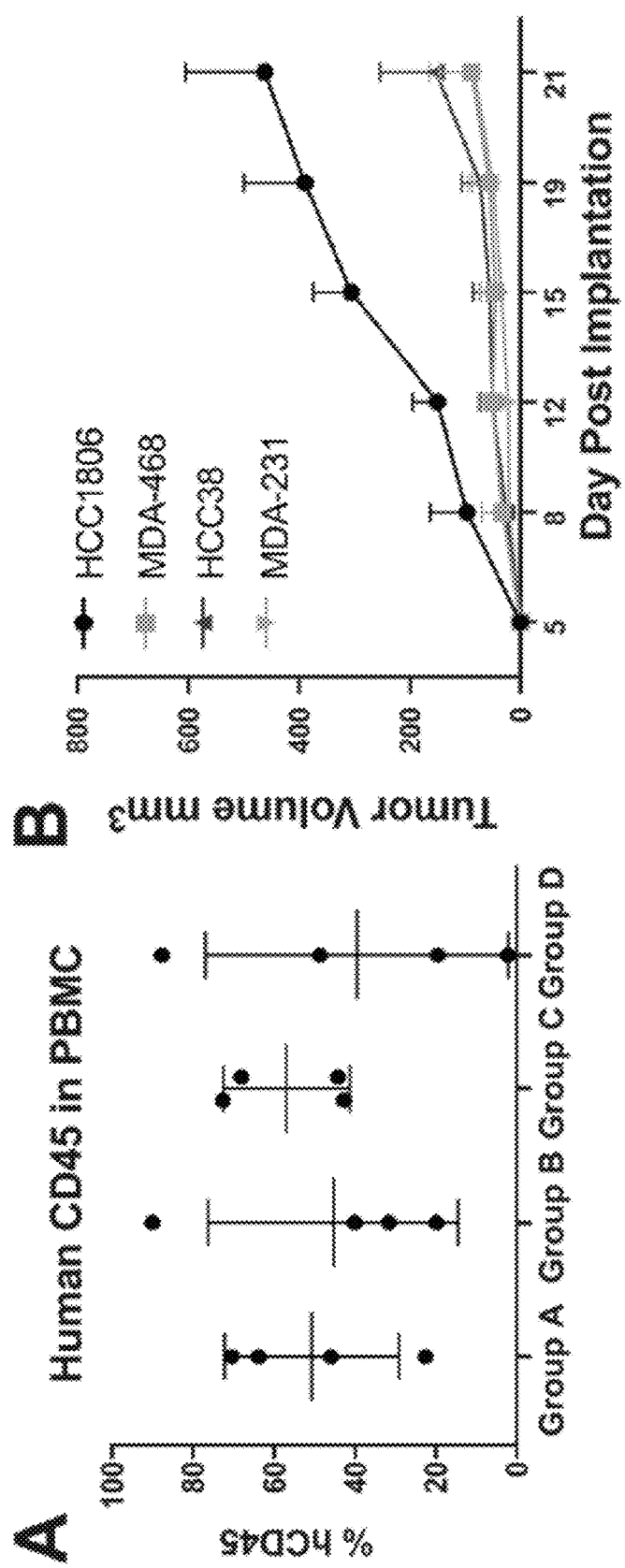
FIG. 11E is a graph showing the percentage of CD3+ myeloid cells of CD45+ parent population.
Figure 16:
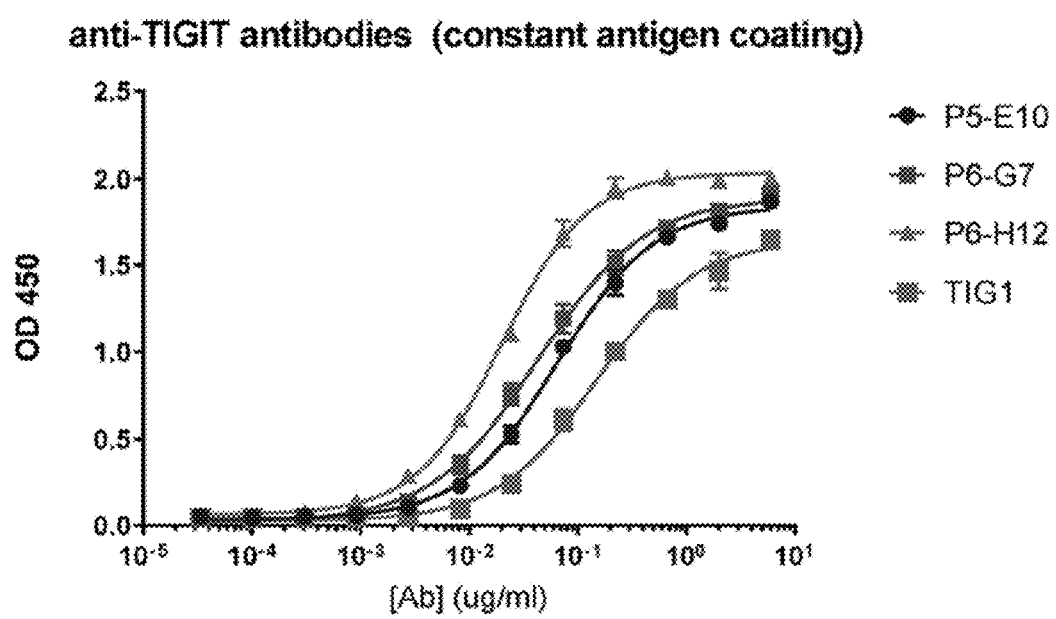
FIG. 16 shows the identification of three additional anti-TIGIT antibodies from new PMPL panning as determined by ELISA assay. ELISA plates were coated with 1 μg/ml soluble PD1 for 2 hours at 37° C. The plates were then washed and blocked with 2% BSA/PBS at 37° C. for 1 hour. The blocking solution was removed and 3× serial dilutions of the antibodies were added to each well (100 μl), starting with 6 μg/ml. The plates were then incubated at RT with gentle shaking, washed 6× with PBS-T, and the secondary anti-human Fc-HRP (1:150 k, Bethyl) was added. The plates were again incubated at room temperature with gentle shaking for 1 hour before being washed 6× with PBS-T. TMB substrate was added and the plate was incubated at 30° C. for 10 min to accelerate the HRP reaction. The signal was then quenched with TMB stop solution and read at 450 nm. Samples P5-E10 and P6-G7 were run in quadrupicate and P6-G7 and TIG1 were run in triplicate.
Figure 17:
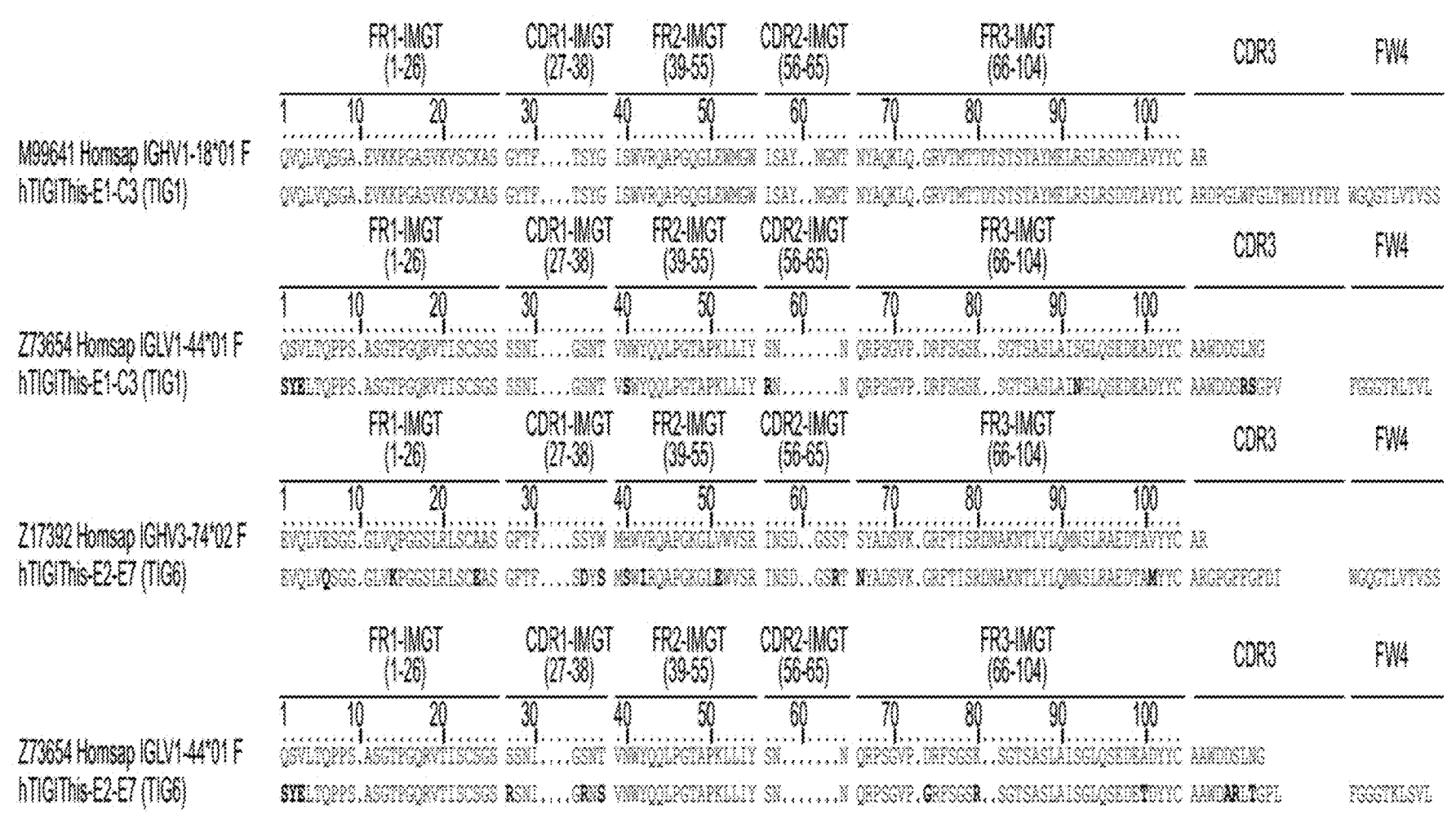
Figure 17:
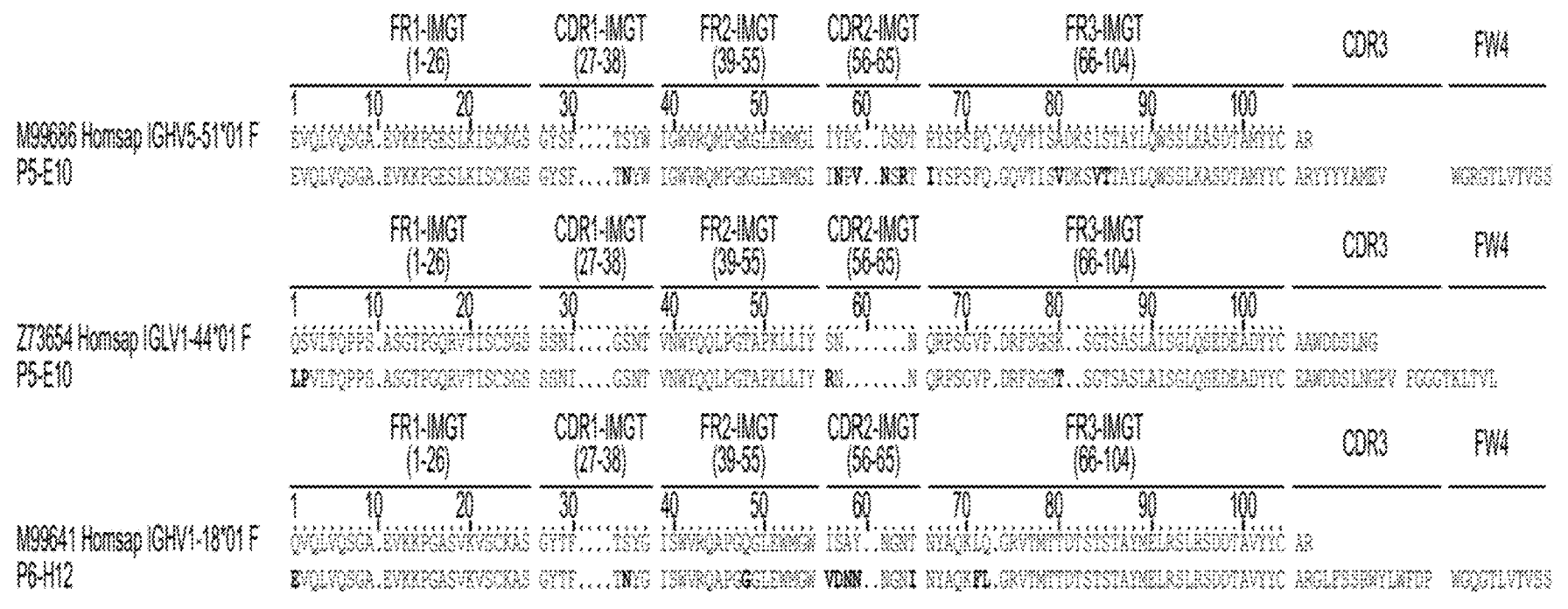
Figure 17:
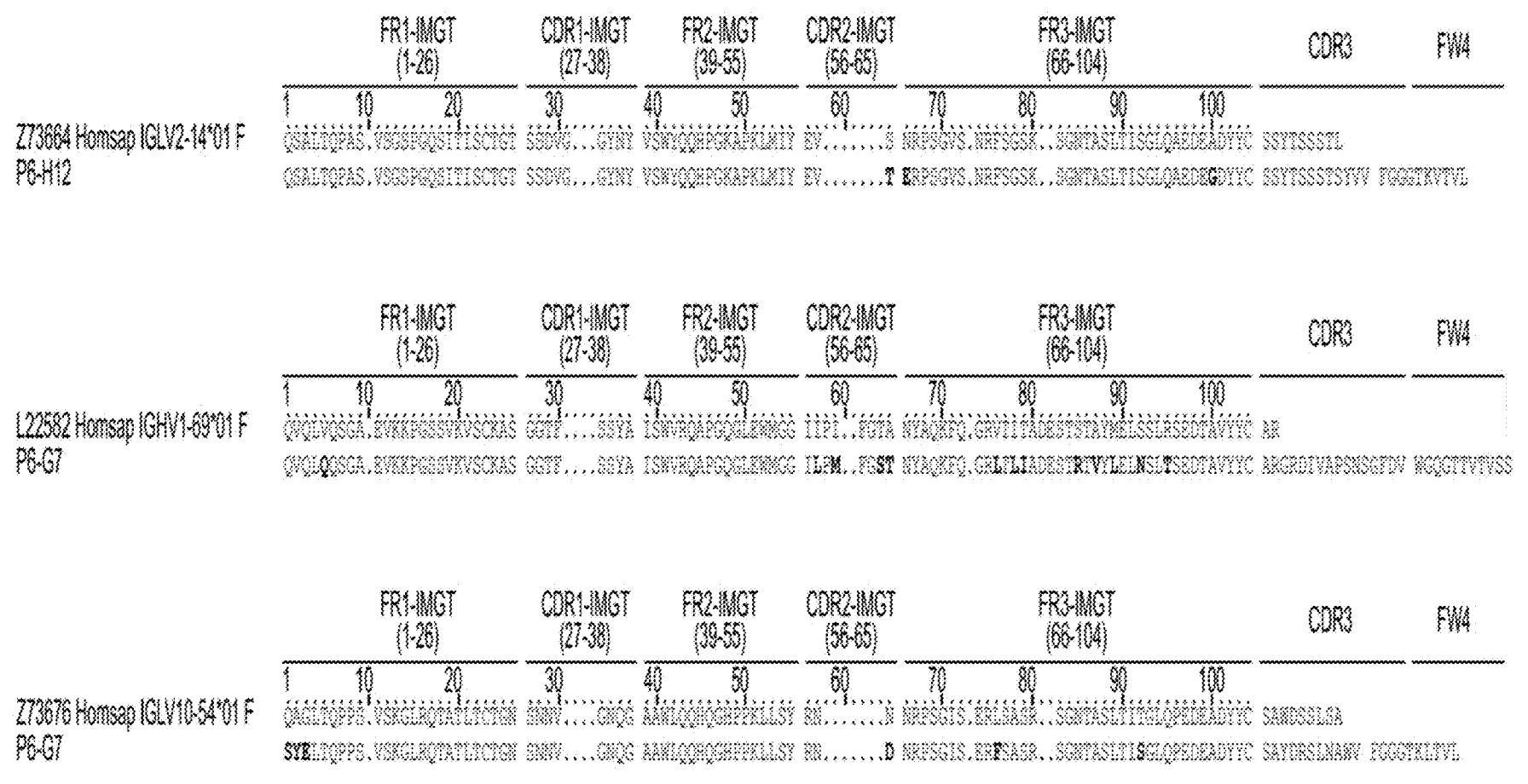
Figure 18:
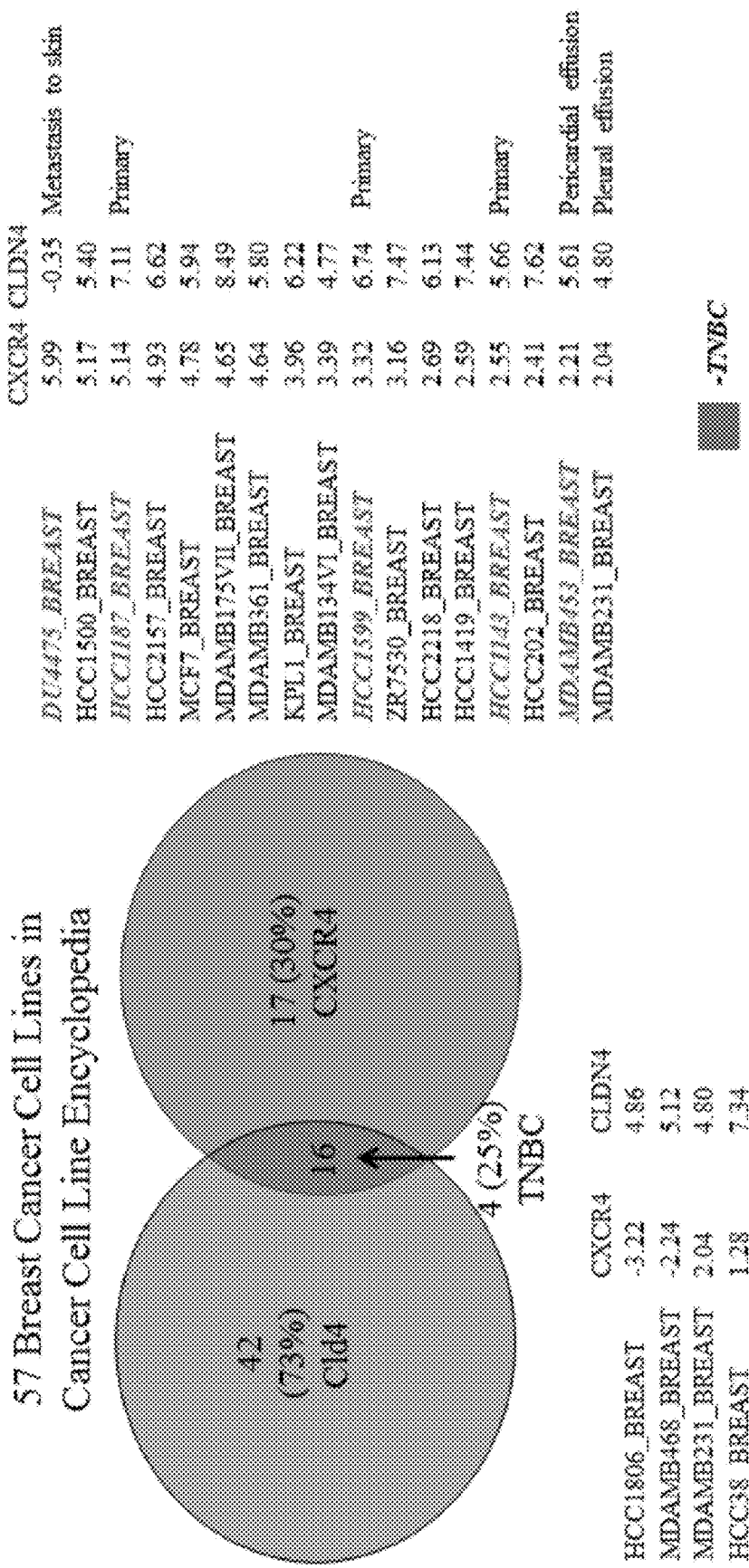
FIG. 18 shows coexpression of CXCR4 and CLD4 on breast cell lines. As described herein, TNBC cell lines tested include DU4475 and HCC1187, which are primary TNBC cell lines with different level of CXCR4 and CLDN4 endogenous cell surface expression. Data include CXCR4 and CLDN4 surface expression determined by flow cytometry, in vitro CART killing assays analyzed with Cellego, and in vivo tumor growth in humanized mice and TIL analysis by flow cytometry.
Figure 19:
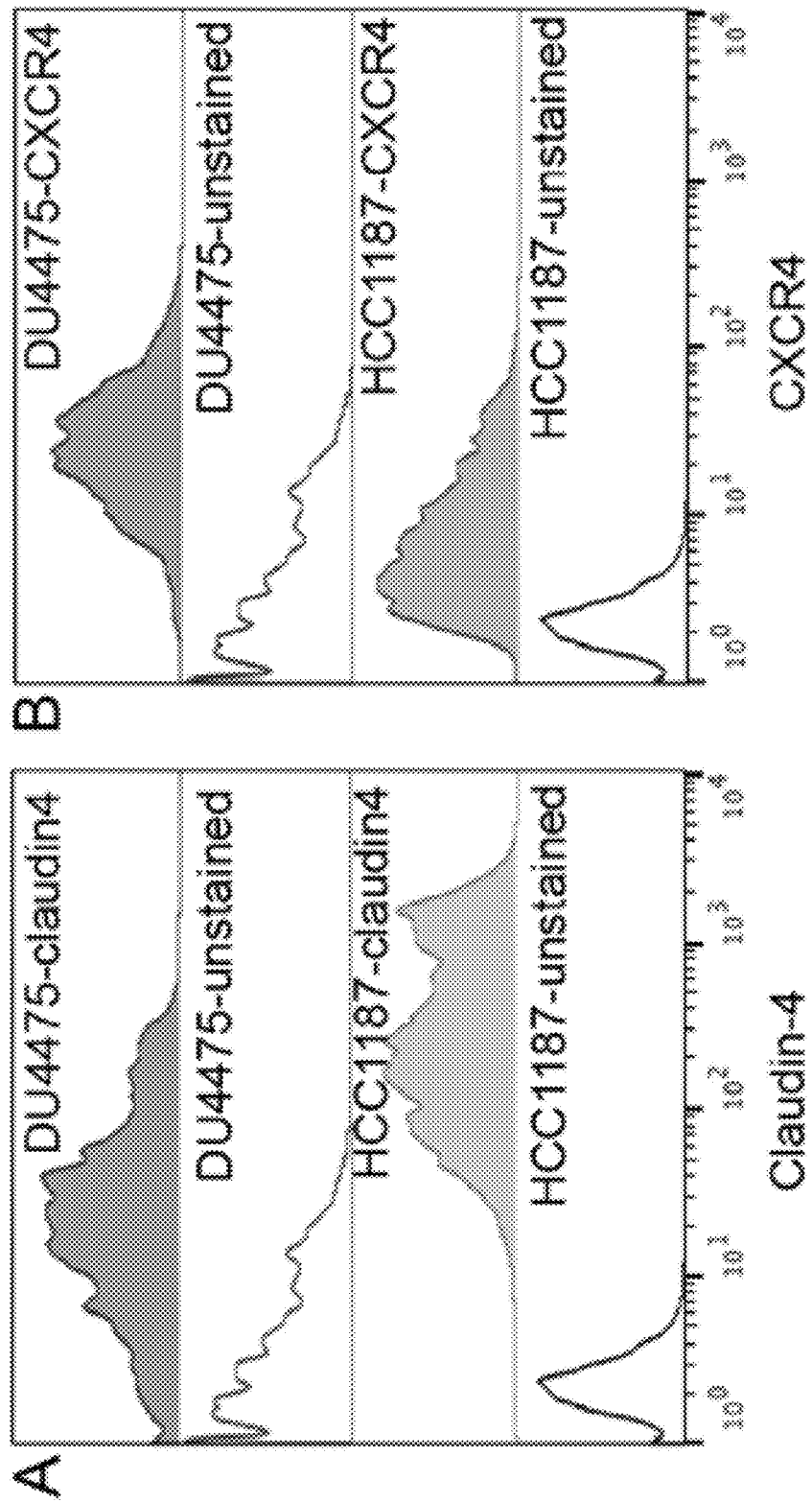
FIG. 19 shows flow cytometry analysis of endogenous CXCR4 and Claudin-4 protein expression of DU4475 and HCC1187. CLDN4 expression was determined with CPE-Fc and FITC anti-human-FC secondary antibody; and CXCR4 expression was determined using anti-CXCR4 antibody followed by APC conjugated secondary antibody.
Figure 20:
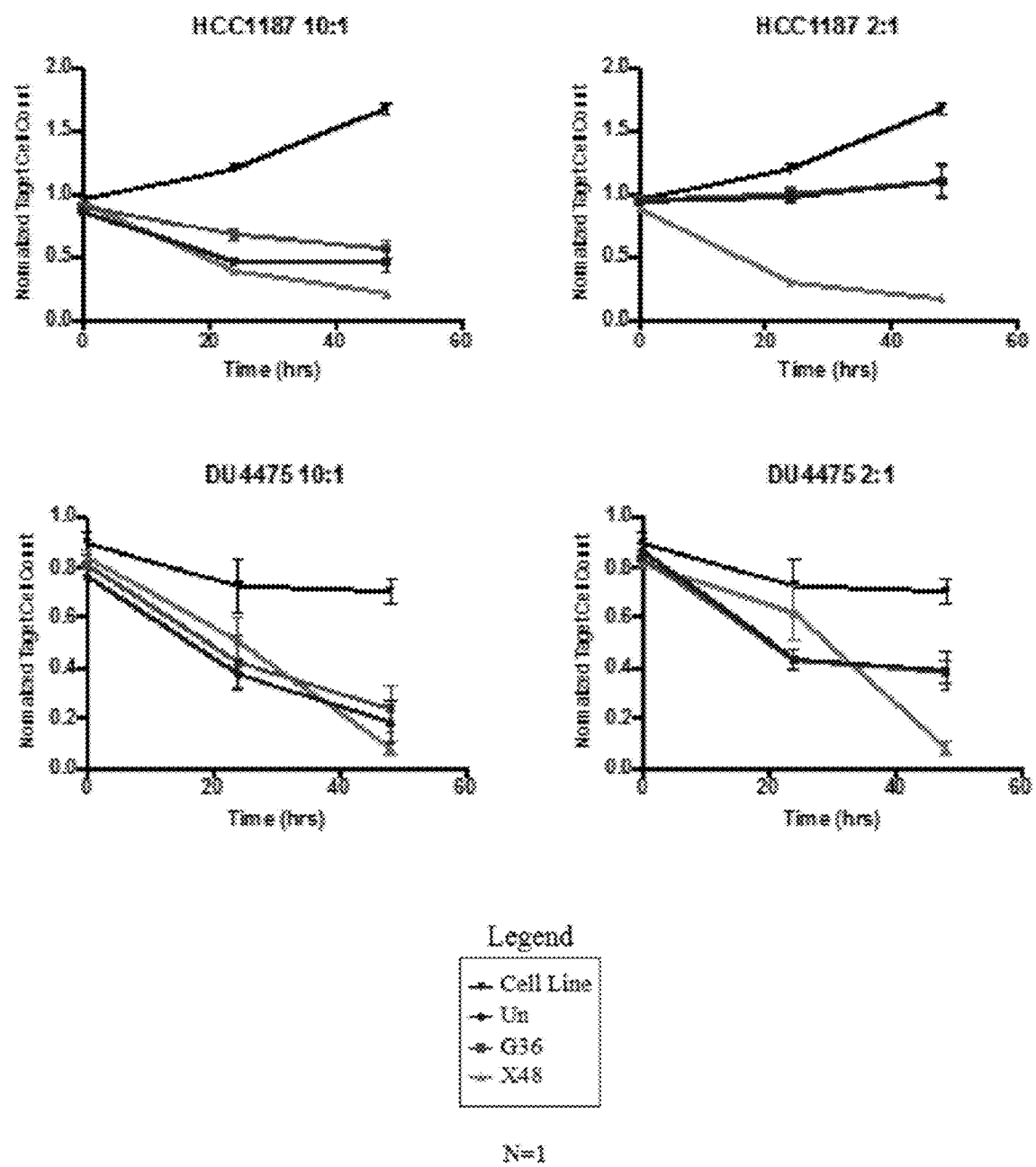
FIG. 20 shows X48 CART kills CXCR4 expressing cell lines HCC1187 and DU4475. Cytotoxicity of HCC1187, DU4475, and MDA-MB-231+/–CXCR4 target cells in co-culture with untransduced (Un, blue), irrelevant CAR (G36, red), CXCR4 targeting CARs (X48, green) and and no T cells (cells only, black) at effector to target (E:T) ratio 10:1 and 2:1 is shown. Enumeration of mCardinal fluorescently labeled target cells were determined with Celego directly after T-cell addition (0 hour), at 24 and 48 hours post T-cell addition.
Figure 21:
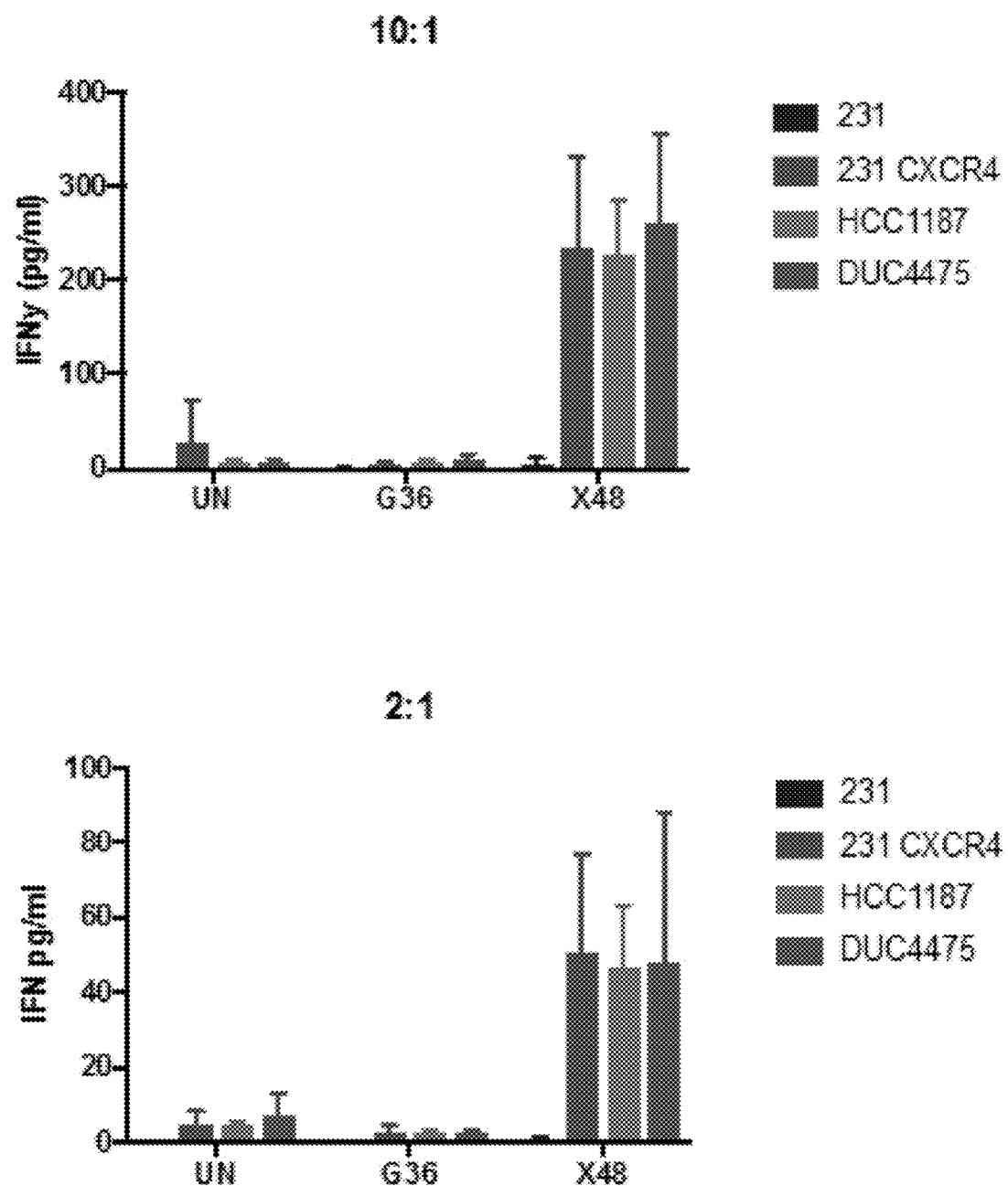
FIG. 21 shows IFN-γ production by CAR-T co-cultured with endogenous expressing CXCR4 cell lines HCC1187 and DU 4475. IFN-γ enzyme-linked immunosorbant assay (ELISA) measuring CAR-T cell activation in the presence of MDA-MB-231 (blue), MDA-MB-231-CXCR4 expressing target cells (red), HCC1187 (green) and DUC4475 (purple) demonstrating specific activation of CAR-T cells only in presence of CXCR4 expressing target cells. Target cell/CAR description same as in FIG. 20. 231 CXCR4-exogenous gene expression.
Figure 22:
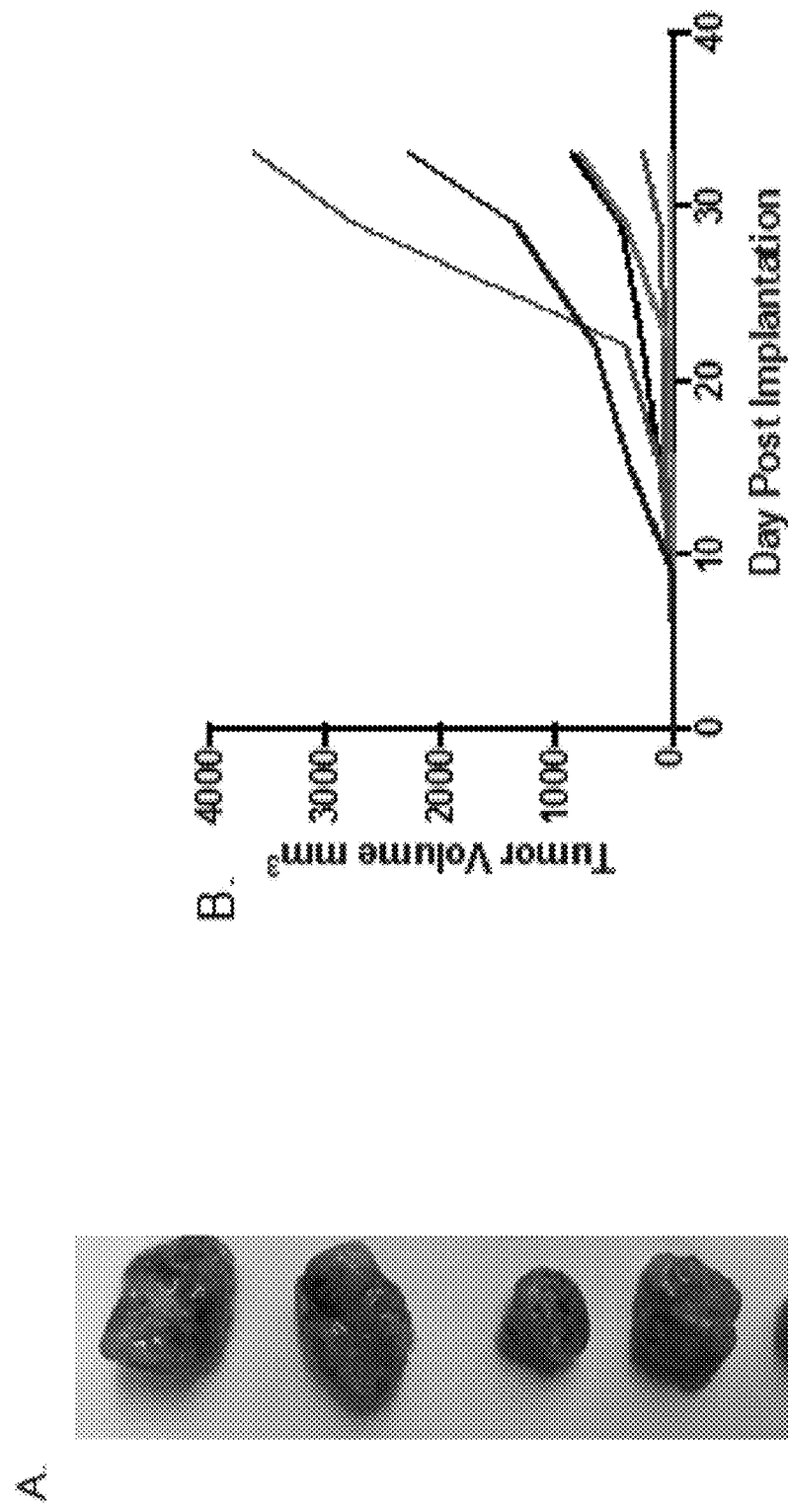
FIG. 22 shows HC1187 tumor growth in humanized mouse model. Shown herein is immune infiltrate of TNBC xenografts in a humanized mouse model. Panel A shows the tumor image at the end of study (33 days post engraftment). Panel B is a graph showing tumor growth in each mouse (n=5) as measured by caliber. Panel C shows the percentage of human CD45+ events as well as other cell subpopulations events in HC1187 TNBC tumors vs. spleen. Panel D is a graph showing the percentage of PD-1+, TIGIT+ or TIGIT+/PD-1+ T-cells of the CD3+ parent population in tumor vs. spleen.

Armed CARTS have the advantage of simultaneously secreting a polypeptide at the targeted site, e.g. tumor site. Referring to FIGS. 6, 16 and 17, for example, armed CARTS can secrete anti-TIGIT antibodies or fragments thereof. TIGIT is a T-cell coinhibitory receptor that limits antitumor and other T-cell dependent chronic immune responses, such as CD8+ T cell-dependent immune responses. TIGIT is expressed on subsets of activated T cells and natural killer (NK) cells. For example, TIGIT is highly expressed on tumor-infiltrating T-cells. In cancer models, antibody blockade of TIGIT contributed to enhanced CD8+ T cell effector function and tumor clearance.

In embodiments, the anti-TIGIT antibody of the armed CART comprises one or more of the anti-TIGIT antibody clones (or fragments thereof, such as FR1, FR2, FR3, FR4, CDR1, CDR2, CDR3, or any combinations of the framework and/or CDR regions therein) described in FIG. 17.

For example, the anti-TIGIT antibody can comprise a CDR1 of the VH region of having the sequence: GYTF . . . TSYG (SEQ ID NO:65); CDR2 of the VH region having the sequence: ISAY . . . NGNT (SEQ ID NO:66); CDR3 of the VH region having the sequence: ARDPGLWFGLTHDYYFDY (SEQ ID NO:67); CDR1 of the VL region having the sequence SSNI . . . GSNT (SEQ ID NO:68); CDR2 of the VL region having the sequence: RN . . . N (SEQ ID NO:69); and CDR3 of the VL region having the sequence: AAWDDSRSGPV (SEQ ID NO:70).

For example, the anti-TIGIT antibody can comprise a CDR1 of the VH region of having the sequence: GFTF . . . SDYS (SEQ ID NO:71); CDR2 of the VH region having the sequence: INSD . . . GSRT (SEQ ID NO: 72); CDR3 of the VH region having the sequence: ARGPGFFGFDI (SEQ ID NO: 73); CDR1 of the VL region having the sequence RSNI . . . GRNS (SEQ ID NO: 74); CDR2 of the VL region having the sequence: SN . . . N (SEQ ID NO: 75); and CDR3 of the VL region having the sequence: AAWDARLTGPL (SEQ ID NO: 76).

For example, the anti-TIGIT antibody can comprise a CDR1 of the VH region of having the sequence: GYSF . . . TNYW (SEQ ID NO:77); CDR2 of the VH region having the sequence: INPV . . . NSRT (SEQ ID NO: 78); CDR3 of the VH region having the sequence: ARYYYAMEV (SEQ ID NO: 79); CDR1 of the VL region having the sequence SSNI . . . GSNT (SEQ ID NO: 80); CDR2 of the VL region having the sequence: RN . . . N (SEQ ID NO: 81); and CDR3 of the VL region having the sequence: EAWDDSLNGPV (SEQ ID NO: 82).

For example, the anti-TIGIT antibody can comprise a CDR1 of the VH region of having the sequence: GYTF . . . TNYG (SEQ ID NO:83); CDR2 of the VH region having the sequence: VDNN . . . NGNI (SEQ ID NO: 84); CDR3 of the VH region having the sequence: ARGLF-SSRWYLWFDP (SEQ ID NO: 85); CDR1 of the VL region having the sequence SSDVG . . . GYNY (SEQ ID NO: 86); CDR2 of the VL region having the sequence: EV . . . T (SEQ ID NO: 87); and CDR3 of the VL region having the sequence: SSYTRSSTSYVV (SEQ ID NO: 88).

For example, the anti-TIGIT antibody can comprise a CDR1 of the VH region of having the sequence: GGTF . . . SSYA (SEQ ID NO:89); CDR2 of the VH region having the sequence: ILPM . . . FGST (SEQ ID NO: 90); CDR3 of the VH region having the sequence: ARGRDI-VAPSNSGFDV (SEQ ID NO: 91); CDR1 of the VL region having the sequence SNNV . . . GNQG (SEQ ID NO: 92); CDR2 of the VL region having the sequence: RN . . . D (SEQ ID NO: 93); and CDR3 of the VL region having the sequence: SAYDRSLNAWV (SEQ ID NO: 94).

In embodiments, the anti-TIGIT antibody can comprise a heavy chain with a VH comprising a CDR1 of SEQ ID NO: 65, 71, 77, 83, or 89; a CDR2 of SEQ ID NO: 66, 72, 78, 84, or 90; and a CDR3 of SEQ ID NO: 67, 73, 79, 85, or 91; or any combination thereof.

In embodiments, the anti-TIGIT antibody can comprise a light chain with a VL comprising a CDR1 of SEQ ID NO: 68, 74, 80, 86, or 92; a CDR2 of SEQ ID NO: 69, 75, 81, 87, or 93; and a CDR3 of SEQ ID NO: 70, 76, 82, 88, or 94; or any combination thereof.

Armed CART can be constructed by including a nucleic acid encoding the polypeptide of interest after the intracellular signaling domain. Preferably, there is an internal ribosome entry site, (IRES), positioned between the intracellular signaling domain and the polypeptide of interest. One skilled in the art can appreciate that more than one polypeptide can be expressed by employing multiple IRES sequences in tandem.

In one embodiment, the methods and compositions presented herein provide a target-specific T cell, such as a T cell with specificity for CXCR4 and/or claudin-4, of second generation armed with the power to secrete polypeptides in the tumor microenvironment, for example to combat T cell exhaustion.

Introduction of Constructs into CTLs

Expression vectors that encode the CARs can be introduced as one or more DNA molecules or constructs, where there may be at least one marker that will allow for selection of host cells that contain the construct(s).

The constructs can be prepared in conventional ways, where the genes and regulatory regions can be isolated, as appropriate, ligated, cloned in an appropriate cloning host, analyzed by restriction or sequencing, or other convenient means. Particularly, using PCR, individual fragments including all or portions of a functional unit can be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, can knock-out an endogenous gene and replace it (at the same locus or elsewhere) with the gene encoded for by the construct using materials and methods as are known in the art for homologous recombination. For homologous recombination, one may use either .OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

The constructs can be introduced as a single DNA molecule encoding at least the CAR and optionally another gene, or different DNA molecules having one or more genes. Other genes include genes that encode therapeutic molecules or suicide genes, for example. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

Methods of Use

Aspects of the invention are directed towards methods of treating a subject afflicted with a cancer.

Aspects of the invention are further directed towards methods of stopping or reducing progression or promoting regression of a cancer in a subject.

Still further, aspects of the invention are directed towards a method of reducing cellular proliferation of a cancer cell in a subject.

Figure 3:
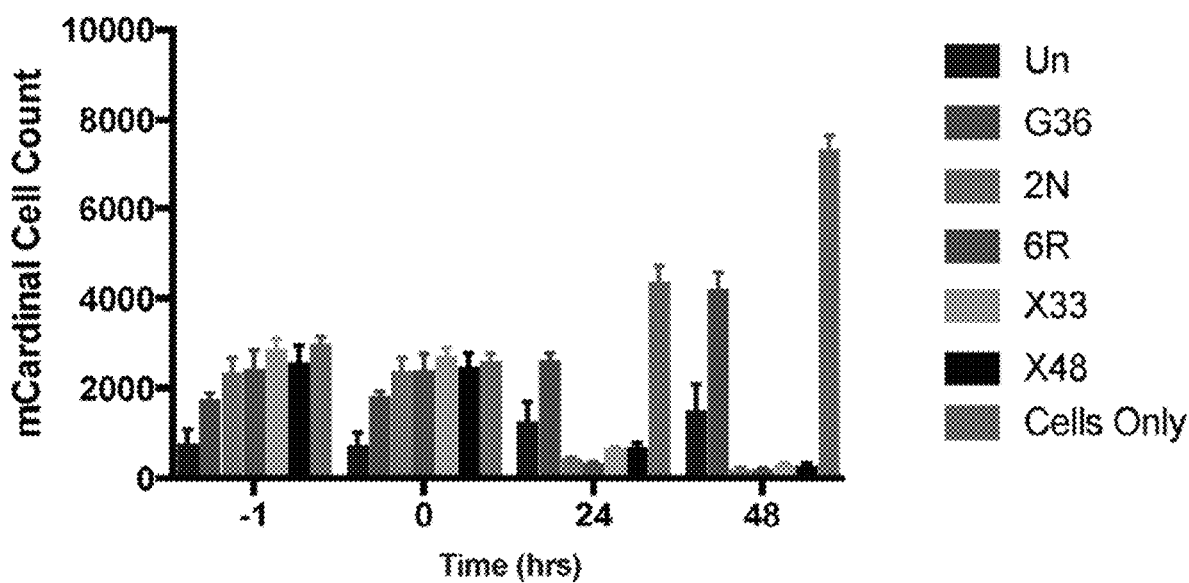
FIG. 3 shows Specific cytotoxicity of CXCR-4 expressing target cells by CXCR4-targeting chimeric antigen receptor (CAR) T cells by quantification of fluorescently labeled target cells. Enumeration of mCardinal fluorescently labeled target cells (TOP GRAPH) MDA-MB-231-CXCR4, or (BOTTOM GRAPH) MDA-MB-231 alone (time −1 hour), directly after T-cell addition (0 hour), at 24 and 48 hours post T-cell addition. Loss of target cells at 24 and 48 hours by 2N, 6R, X33 and X48 only in A, and not B demonstrate, specific killing due to recognition of CXCR4 on target cells. Controls include untransduced T cells (Un), irrelevant CAR (G36) and no T cells (cells only)
Figure 3:
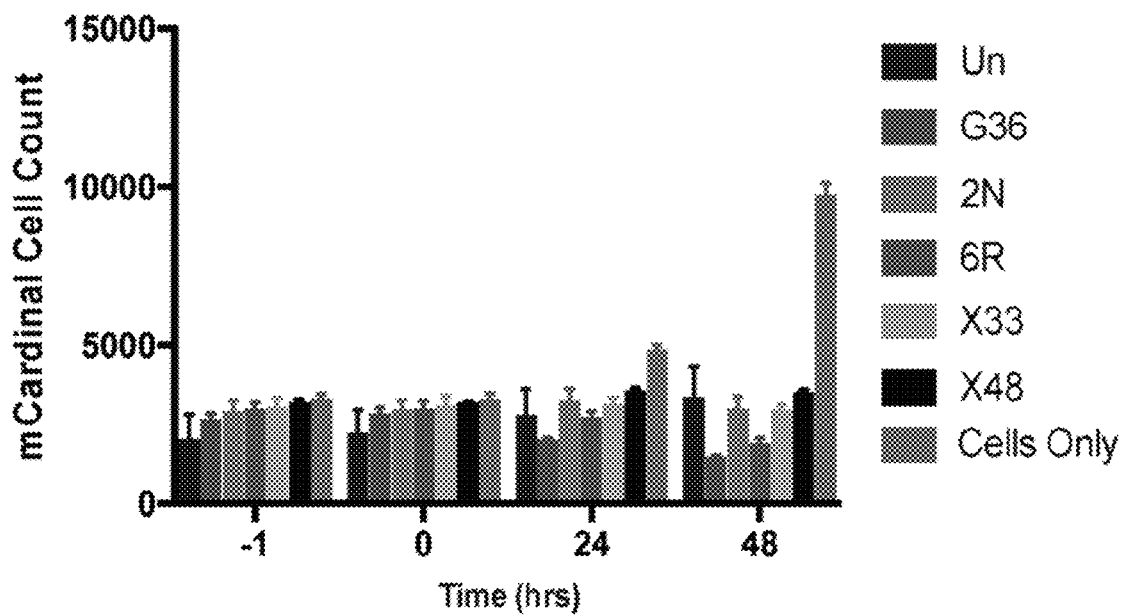
Figure 4:
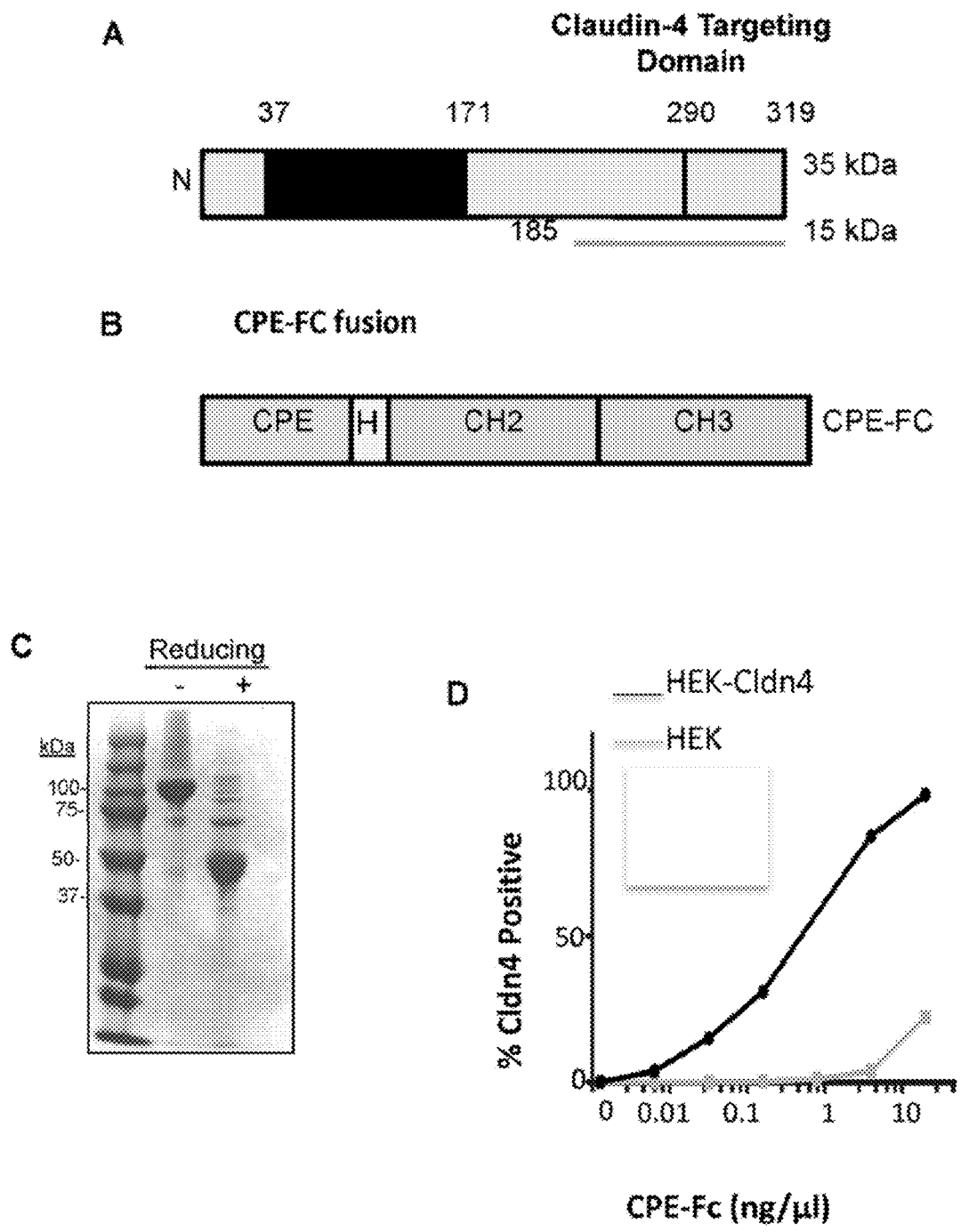
FIG. 4 shows *Clostridium perfringens* endotoxin (CPE)-FC fusion protein recognizes claudin-4 on cells. A, Linear schematic of *Clostridium perfringens* endotoxin protein. Cytotoxic domain CD3+ T-cells of CD45+ parent population.
Figure 5:
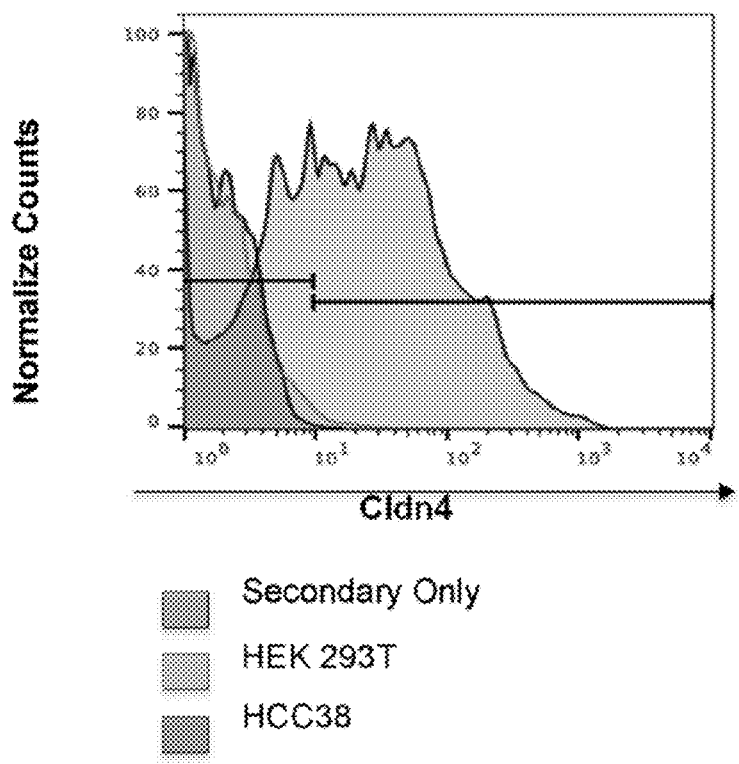
Figure 5:
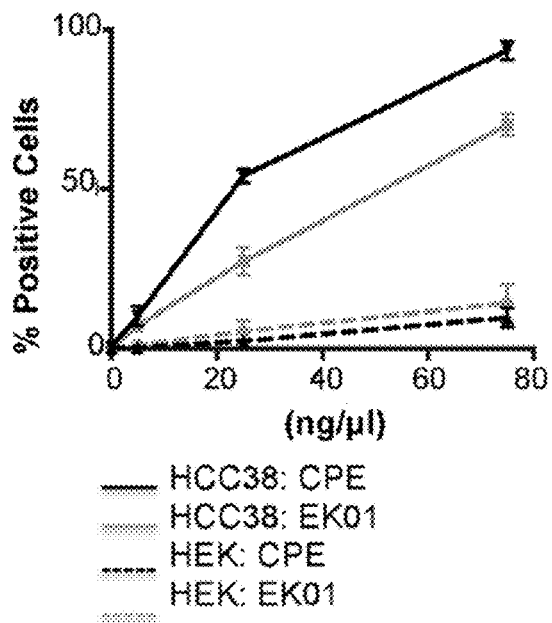

Aspects of the invention are also directed towards methods of inducing cytotoxicity of cells. For example, referring to FIG. 2 and FIG. 3, specific cytotoxicity of CXCR-4 expressing cells is induced by CXCR-4 targeting chimeric antigen receptor T cells.

"Cancer" and "cancerous" refer to or describe, for example, the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, smallcell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

In cancer, the normal intercellular interactions in tissues are disrupted, and the tumor microenvironment evolves to accommodate the growing tumor. The tumor microenvironment (TME) refers to the cellular environment in which a tumor exists, including components such as surrounding blood vessels, immune cells, fibroblasts, bone marrow-derived inflammatory cells, lymphocytes, signaling molecules and the extracellular matrix (ECM). Tumor microenvironment is complex and is heavily influenced by immune system.

This invention provides CAR-T cell therapy for triple-negative breast cancer, among others (such as those described herein). The secretion of a mono, bi-, or tri-specific minibody, antibody or minibody/antibody fusion protein by the CAR-T cell at the tumor site could provide additional benefit by altering (i.e., modulating) the immune-repressive tumor microenvironment.

In embodiments, the method comprises administering to a subject afflicted with a cancer a therapeutically effective amount of an engineered cell as described herein. Therapeutically effective amounts can depend on the severity and course of the cancer, previous therapy, the subject's health status, weight, and response to the drugs, and the judgment of the treating physician.

The subject can be afflicted with cancer such as liquid cancers (i.e., blood cancers) and/or solid cancers (i.e., tumors). The cancer can be benign or malignant, and can be one that is influenced by the immune system.

Embodiments as described herein can modulate the immune system so as to treat the subject afflicted with cancer. "Modulating" can refer to up-regulation, induction, stimulation, potentiation, and/or relief of inhibition, as well as inhibition, attenuation and/or down-regulation or suppression. In embodiments, the activity of the subject's immune system is modulated, the microenvironment surround the cancer cell and/or tumor is modulated, or both. For example, embodiments as described herein can alter the immune-repressive tumor microenvironment, reducing the microenvironment-dependent immune suppression, so as to modulate (or allow) the immune system to kill tumor cells.

One embodiment is directed towards methods of treating a subject afflicted with triple-negative breast cancer (TNBC), a highly aggressive subtype of breast cancer (e.g., a solid tumor) with poor clinical prognosis. While treated with chemotherapies, the high incidence of relapse signifies the need for novel, targeted therapies. Immune therapies, such as those described herein, offer an exciting therapeutic option for TNBC. For example, embodiments comprise engineering a chimeric-antigen receptor (CAR) T-cell factory, a CAR T-cell that secretes immune-modulating antibodies, for TNBC.

An "individual" or "subject" can be a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The cells according to the invention can be used for treating cancer in a patient in need thereof. In another embodiment, said isolated cell according to the invention can be used in the manufacture of a medicament for treatment of a cancer, viral infections of autoimmune disorders, in a patient in need thereof.

The present invention relies on methods for treating patients in need thereof, said method comprising at least one of the following steps: (a) providing a chimeric antigen receptor cells according to the invention and (b) administrating the cells to said patient.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer. Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to an embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM PATH. In another embodiment, the cell compositions of the present invention are administered following B-cell ablative therapy such as agents that react with CD20, e.g., Rittman. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Administration of Cells

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Depending upon the nature of the cells, the cells can be introduced into a host organism, e.g. a mammal, in a wide variety of ways. The cells can be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In some embodiments, the cells are encapsulated to inhibit immune recognition and placed at the site of the tumor.

The cells can be administered as desired. Depending upon the response desired, the manner of administration, the life of the cells, the number of cells present, various protocols may be employed. The number of administrations will depend upon the factors described above at least in part.

The administration of the cells or population of cells according to the present invention can be carried out in any convenient manner, including by aerosol inhalation, injection, ingestion, transfusion, implantation or transplantation. The compositions described herein may be administered to a patient subcutaneously, intradermaly, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

Nucleic Acid-Based Expression Systems

The CARs of the present invention can be expressed from an expression vector. Recombinant techniques to generate such expression vectors are well known in the art.

DNA constructs, which can also be referred to as "DNA vectors", as described herein, can be cloned into a vector which will be used to transduce and produce chimeric-antigen receptor T-cells that secrete polypeptides and/or fragments thereof. For example, DNA constructs can be cloned into a lentiviral vector for production of lentivirus, which will be used to transduce and produce chimeric-antigen receptor T-cells that secrete a mono, bi- or tri-specific immune-modulating antibody/minibody and/or antibody-fusion protein at the tumor site.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cisacting regulatory sequence involved in the transcriptional activation of a nucleic acid sequence.

A promoter may be one naturally associated with a nucleic acid sequence, as may be obtained by isolating the 5 prime' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals In certain embodiments of the invention, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present invention. In particular aspects, the transplanted cells or tissues may be placed into an organism. In preferred facets, a nucleic acid is expressed in the transplanted cells.

Kits of the Invention

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly ueful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapies. In the context of the present invention, it is contemplated that cell therapy could be used similarly in conjunction with chemotherapeutic, radiotherapeutic, or immunotherapeutic intervention, as well as pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Chemotherapy

Cancer therapies also include a variety of combination therapies with both chemical and radiation based treatments.

Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention Radiotherapy Other factors that cause DNA damage and have been used extensively include what are commonly known as .gamma-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include PD-1, PD-L1, CTLA4, carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Methods of Assessing Activity of Engineered CAR T Cells

Aspects of the invention are further directed towards methods of and kits for assessing the killing capabilities of engineered CAR T cells. Specifically, embodiments are directed towards an immune complex analysis method and kits to determine the CAR T cell activity during co-culture with cancer cells. First, different target cancer cells (for example, HEK293T, MDA-MB-231, MDA-MB-468, HCC38, and skrc59) are stained with a dye, (for example, ViaStain™ Tracer Blue dye), seeded in a plate (for example a 96-well plate), and incubated for a period of time (for example 12 hours, or overnight). Next, different T cell types (for example, two different T cell types) are added to the wells (for example at a ratio of 20:1 effector-to-target (E:T) ratios) and allowed to co-culture for a period of time (for example, 24 hours). Finally, the plate is scanned and analyzed (for example, using the bright field and blue fluorescent channels). The immune complexes were analyzed by confluence measurement and compared to the negative control of untransduced T cells. As a result, data plots displayed the CAR T cell activities for all of tested target and effector cells combinations. Utilization of an image cytometry platform can visually confirm interactions between effector and target cells, thus making results highly accurate and robust.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

CXCR4 and Claudin-4 Bispecific Chimeric Antigen Receptor T-Cell Therapy Secreting an Immune-Modulating Antibody Chimeric antigen receptors fuse antigen-specific antibody fragments to T-cell co-stimulatory domains and the CD3 zeta intracellular signaling, allowing for the re-direction of T-cells towards an antigen presented on a cell of interest including tumor cells. This invention combines antibody fragments, including, but not limited to, single-chain variable fragments (scFv) directed at C-X-C chemokine receptor type 4 and claudin-4. The DNA encoding the scFVs will be cloned in frame to DNA encoding necessary CAR-T elements such as, but not limited to, CD8 hinge regions, transmembrane, co-stimulatory domains of molecules of immunological interest such as, but not limited to, CD28 and 41BB and CD3-zeta intracellular signaling domains. Furthermore, in a second expression construct in the same DNA vector, a mini body (scFv-Fc) or antibody directed against a single or multiple antigens of interest are cloned after an internal ribosomal entry site (IRES). These DNA constructs are cloned into a lentiviral vector for production of lentivirus which will be used to transduce and produce chimeric-antigen receptor T-cells that secrete a mono, bi- or tri-specific immune-modulating antibody/minibody and/or antibody-fusion protein at the tumor site.

No targeted treatments exist for triple-negative breast cancer (TNBC), therefore chemotherapy remains the only treatment for patients. Immunotherapies like anti-PD_L1 had limited success (18% response rate) in for TNBC suggesting that these therapies alone is not an effective treatment. This invention would provide the first CAR-T cell therapy for triple-negative breast cancer. The secretion of a mono, bi-, or tri-specific minibody, antibody or minibody/antibody fusion protein by the CAR-T cell at the tumor site could provide additional benefit by altering the immune-repressive tumor microenvironment.

Example 2

High-Throughput Immune Complex Analysis Method for CAR T Cell-Mediated Cytotoxicity Using the Celigo Image Cytometer Cancer immunotherapy has been gaining momentum in the field of cancer research. Advancements in combination immunotherapy as well as Chimeric Antigen Receptor (CAR) T technology have introduced new methods to combat various cancer diseases. Direct cell-mediated cytotoxicity assays are required to assess the killing capability of the engineered CAR T cells. Traditionally, these assays are conducted by measuring the amount of released Chromium, calcein AM, or Lactate dehydrogenase (LDH) molecules after the target cancer cells are killed with CAR T cells. These methods require a large amount of target cells which may not be ideal when working with donor primary samples. Additionally, they cannot specifically analyze the immune complexes formed during CAR T cell killing. Recent advancement in imaging technologies have developed novel methods for assessing these immune complexes. In this work, we demonstrated an immune complex analysis method using the Celigo Image Cytometer to determine the CAR T cell activity during co-culture with cancer cells. First, different target cancer cells (for example, HEK293T, MDA-MB-231, MDA-MB-468, HCC38, and skrc59) are stained with a dye, (for example, ViaStain™ Tracer Blue dye), seeded in a plate (for example a 96-well plate), and incubated for a period of time (for example 12 hours, or overnight). Next, different T cell types (for example, two different T cell types) are added to the wells (for example at a ratio of 20:1 effector-to-target (E:T) ratios) and allowed to co-culture for a period of time (for example, 24 hours). Finally, the plate is scanned and analyzed (for example, using the bright field and blue fluorescent channels). The immune complexes were analyzed by confluence measurement and compared to the negative control of untransduced T cells. As a result, data plots displayed the CAR T cell activities for all of tested target and effector cells combinations. Utilization of an image cytometry platform can visually confirm interactions between effector and target cells, thus making results highly accurate and robust. Unlike the traditional release assays, the ability to analyze the immune complexes formed during co-culture assays can provide additional important functionality information of the effector cells.

Example 3

A Bispecific Chimeric Antigen Receptor T-Cell Factory for Triple-Negative Breast Cancer Triple-negative breast cancer (TNBC) is a highly aggressive subtype of breast cancer with poor clinical prognosis. While treated with chemotherapies, the high incidence of relapse signifies the need for novel, targeted therapies. Immune therapies offer an exciting therapeutic option for TNBC.

Embodiments as described herein comprise engineering a chimeric-antigen receptor (CAR) T-cell factory, a CAR T-cell that secretes immune-modulating antibodies, for TNBC.

Chimeric-antigen receptor (CAR) T-cell therapies redirect a patient's T-cells to kill tumor cells by the exogenous expression of a CAR. A CAR is a membrane spanning fusion protein that links the antigen recognition domain of an antibody to the intracellular signaling domains of the T-cell receptor and co-receptor. Solid tumors offer unique challenges for CAR-T therapies. Unlike blood cancers, tumor-associated target proteins are overexpressed between the tumor and healthy tissue resulting in on-target/off-tumor T-cell killing of healthy tissues. Furthermore, immune repression in the tumor microenvironment (TME) limits the activation of CAR-T cells towards killing the tumor.

Without wishing to be bound by theory, a bispecific CAR targeting two antigens on TNBC will mitigate on-target/off-tumor T-cell killing and that the secretion of a checkpoint blockade antibody will remove repression in the tumor microenvironment. Following local immune restoration, the CAR-T cells and other cells in the TME will work synergistically to shrink and clear tumors.

Our current work evaluates human single-chain variable fragments (scFvs) to serve as CAR-targeting moieties. We are evaluating the efficacy of scFvs to specifically kill target cells in vitro. This work will define lead scFvs used in the engineering of our bispecific CAR. Future work will evaluate this therapy in humanized mouse models of TNBC.

Example 4

A Bispecific CAR T-Cell Factory for Triple-Negative Breast Cancer

Triple-negative breast cancer (TNBC) is a highly aggressive subtype of breast cancer with poor clinical prognosis (1). While treated with chemotherapies, the high incidence of relapse signifies the need for novel, targeted therapies. Immune therapies offer an exciting therapeutic option for TNBC. The goal is to engineer a chimeric antigen receptor (CAR) T-cell factory, a CAR T-cell that secretes an immune-modulating antibody, for TNBC (2). CARs for solid tumors are thwarted by on-target/off-tumor killing and an immune-suppressive tumor microenvironment (TME, 3). Without being bound by theory, a bispecific CAR targeting two antigens on TNBC can mitigate on-target/off-tumor T-cell killing and the secretion of a checkpoint blockade antibody can remove repression in the tumor microenvironment. Following local immune restoration, the CAR-T cells and other cells in the TME can work synergistically to shrink and clear tumors. This therapy will be evaluated in a humanized mouse model of TNBC.

Objectives: (1) Evaluate CXCR4 recognizing single-chain variable fragments (scfv) as CAR-T cell targeting domains; (2) Assess immune infiltration of TNBC xenografts in humanized mouse model.

Methods

In vitro CAR-T killing. CD8+ T-cells were transduced with CAR gene via lentivirus. Stable fluorescent, CXCR4 transduced, TNBC cell lines were co-cultured with CAR T-cells. Target cells were enumerated using Nexcelom, Celigo Image Cytometer.

Humanized Mouse Model. Neonate NSG-SGM3 were implanted with human hematopoietic stem cells. Engraftment of humane immune system was confirmed at 12-20 weeks. Four million CXCR4-transduced TNBC cells were implanted into mammary fat pad. Flow cytometry analysis of tumor single-cell suspensions was conducted.

Conclusions: Four CXCR4-targeting CARS were identified with various killing kinetics on two CXCR4-transduced TNBC cell lines. HCC38 was identified as a highly immune infiltrated xenograft in a humanized mouse model.

Other Embodiments

Bispecific CAR Development. In one embodiment, scFvs directed against second antigen for target cell killing can be evaluated. In another embodiment, a bispecific CAR can be engineered. The therapeutic efficacy of such a bispecific CAR-T factory can then be tested.

Mouse Model Development. In one embodiment, a transcriptome analysis of tumor and tumor-infiltrating lymphocytes (TIL) can be conducted. In another embodiment, a multi parameter IHC of the tumor microenvironment can be conducted. In some embodiments, the infiltrate can be confirmed with a second haematopoietic stem cell (HSC) donor.

References for this Example

1—Foulkes W D, et al. (2010) Triple-negative breast cancer. The New England journal of medicine. 2010; 363 (20):1938-48.

2—Suarez E R, et al. (2016) Chimeric antigen receptor T cells secreting anti-PD-L1 antibodies more effectively regress renal cell carcinoma in a humanized mouse model. *Oncotarget* 7(23):34341-34355.

3—Kunert A, et al. (2018) Engineering T cells for adoptive therapy: outsmarting the tumor. *Current Opinion in Immunology* 51:133-139.

Example 5

CAR-T Killing

Stable fluorescent target cell lines were made by transduction with a lentivirus construct containing mCardinal with carboxyl-terminal nuclear localization signal. mCardinal expressing cells were sorted using flow cytometry to enrich for the fluorescent population. Three-thousand target cells were plated per assay well.

To make CAR-T cells, CD8+ cells were purified from the PBMC from healthy donors and cultured in media containing interleukin-21 and CD3/CD28 costimulatory beads. After 24 hours in culture, T-cells were transduced with lentivirus containing the indicated CAR. After 5-9 days in culture, CAR-T cells were mixed with target cells at an T-cell (effector) to target (breast cancer cell line) of 10:1 or 2:1. Assays were imaged using a Celigo image cytometer at 0, 24 and 48 hours and fluorescent target cells counted.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. An engineered cell comprising a nucleic acid encoding a chimeric antigen receptor, wherein the chimeric antigen receptor is specific for two or more antigens on the surface of a cancer cell, wherein the two or more antigens comprise CXCR4 and claudin-4, wherein the chimeric antigen receptor comprises:
   a VH with a CDR1 comprising GFTVSSNY (SEQ ID NO: 59); CDR2 comprising IYSGGST (SEQ ID NO: 60); and CDR3 comprising ARDNPLSAFDI (SEQ ID NO: 61); and
   a VL with a CDR1 comprising QSINSW (SEQ ID NO: 62); CDR2 comprising KAS (SEQ ID NO: 63); and CDR3 comprising QQYDDLPLT (SEQ ID NO: 64).

2. The engineered cell of claim 1, wherein the engineered cell comprises a T cell or an NK cell.

3. The engineered cell of claim 2, wherein the T cell is CD4$^+$, CD8$^+$, or a mixed population of CD4$^+$ and CD8$^+$ T cells.

4. The engineered T-cell of claim 1, wherein the chimeric antigen receptor comprises a VH comprising SEQ ID NO: 1, 2, 3, 4, 5, 6, 7, or 8; a VL comprising SEQ ID NO: 9, 10, 11, 12, 13, 14, 15, or 16; or any combination thereof.

5. The engineered T-cell of claim 1, wherein the chimeric antigen receptor further comprises:
   a VH with CDR1 comprising SYGMH (SEQ ID NO:17); CDR2 comprising VISYDGSNKYYADSVKG (SEQ ID NO:18); CDR3 comprising DLVAAAGTAFDI (SEQ ID NO:19); and
   a VL with CDR1 comprising TGTISDVGGHNFVS (SEQ ID NO:20); CDR2 comprising EVTKRPA (SEQ ID NO:21); CDR3 comprising SSYGGSNDVI (SEQ ID NO:22);
   a VH with CDR1 comprising SNFVAWN (SEQ ID NO:23); CDR2 comprising RTYYRSRWYN-DYAVSVQS (SEQ ID NO:24); CDR3 comprising GQHSGFDF (SEQ ID NO:25); and
   a VL with CDR1 comprising TGNSNNVGNQGAA (SEQ ID NO:26); CDR2 comprising RNNNRPS (SEQ ID NO:27); and CDR3 comprising SAWDNRLKTYV (SEQ ID NO:28);
   a VH with CDR1 comprising SYGIS (SEQ ID NO:29); CDR2 comprising WISAYNGNTNYAQKLQG (SEQ ID NO:30); CDR3 comprising DTPGIAAR-RYYYYGMDV (SEQ ID NO:31); and
   a VL with CDR1 comprising QGDSLRKFFAS (SEQ ID NO:32); CDR2 comprising GKNSRPS (SEQ ID NO:33); and CDR3 comprising NSRDSRDNHQV (SEQ ID NO:34);
   a VH with CDR1 comprising SYPMH (SEQ ID NO:35); CDR2 comprising VISSDGRNKYYPDSVKG (SEQ ID NO:36); and CDR3 comprising GGYHDFWSGPDY (SEQ ID NO:37); and
   a VL with CDR1 comprising RASQSVNTNLA (SEQ ID NO:38); CDR2 comprising GASSRAT (SEQ ID NO:39); and CDR3 comprising QHYGSSPLT (SEQ ID NO:40);
   a VH with CDR1 comprising SYAMS (SEQ ID NO:41); CDR2 comprising NIKQDGSEKYYVDSVKG (SEQ ID NO:42); and CDR3 comprising DQVSGITIFGGKWRSPDV (SEQ ID NO:43); and
   a VL with CDR1 comprising QGDSLRSYYAS (SEQ ID NO:44); CDR2 comprising GKNNRPS (SEQ ID NO:45); and CDR3 comprising NSRSGSQRV (SEQ ID NO:46);
   a VH with CDR1 comprising NYGLH (SEQ ID NO:47); a CDR2 comprising VISHDGTKKYYADSVKG (SEQ ID NO:48); and a CDR3 comprising DGGYCSG-GRCYSYGMDV (SEQ ID NO:49); and
   a VL with CDR1 comprising SGSRSNIGSNTVN (SEQ ID NO:50); CDR2 comprising TNNQRPS (SEQ ID NO:51); and CDR3 comprising LSFDSSLTSYV (SEQ ID NO:52);
   a VH with CDR1 comprising RYGMH (SEQ ID NO:53); CDR2 comprising LISYDGSKTFYGESVKG (SEQ ID NO: 54); and CDR3 comprising ATVTTDGYYYMDV (SEQ ID NO: 55); and
   a VL with CDR1 comprising SGSRSNIGGNTVN (SEQ ID NO:56); CDR2 comprising ANNQRPS (SEQ ID NO: 57); and CDR3 comprising AAWDDNLSGHVV (SEQ ID NO: 58);
   or any combination thereof.

6. The engineered cell of claim 1, further comprising a polypeptide that can be secreted from the engineered cell.

7. The engineered cell of claim 6, wherein the polypeptide modulates the immune system of a subject.

8. The engineered cell of claim 6, wherein the polypeptide comprises an antibody or fragment thereof.

9. The engineered cell of claim 8, wherein the polypeptide comprises an antibody specific for TIGIT, CAIX, GITR, PD-L1, PD-L2, PD-1, or CCR4.

10. A nucleic acid encoding a chimeric antigen receptor, wherein the chimeric antigen receptor is specific for two or more antigens on the surface of a cancer cell, wherein the two or more antigens comprise CXCR4 and claudin-4, and wherein the chimeric antigen receptor comprises:

a VH with a CDR1 comprising GFTVSSNY (SEQ ID NO: 59); CDR2 comprising IYSGGST (SEQ ID NO: 60); and CDR3 comprising ARDNPLSAFDI (SEQ ID NO: 61); and a VL with a CDR1 comprising QSINSW (SEQ ID NO: 62); CDR2 comprising KAS (SEQ ID NO: 63); and CDR3 comprising QQYDDLPLT (SEQ ID NO: 64).

11. The nucleic acid of claim 10, wherein the nucleic acid further encodes for a polypeptide that can be secreted from an engineered cell.

12. The nucleic acid of claim 11, wherein the polypeptide modulates the immune system of a subject.

13. The nucleic acid of claim 11, wherein the polypeptide comprises an antibody or fragment thereof.

14. The nucleic acid of claim 13, wherein the polypeptide comprises an antibody specific for TIGIT, CAIX, GITR, PD-L1, PD-L2, PD-1, or CCR4.

15. A vector comprising the nucleic acid of claim 11.

16. A cell comprising the vector of claim 15.

17. A method for treating a subject afflicted with cancer, the method comprising administering the subject a therapeutically effective amount of the engineered cell of claim 1.

18. A method of reducing progression or promoting regression of a cancer in a subject, the method comprising administering the subject a therapeutically effective amount of the engineered cell of claim 1.

19. A method of reducing cellular proliferation of a cancer cell in a subject, the method comprising administering the subject a therapeutically effective amount of the engineered cell of claim 1.

* * * * *

```
                      SEQUENCE LISTING

<160> NUMBER OF SEQ ID NOS: 131

<210> SEQ ID NO 1
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (103)..(115)
<223> OTHER INFORMATION: Any amino acid
<220> FEATURE:
<221> NAME/KEY: MOD_RES
<222> LOCATION: (117)..(117)
<223> OTHER INFORMATION: Any amino acid

<400> SEQUENCE: 1

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Xaa
            20                  25                  30

Xaa Tyr Gly Met His Trp Val Arg Gln Ala Pro Gly Lys Gly Leu Glu
        35                  40                  45

Trp Val Ala Val Ile Ser Tyr Asp Gly Ser Xaa Lys Xaa Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Lys Asp Thr Ala Val
                85                  90                  95

Tyr Tyr Cys Ala Arg Asp Xaa Xaa Xaa Xaa Xaa Xaa Xaa Xaa Xaa Xaa
            100                 105                 110

Xaa Xaa Xaa Gly Xaa Asp Val Trp Gly Gln Gly Thr Thr Val Thr Val
        115                 120                 125

Ser Ser
    130

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

```
Glu Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Val Ser Ser Leu Arg Ala Glu Asp Thr Ala Val Tyr Tyr Cys
                85                  90                  95

Val Arg Asp Leu Val Ala Ala Gly Thr Ala Phe Asp Ile Trp Gly
            100                 105                 110

Gln Gly Thr Thr Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Val Ser Gly Asp Ser Val Ser Ser Asn
            20                  25                  30

Phe Val Ala Trp Asn Trp Ile Arg Gln Ser Pro Ser Arg Gly Leu Glu
            35                  40                  45

Trp Leu Gly Arg Thr Tyr Tyr Arg Ser Arg Trp Tyr Asn Asp Tyr Ala
50                      55                  60

Val Ser Val Gln Ser Arg Ile Arg Val Thr Pro Asp Thr Ser Lys Asn
65                  70                  75                  80

Gln Phe Ser Leu His Leu Asp Ser Val Thr Pro Glu Asp Thr Ala Val
                85                  90                  95

Tyr Tyr Cys Ala Arg Gly Gln His Ser Gly Phe Asp Phe Trp Gly Gln
            100                 105                 110

Gly Thr Leu Val Thr Val Ser Ser
        115                 120

<210> SEQ ID NO 4
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45
```

```
Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Pro Gly Ile Ala Ala Arg Tyr Tyr Tyr Tyr Gly
                100                 105                 110

Met Asp Val Trp Gly Gln Gly Thr Thr Val Thr Val Ser Ser
            115                 120                 125

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Pro Met His Trp Val Arg Gln Ala Pro Gly Lys Gly Leu Glu Trp Met
            35                  40                  45

Thr Val Ile Ser Ser Asp Gly Arg Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Tyr His Asp Phe Trp Ser Gly Pro Tyr Trp Gly
                100                 105                 110

Gln Gly Thr Leu Val Thr Val Ser Ser
        115                 120

<210> SEQ ID NO 6
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Asp Gln Val Ser Gly Ile Thr Ile Phe Gly Gly Lys Trp Arg
            100                 105                 110

Ser Pro Asp Val Trp Gly Gln Gly Thr Thr Val Thr Val Ser Ser
            115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Thr Leu Lys Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Leu His Trp Val Arg Gln Ala Pro Gly Lys Gly Leu Glu Trp Val
        35                  40                  45

Ala Val Ile Ser His Asp Gly Thr Lys Lys Tyr Tyr Ala Asp Ser Val
50                  55                  60

Lys Gly Arg Phe Thr Ile Ser Arg Asp Ser Ser Glu Asn Thr Leu Tyr
65                  70                  75                  80

Leu Gln Met Asn Ser Leu Arg Pro Glu Asp Ser Ala Leu Tyr Tyr Cys
                85                  90                  95

Ala Arg Asp Gly Gly Tyr Cys Ser Gly Gly Arg Cys Tyr Ser Tyr Gly
            100                 105                 110

Met Asp Val Trp Gly Gln Gly Thr Thr Val Thr Val Ser Ser
            115                 120                 125

<210> SEQ ID NO 8
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Gly Gly Val Val Leu Pro Gly Arg
1               5                   10                  15

Ser Leu Arg Leu Ser Cys Val Ala Ser Gly Phe Thr Phe Arg Arg Tyr
            20                  25                  30

Gly Met His Trp Val Arg Gln Ala Pro Gly Lys Gly Leu Glu Trp Val
        35                  40                  45

Ser Leu Ile Ser Tyr Asp Gly Ser Lys Thr Phe Tyr Gly Glu Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Val Thr Thr Asp Gly Tyr Tyr Tyr Met Asp Val Trp
            100                 105                 110

Gly Lys Gly Thr Thr Val Thr Val Ser Ser
        115                 120

<210> SEQ ID NO 9

```
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (32)..(35)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (96)..(102)
<223> OTHER INFORMATION: Any amino acid

<400> SEQUENCE: 9

Gln Ser Val Leu Thr Gln Pro Pro Ser Val Ser Xaa Xaa Xaa Pro Gly
1               5                   10                  15

Gln Thr Val Thr Ile Ser Cys Xaa Gly Xaa Xaa Ser Xaa Xaa Gly Xaa
            20                  25                  30

Xaa Xaa Xaa Val Ser Trp Tyr Gln Gln Xaa Pro Gly Xaa Ala Pro Lys
        35                  40                  45

Leu Leu Ile Tyr Xaa Xaa Asn Xaa Arg Pro Ser Gly Ile Pro Asp Arg
    50                  55                  60

Phe Gly Ser Lys Ser Gly Asn Thr Ala Ser Leu Thr Ile Thr Gly
65                  70                  75                  80

Leu Gln Ala Lys Asp Ala Lys Lys Tyr Tyr Cys Xaa Ser Trp Asp Xaa
                85                  90                  95

Xaa Xaa Xaa Xaa Xaa Xaa Val Phe Gly Gly Gly Thr Lys Leu Thr Val
            100                 105                 110

Leu Gly

<210> SEQ ID NO 10
<211> LENGTH: 111
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Pro Val Leu Thr Gln Pro Arg Ser Val Ser Gly Ser Pro Gly Gln
1               5                   10                  15

Ser Val Thr Ile Ser Cys Thr Gly Thr Ile Ser Asp Val Gly Gly His
            20                  25                  30

Asn Phe Val Ser Trp Tyr Gln Gln Asn Pro Gly Lys Ala Pro Lys Leu
        35                  40                  45

Ile Ile Phe Glu Val Thr Lys Arg Pro Ala Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Gly Glu Tyr Tyr Cys Ser Ser Tyr Gly Gly Ser
                85                  90                  95

Asn Asp Val Ile Phe Gly Gly Gly Thr Lys Leu Ser Val Leu Gly
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Met Asp Asn Arg Leu
                85                  90                  95

Lys Thr Tyr Val Phe Gly Thr Gly Gly Lys Val Thr Val Leu Gly
            100                 105                 110

<210> SEQ ID NO 12
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Lys Phe Phe Ala
            20                  25                  30

Ser Trp Tyr Gln Gln Lys Pro Gly Gln Ala Pro Val Leu Val Ile Tyr
```

```
                    35                  40                  45
Gly Lys Asn Ser Arg Pro Ser Gly Ile Pro Asp Arg Phe Ser Gly Ser
 50                  55                  60

Asn Ser Arg Asn Thr Ala Ser Leu Thr Ile Thr Gly Ala Gln Ala Glu
 65                  70                  75                  80

Asp Glu Gly Asp Tyr Tyr Cys Asn Ser Arg Asp Ser Arg Asp Asn His
                     85                  90                  95

Gln Val Phe Gly Ala Gly Thr Lys Val Thr Val Leu Ser
                100                 105
```

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Ile Val Leu Thr Gln Ser Pro Ala Thr Leu Ser Val Ser Pro Gly
 1                   5                  10                  15

Lys Arg Ala Thr Leu Ser Cys Arg Ala Ser Gln Ser Val Asn Thr Asn
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln His Tyr Gly Ser Ser Pro Leu
                     85                  90                  95

Thr Phe Gly Gly Gly Thr Lys Leu Glu Ile Lys Arg
                100                 105
```

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Ser Ser Glu Leu Thr Gln Asp Pro Ala Val Ser Val Ala Leu Gly Gln
 1                   5                  10                  15

Thr Val Arg Ile Thr Cys Gln Gly Asp Ser Leu Arg Ser Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Lys Ser His Asn Thr Ala Tyr Leu Thr Ile Thr Gly Ala Gln Ala Glu
 65                  70                  75                  80

Asp Glu Ala Asp Tyr Phe Cys Asn Ser Arg Ser Gly Ser Gln Arg Val
                     85                  90                  95

Phe Gly Gly Gly Thr Lys Leu Thr Val Leu Gly
                100                 105
```

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Leu Ser Phe Asp Ser Ser Leu
                85                  90                  95

Thr Ser Tyr Val Phe Gly Thr Gly Thr Lys Val Thr Val Leu Gly
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly His Val Val Phe Gly Gly Thr Lys Leu Thr Val Leu Arg
            100                 105                 110

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Tyr Gly Met His
1               5

<210> SEQ ID NO 18

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Ile Ser Tyr Asp Gly Ser Asn Lys Tyr Tyr Ala Asp Ser Val Lys
1               5                   10                  15

Gly

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Leu Val Ala Ala Ala Gly Thr Ala Phe Asp Ile
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Gly Thr Ile Ser Asp Val Gly Gly His Asn Phe Val Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Val Thr Lys Arg Pro Ala
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ser Tyr Gly Gly Ser Asn Asp Val Ile
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Ser Asn Phe Val Ala Trp Asn
1               5

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Thr Tyr Tyr Arg Ser Arg Trp Tyr Asn Asp Tyr Ala Val Ser Val
1               5                   10                  15

Gln Ser

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gln His Ser Gly Phe Asp Phe
1               5

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Gly Asn Ser Asn Asn Val Gly Asn Gln Gly Ala Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Asn Asn Asn Arg Pro Ser
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ala Trp Asp Asn Arg Leu Lys Thr Tyr Val
1               5                   10

<210> SEQ ID NO 29
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Gly Ile Ser
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Ile Ser Ala Tyr Asn Gly Asn Thr Asn Tyr Ala Gln Lys Leu Gln
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Thr Pro Gly Ile Ala Ala Arg Arg Tyr Tyr Tyr Tyr Gly Met Asp
1               5                   10                  15

Val

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gly Asp Ser Leu Arg Lys Phe Phe Ala Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Lys Asn Ser Arg Pro Ser
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                           peptide

<400> SEQUENCE: 34

Asn Ser Arg Asp Ser Arg Asp Asn His Gln Val
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Tyr Pro Met His
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Ile Ser Ser Asp Gly Arg Asn Lys Tyr Tyr Pro Asp Ser Val Lys
1               5                   10                  15

Gly

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Tyr His Asp Phe Trp Ser Gly Pro Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ala Ser Gln Ser Val Asn Thr Asn Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ala Ser Ser Arg Ala Thr
1               5
```

```
<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln His Tyr Gly Ser Ser Pro Leu Thr
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Tyr Ala Met Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Ile Lys Gln Asp Gly Ser Glu Lys Tyr Tyr Val Asp Ser Val Lys
1               5                   10                  15

Gly

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Gln Val Ser Gly Ile Thr Ile Phe Gly Gly Lys Trp Arg Ser Pro
1               5                   10                  15

Asp Val

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Asp Ser Leu Arg Ser Tyr Tyr Ala Ser
1               5                   10

<210> SEQ ID NO 45
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 45

Gly Lys Asn Asn Arg Pro Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Ser Arg Ser Gly Ser Gln Arg Val
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asn Tyr Gly Leu His
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Ile Ser His Asp Gly Thr Lys Lys Tyr Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Gly Gly Tyr Cys Ser Gly Gly Arg Cys Tyr Ser Tyr Gly Met Asp
1               5                   10                  15

Val

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Ser Gly Ser Arg Ser Asn Ile Gly Ser Asn Thr Val Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Asn Asn Gln Arg Pro Ser
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Ser Phe Asp Ser Ser Leu Thr Ser Tyr Val
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Tyr Gly Met His
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Ile Ser Tyr Asp Gly Ser Lys Thr Phe Tyr Gly Glu Ser Val Lys
1               5                   10                  15

Gly

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Thr Val Thr Thr Asp Gly Tyr Tyr Tyr Met Asp Val
1               5                   10

<210> SEQ ID NO 56
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Ser Arg Ser Asn Ile Gly Gly Asn Thr Val Asn
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Asn Asn Gln Arg Pro Ser
1               5

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ala Trp Asp Asp Asn Leu Ser Gly His Val Val
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Phe Thr Val Ser Ser Asn Tyr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Tyr Ser Gly Gly Ser Thr
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Arg Asp Asn Pro Leu Ser Ala Phe Asp Ile
```

```
                1               5                       10
```

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Ile Asn Ser Trp
1               5

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Ala Ser
1

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Tyr Asp Asp Leu Pro Leu Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Tyr Thr Phe Thr Ser Tyr Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Ser Ala Tyr Asn Gly Asn Thr
1               5

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 67

Ala Arg Asp Pro Gly Leu Trp Phe Gly Leu Thr His Asp Tyr Tyr Phe
1               5                   10                  15

Asp Tyr

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Ser Asn Ile Gly Ser Asn Thr
1               5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Asn Asn
1

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ala Trp Asp Asp Ser Arg Ser Gly Pro Val
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Thr Phe Ser Asp Tyr Ser
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Asn Ser Asp Gly Ser Arg Thr
1               5
```

```
<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Gly Pro Gly Phe Phe Gly Phe Asp Ile
1               5                   10

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ser Asn Ile Gly Arg Asn Ser
1               5

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Asn Asn
1

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Ala Trp Asp Ala Arg Leu Thr Gly Pro Leu
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Ser Phe Thr Asn Tyr Trp
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 78

Ile Asn Pro Val Asn Ser Arg Thr
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Tyr Tyr Tyr Ala Met Glu Val
1               5               10

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ser Asn Ile Gly Ser Asn Thr
1               5

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Asn Asn
1

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Ala Trp Asp Asp Ser Leu Asn Gly Pro Val
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Tyr Thr Phe Thr Asn Tyr Gly
1               5

<210> SEQ ID NO 84
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 84

Val Asp Asn Asn Asn Gly Asn Ile
1               5

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Gly Leu Phe Ser Ser Arg Trp Tyr Leu Trp Phe Asp Pro
1               5                   10                  15

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Ser Asp Val Gly Gly Tyr Asn Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Val Thr
1

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ser Tyr Thr Arg Ser Ser Thr Ser Tyr Val Val
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Thr Phe Ser Ser Tyr Ala
1               5
```

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Leu Pro Met Phe Gly Ser Thr
1               5

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Gly Arg Asp Ile Val Ala Pro Ser Asn Ser Gly Phe Asp Val
1               5                   10                  15

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Asn Asn Val Gly Asn Gln Gly
1               5

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Asn Asp
1

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ala Tyr Asp Arg Ser Leu Asn Ala Trp Val
1               5                   10

<210> SEQ ID NO 95
<211> LENGTH: 328
<212> TYPE: PRT
<213> ORGANISM: Homo sapiens
<220> FEATURE:
<221> NAME/KEY: NON_CONS
<222> LOCATION: (315)..(316)

<400> SEQUENCE: 95

```
Met Glu Gly Ile Ser Ile Tyr Thr Ser Asp Asn Tyr Thr Glu Met
1               5                   10                  15

Gly Ser Gly Asp Tyr Asp Ser Met Lys Glu Pro Cys Phe Arg Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Val Ser Thr Glu Ser
305                 310                 315                 320

Glu Ser Ser Ser Phe His Ser Ser
                325
```

<210> SEQ ID NO 96
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Glu Val Gln Leu Val Gln Ser Gly Gly Gly Leu Ile Gln Pro Gly Gly
1               5                   10                  15
```

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
            85                  90                  95

Arg Asp Asn Pro Leu Ser Ala Phe Asp Ile Trp Gly Gln Gly Thr Leu
            100                 105                 110

Val Thr Val Ser Leu
        115

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Thr Gln Thr Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Ser Gly Lys Ala Pro Lys Leu Leu Ile
        35                  40                  45

Tyr Lys Ala Ser Ser Leu Gly Ser Gly Val Pro Ser Arg Phe Ser Gly
 50                  55                  60

Ser Gly Ser Asp Ile Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Leu
            85                  90                  95

Thr Phe Gly Gly Gly Thr Lys Val Glu Ile Lys
            100                 105

<210> SEQ ID NO 98
<211> LENGTH: 97
<212> TYPE: PRT
<213> ORGANISM: Homo sapiens

<400> SEQUENCE: 98

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 99
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asn Pro Leu Ser Ala Phe Asp Ile Trp Gly Gln Gly Thr Leu
            100                 105                 110

Val Thr Val Ser Leu
        115

<210> SEQ ID NO 100
<211> LENGTH: 95
<212> TYPE: PRT
<213> ORGANISM: Homo sapiens

<400> SEQUENCE: 100

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Val Met Thr Gln Thr Pro Ser Thr Leu Ser Ala Ser Val Gly
1               5                   10                  15

Asp Arg Val Thr Ile Thr Cys Arg Ala Ser Gln Ser Ile Asn Ser Trp

```
                    20                  25                  30
Leu Ala Trp Tyr Gln Gln Lys Ser Gly Lys Ala Pro Lys Leu Leu Ile
            35                  40                  45
Tyr Lys Ala Ser Ser Leu Gly Ser Gly Val Pro Ser Arg Phe Ser Gly
     50                  55                  60
Ser Gly Ser Asp Ile Glu Phe Thr Leu Thr Ile Ser Ser Leu Gln Pro
65                  70                  75                  80
Asp Asp Phe Ala Thr Tyr Tyr Cys Gln Gln Tyr Asp Asp Leu Pro Leu
                85                  90                  95
Thr Phe Gly Gly Gly Thr Lys Val Glu Ile Lys
            100                 105

<210> SEQ ID NO 102
<211> LENGTH: 98
<212> TYPE: PRT
<213> ORGANISM: Homo sapiens

<400> SEQUENCE: 102

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
     50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg

<210> SEQ ID NO 103
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
     50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Pro Gly Leu Trp Phe Gly Leu Thr His Asp Tyr Tyr Phe
            100                 105                 110
Asp Tyr Trp Gly Gln Gly Thr Leu Val Thr Val Ser Ser
     115                 120                 125
```

<210> SEQ ID NO 104
<211> LENGTH: 98
<212> TYPE: PRT
<213> ORGANISM: Homo sapiens

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 105
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Asn Gly Leu Gln
65                  70                  75                  80

Ser Glu Asp Glu Ala Asp Tyr Tyr Cys Ala Ala Trp Asp Asp Ser Arg
                85                  90                  95

Ser Gly Pro Val Phe Gly Gly Gly Thr Arg Leu Thr Val Leu
            100                 105                 110

<210> SEQ ID NO 106
<211> LENGTH: 98
<212> TYPE: PRT
<213> ORGANISM: Homo sapiens

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Gly Gly Leu Val Lys Pro Gly Gly
1               5                   10                  15

Ser Leu Arg Leu Ser Cys Glu Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Arg Ile Asn Ser Asp Gly Ser Arg Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Pro Gly Phe Phe Gly Phe Asp Ile Trp Gly Gln Gly Thr
            100                 105                 110

Leu Val Thr Val Ser Ser
        115

<210> SEQ ID NO 108
<211> LENGTH: 98
<212> TYPE: PRT
<213> ORGANISM: Homo sapiens

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 109
<211> LENGTH: 110
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 109

Ser Tyr Glu Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Arg Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Gly Arg Phe Ser
50                  55                  60

Gly Ser Arg Ser Gly Thr Ser Ala Ser Leu Ala Ile Ser Gly Leu Gln
65                  70                  75                  80

Ser Glu Asp Glu Thr Asp Tyr Tyr Cys Ala Ala Trp Asp Ala Arg Leu
                85                  90                  95

Thr Gly Pro Leu Phe Gly Gly Gly Thr Lys Leu Ser Val Leu
            100                 105                 110

<210> SEQ ID NO 110
<211> LENGTH: 98
<212> TYPE: PRT
<213> ORGANISM: Homo sapiens

<400> SEQUENCE: 110

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 111
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Asn Pro Val Asn Ser Arg Thr Ile Tyr Ser Pro Ser Phe
50                  55                  60

Gln Gly Gln Val Thr Ile Ser Val Asp Lys Ser Val Thr Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Tyr Tyr Tyr Tyr Ala Met Glu Val Trp Gly Arg Gly Thr Leu
            100                 105                 110

Val Thr Val Ser Ser
        115

<210> SEQ ID NO 112
<211> LENGTH: 98
<212> TYPE: PRT
<213> ORGANISM: Homo sapiens

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 113
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Thr Ser Gly Thr Ser Ala Ser Leu Ala Ile Ser Gly Leu Gln
65                  70                  75                  80

Ser Glu Asp Glu Ala Asp Tyr Tyr Cys Glu Ala Trp Asp Asp Ser Leu
                85                  90                  95

Asn Gly Pro Val Phe Gly Gly Gly Thr Lys Leu Thr Val Leu
                100                 105                 110

<210> SEQ ID NO 114
<211> LENGTH: 98
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
```

```
                1               5                    10                   15
            Ser Val Lys Val Ser Cys Lys Ala Ser Gly Tyr Thr Phe Thr Ser Tyr
                           20                  25                  30
            Gly Ile Ser Trp Val Arg Gln Ala Pro Gly Gln Gly Leu Glu Trp Met
                           35                  40                  45
            Gly Trp Ile Ser Ala Tyr Asn Gly Asn Thr Asn Tyr Ala Gln Lys Leu
                           50                  55                  60
            Gln Gly Arg Val Thr Met Thr Thr Asp Thr Ser Thr Ser Thr Ala Tyr
             65                 70                  75                  80
            Met Glu Leu Arg Ser Leu Arg Ser Asp Asp Thr Ala Val Tyr Tyr Cys
                           85                  90                  95

Ala Arg

<210> SEQ ID NO 115
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Gln Ser Gly Ala Glu Val Lys Lys Pro Gly Ala
            1               5                    10                   15
            Ser Val Lys Val Ser Cys Lys Ala Ser Gly Tyr Thr Phe Thr Asn Tyr
                           20                  25                  30
            Gly Ile Ser Trp Val Arg Gln Ala Pro Gly Gly Gly Leu Glu Trp Met
                           35                  40                  45
            Gly Trp Val Asp Asn Asn Gly Asn Ile Asn Tyr Ala Gln Lys Phe
                           50                  55                  60
            Leu Gly Arg Val Thr Met Thr Thr Asp Thr Ser Thr Ser Thr Ala Tyr
             65                 70                  75                  80
            Met Glu Leu Arg Ser Leu Arg Ser Asp Asp Thr Ala Val Tyr Tyr Cys
                           85                  90                  95
            Ala Arg Gly Leu Phe Ser Ser Arg Trp Tyr Leu Trp Phe Asp Pro Trp
                           100                 105                 110
            Gly Gln Gly Thr Leu Val Thr Val Ser Ser
                           115                 120

<210> SEQ ID NO 116
<211> LENGTH: 99
<212> TYPE: PRT
<213> ORGANISM: Homo sapiens

<400> SEQUENCE: 116

Gln Ser Ala Leu Thr Gln Pro Ala Ser Val Ser Gly Ser Pro Gly Gln
            1               5                    10                   15
            Ser Ile Thr Ile Ser Cys Thr Gly Thr Ser Ser Asp Val Gly Gly Tyr
                           20                  25                  30
            Asn Tyr Val Ser Trp Tyr Gln Gln His Pro Gly Lys Ala Pro Lys Leu
                           35                  40                  45
            Met Ile Tyr Glu Val Ser Asn Arg Pro Ser Gly Val Ser Asn Arg Phe
                           50                  55                  60
            Ser Gly Ser Lys Ser Gly Asn Thr Ala Ser Leu Thr Ile Ser Gly Leu
             65                 70                  75                  80
            Gln Ala Glu Asp Glu Ala Asp Tyr Tyr Cys Ser Ser Tyr Thr Ser Ser
                           85                  90                  95
```

Ser Thr Leu

<210> SEQ ID NO 117
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Thr Arg Ser
                85                  90                  95

Ser Thr Ser Tyr Val Val Phe Gly Gly Gly Thr Lys Val Thr Val Leu
            100                 105                 110
```

<210> SEQ ID NO 118
<211> LENGTH: 98
<212> TYPE: PRT
<213> ORGANISM: Homo sapiens

<400> SEQUENCE: 118

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 119
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
            35                  40                  45

Gly Gly Ile Leu Pro Met Phe Gly Ser Thr Asn Tyr Ala Gln Lys Phe
        50                  55                  60

Gln Gly Arg Leu Thr Leu Ile Ala Asp Glu Ser Thr Arg Thr Val Tyr
65                  70                  75                  80

Leu Glu Leu Asn Ser Leu Thr Ser Glu Asp Thr Ala Val Tyr Tyr Cys
                85                  90                  95

Ala Arg Gly Arg Asp Ile Val Ala Pro Ser Asn Ser Gly Phe Asp Val
                100                 105                 110

Trp Gly Gln Gly Thr Thr Val Thr Val Ser Ser
            115                 120

<210> SEQ ID NO 120
<211> LENGTH: 98
<212> TYPE: PRT
<213> ORGANISM: Homo sapiens

<400> SEQUENCE: 120

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asn Asn Arg Pro Ser Gly Ile Ser Glu Arg Leu Ser
        50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala

<210> SEQ ID NO 121
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ser Tyr Glu Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asp Asn Arg Pro Ser Gly Ile Ser Glu Arg Phe Ser
        50                  55                  60

Ala Ser Arg Ser Gly Asn Thr Ala Ser Leu Thr Ile Ser Gly Leu Gln
65                  70                  75                  80

Pro Glu Asp Glu Ala Asp Tyr Tyr Cys Ser Ala Tyr Asp Arg Ser Leu
                85                  90                  95

Asn Ala Trp Val Phe Gly Gly Gly Thr Lys Leu Thr Val Leu
                100                 105                 110

<210> SEQ ID NO 122
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Gly Leu Trp Phe Gly Leu Thr His Asp Tyr Tyr Phe
                100                 105                 110

Asp Tyr Trp Gly Gln Gly Thr Leu Val Thr Val Ser Ser
            115                 120                 125

<210> SEQ ID NO 123
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Gln Ser Gly Gly Gly Leu Val Lys Pro Gly Gly
1               5                   10                  15

Ser Leu Arg Leu Ser Cys Glu Ala Ser Gly Phe Thr Phe Ser Asp Tyr
                20                  25                  30

Ser Met Ser Trp Ile Arg Gln Ala Pro Gly Lys Gly Leu Glu Trp Val
            35                  40                  45

Ser Arg Ile Asn Ser Asp Gly Ser Arg Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Pro Gly Phe Phe Gly Phe Asp Ile Trp Gly Gln Gly Thr
                100                 105                 110

Leu Val Thr Val Ser Ser
            115

<210> SEQ ID NO 124
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 124

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Asn Pro Val Asn Ser Arg Thr Ile Tyr Ser Pro Ser Phe
50                  55                  60

Gln Gly Gln Val Thr Ile Ser Val Asp Lys Ser Val Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Tyr Tyr Tyr Ala Met Glu Val Trp Gly Arg Gly Thr Leu
            100                 105                 110

Val Thr Val Ser Ser
        115

<210> SEQ ID NO 125
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gly Gly Leu Glu Trp Met
        35                  40                  45

Gly Trp Val Asp Asn Asn Asn Gly Asn Ile Asn Tyr Ala Gln Lys Phe
50                  55                  60

Leu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Leu Phe Ser Ser Arg Trp Tyr Leu Trp Phe Asp Pro Trp
            100                 105                 110

Gly Gln Gly Thr Leu Val Thr Val Ser Ser
        115                 120

<210> SEQ ID NO 126
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
            35                  40                  45
Gly Gly Ile Leu Pro Met Phe Gly Ser Thr Asn Tyr Ala Gln Lys Phe
 50                  55                  60
Gln Gly Arg Leu Thr Leu Ile Ala Asp Glu Ser Thr Arg Thr Val Tyr
 65                  70                  75                  80
Leu Glu Leu Asn Ser Leu Thr Ser Glu Asp Thr Ala Val Tyr Tyr Cys
                 85                  90                  95
Ala Arg Gly Arg Asp Ile Val Ala Pro Ser Asn Ser Gly Phe Asp Val
            100                 105                 110
Trp Gly Gln Gly Thr Thr Val Thr Val Ser Ser
            115                 120
```

<210> SEQ ID NO 127
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Ser Tyr Glu Leu Thr Gln Pro Pro Ser Ala Ser Gly Thr Pro Gly Gln
 1               5                  10                  15
Arg Val Thr Ile Ser Cys Ser Gly Ser Ser Ser Asn Ile Gly Ser Asn
            20                  25                  30
Thr Val Ser Trp Tyr Gln Gln Leu Pro Gly Thr Ala Pro Lys Leu Leu
         35                  40                  45
Ile Tyr Arg Asn Asn Gln Arg Pro Ser Gly Val Pro Asp Arg Phe Ser
 50                  55                  60
Gly Ser Lys Ser Gly Thr Ser Ala Ser Leu Ala Ile Asn Gly Leu Gln
 65                  70                  75                  80
Ser Glu Asp Glu Ala Asp Tyr Tyr Cys Ala Ala Trp Asp Asp Ser Arg
                 85                  90                  95
Ser Gly Pro Val Phe Gly Gly Gly Thr Arg Leu Thr Val Leu
            100                 105                 110
```

<210> SEQ ID NO 128
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Ser Tyr Glu Leu Thr Gln Pro Pro Ser Ala Ser Gly Thr Pro Gly Gln
 1               5                  10                  15
Arg Val Thr Ile Ser Cys Ser Gly Ser Arg Ser Asn Ile Gly Arg Asn
            20                  25                  30
Ser Val Asn Trp Tyr Gln Gln Leu Pro Gly Thr Ala Pro Lys Leu Leu
         35                  40                  45
Ile Tyr Ser Asn Asn Gln Arg Pro Ser Gly Val Pro Gly Arg Phe Ser
 50                  55                  60
Gly Ser Arg Ser Gly Thr Ser Ala Ser Leu Ala Ile Ser Gly Leu Gln
 65                  70                  75                  80
Ser Glu Asp Glu Thr Asp Tyr Tyr Cys Ala Ala Trp Asp Ala Arg Leu
                 85                  90                  95
Thr Gly Pro Leu Phe Gly Gly Gly Thr Lys Leu Ser Val Leu
```

<210> SEQ ID NO 129
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Thr Ser Gly Thr Ser Ala Ser Leu Ala Ile Ser Gly Leu Gln
65                  70                  75                  80

Ser Glu Asp Glu Ala Asp Tyr Tyr Cys Glu Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Thr Arg Ser
                85                  90                  95

Ser Thr Ser Tyr Val Val Phe Gly Gly Gly Thr Lys Val Thr Val Leu
            100                 105                 110

<210> SEQ ID NO 131
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ser Tyr Glu Leu Thr Gln Pro Pro Ser Val Ser Lys Gly Leu Arg Gln
1               5                   10                  15

-continued

```
Thr Ala Thr Leu Thr Cys Thr Gly Asn Ser Asn Asn Val Gly Asn Gln
            20              25              30

Gly Ala Ala Trp Leu Gln Gln His Gln Gly His Pro Pro Lys Leu Leu
            35              40              45

Ser Tyr Arg Asn Asp Asn Arg Pro Ser Gly Ile Ser Glu Arg Phe Ser
 50              55              60

Ala Ser Arg Ser Gly Asn Thr Ala Ser Leu Thr Ile Ser Gly Leu Gln
 65              70              75              80

Pro Glu Asp Glu Ala Asp Tyr Tyr Cys Ser Ala Tyr Asp Arg Ser Leu
            85              90              95

Asn Ala Trp Val Phe Gly Gly Gly Thr Lys Leu Thr Val Leu
            100             105             110
```